(12) United States Patent
Stojadinovic et al.

(10) Patent No.: US 8,510,245 B2
(45) Date of Patent: Aug. 13, 2013

(54) BAYESIAN CLINICAL DECISION MODEL FOR DETERMINING PROBABILITY OF TRANSPLANT GLOMERULOPATHY

(75) Inventors: Alexander Stojadinovic, Chevy Chase, MD (US); Eric A. Elster, Kensington, MD (US); Doug K. Tadaki, Frederick, MD (US); John S. Eberhardt, III, Washington, DC (US); Trevor Brown, Washington, DC (US); Thomas A. Davis, Oak Hill, VA (US); Jonathan Forsberg, Kensington, MD (US); Jason Hawksworth, Silver Spring, MD (US); Roslyn Mannon, Birmingham, AL (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 290 days.

(21) Appl. No.: 13/083,184

(22) Filed: Apr. 8, 2011

(65) Prior Publication Data
US 2011/0289036 A1 Nov. 24, 2011

Related U.S. Application Data

(63) Continuation of application No. PCT/US2009/060850, filed on Oct. 15, 2009.

(60) Provisional application No. 61/166,245, filed on Apr. 2, 2009, provisional application No. 61/105,786, filed on Oct. 15, 2008.

(51) Int. Cl.
*G06N 5/00* (2006.01)

(52) U.S. Cl.
USPC .......................................................... 706/45

(58) Field of Classification Search
USPC .......................................................... 706/45
See application file for complete search history.

(56) References Cited

U.S. PATENT DOCUMENTS

| | | | |
|---|---|---|---|
| 7,056,674 B2 | 6/2006 | Baker et al. | |
| 7,379,926 B1 | 5/2008 | Belniak et al. | |
| 7,526,387 B2 | 4/2009 | Baker et al. | |

OTHER PUBLICATIONS

Taal, et al., Predicting initiation and progression of chronic kidney disease: Developing renal risk scores, Kidney International, 70, 2006, pp. 1694-1705.*
Welker MJ, et al., Thyroid nodules, Am Fam Physician 2003; 67:559-66,573-4.
Mazzaferri EL, Thyroid cancer in thyroid nodules: finding a needle in the haystack, Am J Med 1992; 93:359-62.

(Continued)

*Primary Examiner* — Wilbert L Starks
(74) *Attorney, Agent, or Firm* — Elizabeth Arwine

(57) ABSTRACT

An embodiment of the invention provides a method for determining a patient-specific probability of transplant glomerulopathy. The method collects clinical parameters from a plurality of patients to create a training database. A fully unsupervised Bayesian Belief Network model is created using data from the training database; and, the fully unsupervised Bayesian Belief Network is validated. Clinical parameters are collected from an individual patient; and, such clinical parameters are input into the fully unsupervised Bayesian Belief Network model via a graphical user interface. The patient-specific probability of transplant glomerulopathy is output from the fully unsupervised Bayesian Belief Network model and sent to the graphical user interface for use by a clinician in pre-operative planning. The fully unsupervised Bayesian Belief Network model is updated using the clinical parameters from the individual patient and the patient-specific probability of transplant glomerulopathy.

7 Claims, 55 Drawing Sheets

(56) References Cited

OTHER PUBLICATIONS

Baloch ZW, et al., The National Cancer Institute Thyroid fine needle aspiration state of the science conference: a summation, Cytojournal Apr. 7 2008; 5:6.
Are C., et al., FDG-PET detected thyroid incidentalomas: Need for further investigation? Ann Surg Oncol 2007, 14:239-247.
Sathekge MM, et al., Evaluation of thyroid nodules with technetium-909m MIBI and technetium-99m pertechnetate, Head Neck 2001, 23:305-310.
Baloch ZW, et al., Fine-needle aspiration of thyroid nodules: past, present, and future, Endocr Pract, May-Jun. 2004; 10(3):234-41.
Deveci MS, et al., Fine-needle aspiration of follicular lesions of the thyroid. Diagnosis and follow-Up, Cytojournal, Apr. 7, 2006; 3:9.
Nissan A, et al., Prospective trial evaluating electrical impedance scanning of thyroid nodules before thyroidectomy: Final results, Ann Surg. May 2008; 247(5):843-53.
Stojadinovic A, et al., Electrical Impedance Scanning of Thyroid Nodules Prior to Thyroid Surgery: A Prospective Study, Annals of Surgical Oncology 2005; 12(2): 152-160.
Varverakis E., et al., Role of color Doppler ultrasonography in the preoperative management of cold thyroid nodules, Hormones 2007; 6(1):44-51.
Lyshcik A, et al., Quantitative analysis of tumor vascularity in benign and malignant solid thyroid nodules, J Ultrasound Med. Jun. 2007; 26(6):837-46.
Varverakis E, Neonakis E., Contribution of high-resolution ultrasonography in the differential diagnosis of benign from malignant thyroid nodules, Hormones (Athens) 2002; 1:51-56.
Spiezia S, et al., Usefulness of power Doppler in the diagnostic management of hypoechoic thyroid nodules, Eur J Ultrasound 1997; 6: 165-170.
Rago T, et al., Role of conventional ultrasonography and color flowdoppler sonography in predicting malignancy in 'cold' thyroid nodules, Eur J Endocrinol Jan. 1998; 138(1):41-6.
Bae U, et al., Ultrasound thyroid elastography using carotid artery pulsation: preliminary study, J Ultrasound Med. Jun. 2007; 26(6):797-805.
Rago T, et al., Elastography: new developments in ultrasound for predicting malignancy in thyroid nodules, J Clin Endocrinol Metab. Aug. 2007; 92(8):2917-22.
Sebastianes FM, et al., Role of 18F-FDG PET in Preoperative Assessment of Cytologically Indeterminate Thyroid Nodules, J Clin Endocrinol Metab. Aug. 7, 2007.
De Geus-Oei, et al., 18 F-FDG PET reduces unnecessary hemithyroidectomies for thyroid nodules with indeterminate cytologic results, J Nucl Med 2006; 47:770-775.
Fricke H., et al., The electric capacity of tumors of the breast, J Cancer Res 16:310-376. 1926.
Scholz B., et al., On electrical impedance scanning—principles and simulations, Electromedica 2000; 68:35-44.
Glickman YA, et al., Electrical impedance scanning: a new approach to skin cancer diagnosis, Skin Res Technol. Aug. 2003; 9(3):262-8.
Malich A, et al., Electrical impedance scanning: a new technique in the diagnosis of lymph nodes in which malignancy is suspected on ultrasound, Br J Radiol. 2001; 74(877):42-7.
Malich A, et al., Use of electrical impedance scanning in the differentiation of sonographically suspicious and highly suspicious lymph nodes of the headneck region, Eur Radiol. 2002; 12(5):1114-20.
Mentzel HJ, et al., Electrical impedance scanning-application of this new technique for lymph node evaluation in children, Pediatr Radiol. 2003; 33(7):461-6.
Malich A, et al., Electrical impedance scanning for classifying suspicious breast lesions: first results, Eur Radiol. 2000; 10(10):1555-61.
Malich A, et al., Differentiation of mammographically suspicious lesions: evaluation of breast ultrasound, MRI mammography and electrical impedance scanning as adjunctive technologies in breast cancer detection, Clinical Radiology 2001; 56: 278-83.

Fuchsjaeger MH, et al., The negative predictive value of electrical impedance scanning in BI-RADS category IV breast lesions, Invest Radiol. 2005; 40(7):478-85.
Stojadinovic A, et al., Electrical Impedance Scanning for the Early Detection of Breast Cancer in Young Women: Preliminary Results of a Multi-Center Prospective Clinical Trial, J Clin Oncol 2005; 23(12):2703-2715.
Stojadinovic A, et al., Prospective Study of Electrical Impedance Scanning for Identifying Young Women at Risk for Breast Cancer, Br Cancer Res Treat 2006; 97(2): 179-89.
Tuttle RM, et al., Clinical features associated with an increased risk of thyroid malignancy in patients with follicular neoplasia by fine-needle aspiration, Thyroid May 1998; 8(5):377-83.
Montgomery, S.P., et al., The evaluation of casualties from Operation Iraqi Freedom on return to the continental United States from Mar. to Jun. 2003, J Am Coll Surg 201:7-12; discussion 12-13 (2005).
Peoples, G.E., et al., Caring for the wounded in Iraq—a photo essay, N Engl J Med 351:2476-2480 (2004).
Owens, B.D., et al., Combat wounds in operation Iraqi Freedom and operation Enduring Freedom, J Trauma 64:295-299 (2008).
Marsh, D.J., et al., The role of vacuum-assisted wound closure in blast injury, Plast Reconstr Surg 119:1978-1979 (2007).
Breugem, C.C., et al., Is there evidence-based guidance for timing of soft tissue coverage of grade III B tibia fractures? Int J Low Extrem Wounds 5:261-270 (2006).
Nwomeh, B.C., et al., Physiology of the chronic wound, Clin Plast Surg 25:341-356 (1998).
Delong, W.G., Jr., et al., Cytokines in patients with polytrauma, Clin Orthop Relat Res:57-65 (2004).
Nast-Kolb, D., et al., Indicators of the posttraumatic inflammatory response correlate with organ failure in patients with multiple injuries, J Trauma 42, 446-455 (1997).
Endo, S., et al., Plasma endotoxin and cytokine concentrations in patients with hemorrhagic shock, Crit Care Med 22, 949-955 (1994).
Martin, C., et al., "Patterns of cytokine evolution (tumor necrosis factor-alpha and interleukin-6) after septic shock, hemorrhagic shock, and severe trauma," Crit Care Med 25, 1813-1819 (1997).
Biffl, W.L., et al., "Interleukin-6 in the injured patient. Marker of injury or mediator of inflammation?" Ann Surg 224, 647-664 (1996).
Neidhart, R., et al., "Relationship of interleukin-10 plasma levels to severity of injury and clinical outcome in injured patients," J Trauma 42, 863-870; discussion 870-861 (1997).
Lyons, A., et al., "Major injury induces increased production of interleukin-10 by cells of the immune system with a negative impact on resistance to infection," Ann Surg 226, 450-458; discussion 458-460 (1997).
Regan MC, et al., "Host defense dysfunction in trauma, shock and sepsis: mechanisms and therapeutic approaches, in Faist E," Meakins J, Schildberg FW, eds., Host Defense Dysfunction in Trauma, Shock and Sepsis, Springer, Berlin, 1993, 1043-49.
Robson, M.C., et al., "Wound infection. A failure of wound healing caused by an imbalance of bacteria," Surg Clin North Am 77, 637-650 (1997).
Medzhitov, R., "Recognition of microorganisms and activation of the immune response," Nature 449, 819-826 (2007).
Dinarello,C.A., "Proinflammatory cytokines," Chest 118:503-508 (2000).
Foex, B.A., et al., "Early cytokine response to multiple injury," Injury 24:373-376 (1993).
Jemal A. et al., "Cancer Statistics 2009," CA Cancer J Clin Jul.-Aug. 2009; 59(4):225-49.
Cancer Facts and Figures 2008, Atlanta, GA; American Cancer Society: 2009.
Saving Women's Lives: Strategies for Improving Breast Cancer Detection and Diagnosis, Joy JE, Penhoet EE, and Petitti DB, eds., Institute of Medicine and National Research Council of the National Academies, National Academy Press, Washington DC, 2004.
Winchester DP, et al., "The National Cancer Data Base report on breast carcinoma characteristics and outcome in relation to age," Cancer 1996; 78:1838-1843.
Chung M, et al., "Younger women with breast carcinoma have a poorer prognosis than older women," Cancer 1996; 77:97-103.

Xiong Q., et al., "Female patients with breast carcinoma age 30 years and younger have a poor prognosis: The M.D. Anderson Cancer Center experience," Cancer 2001; 92(10):2523-8.

Smith RA, et al., "American Cancer Society guidelines for breast cancer screening: update 2003," CA Cancer J Clin 2003; 53(3): 141-69.

Kollias J., et al., "Screening women aged less than 50 years with a family history of breast cancer," Eur J Cancer 1998; 34:878-83.

Tilanus-Lindhorst MM, et al., "Earlier detection of breast cancer by surveillance of women at familial risk," Eur J Cancer 2000; 36:514-19.

Carney PA, et al., "Individual and combined effects of age, breast density, and hormone replacement therapy use on the accuracy of screening mammography," Ann.Intern.Med 2003; 138(3): 168-175.

Kroenke CH, et al., "Functional impact of breast cancer by age at diagnosis," J Clin Oncol 2004; 22(10): 1849-56.

Warner E., et al., "Surveillance of BRCA1 and BRCA2 mutation carriers with magnetic resonance imaging, ultrasound, mammography, and clinical breast exam," JAMA 2004; 292:1317-1325.

Morris EA, et al., "MR imaging of the breast in patients with occult primary breast carcinoma," Radiology 1997; 205:437-440.

Orel SG, et al., "Suspicious breast lesions: MR imaging with radiologic-pathologic correlation," Radiology 1994; 190:485-493.

Visvanathan K., et al., "American society of clinical oncology clinical practice guideline update on the use of pharmacologic interventions including tamoxifen, raloxifene, and aromatase inhibition for breast cancer risk reduction," J Clin Oncol. Jul. 1, 2009; 27(19):3235-58. Epub May 26, 2009.

Fisher B., et al., "Tamoxifen for prevention of breast cancer: Report of the National Surgical Adjuvant Breast and Bowel Project P-1 Study," JNCI 1998; 90 (18): 1371-88.

Grann VR, et al., "Decision analysis of tamoxifen for the prevention of invasive breast cancer," Cancer J Sci Am 2000; 6:169-178.

Hershman D, et al., "Outcomes of tamoxifen chemoprevention for breast cancer in very high-risk women: A cost-effectiveness analysis," J Clin Oncol 2001; 20:9-16.

Mackarem G., "The effectiveness of the Gail model in estimating risk for development of breast cancer in women under 40 years of age," Breast Journal 2001; 7(1):34-9.

Stojadinovic A., et al., "Electrical Impedance Scanning for the Early Detection of Breast Cancer in Young Women: Preliminary Results of a Multi-Center Prospective Trial," Journal of Clinical Oncology Apr. 20, 2005; 23(12):2703-15.

Livak, K. J., et al., "Analysis of relative gene expression data using real-time quantitative PCR and the 2(-Delta Delta C(T)) Method." Methods 25: 402-408, 2001.

Baloch, Zubair W., et al., The National Cancer Institute Thyroid fine needle aspiration state of the science conference: a summation, CytoJournal Apr. 7, 2008; pp. 1-17, 5:6.

Raza, S. Naweed et al., Risk Factors for Well-Differentiate Thyroid Carcinoma in Patients with Thyroid Nodular Disease, Otolaryngology—Head and Neck Surgery (2008), 139, 21-26.

* cited by examiner

|  | AUC | | PV @ 50% | |
| --- | --- | --- | --- | --- |
|  | Benign | Cancer | Benign | Cancer |
| Test 1 | 71.4% | 71.5% | 60.0% | 66.7% |
| Test 2 | 93.4% | 93.4% | 80.0% | 81.8% |
| Test 3 | 89.2% | 88.7% | 81.3% | 85.7% |
| Test 4 | 89.8% | 89.1% | 81.8% | 66.7% |
| Test 5 | 92.1% | 92.2% | 77.8% | 91.7% |
| Test 6 | 99.8% | 99.8% | 100.0% | 100.0% |
| Test 7 | 76.0% | 76.0% | 80.0% | 80.0% |
| Test 8 | 93.4% | 93.5% | 88.9% | 83.3% |
| Test 9 | 89.8% | 90.5% | 80.0% | 81.8% |
| Test 10 | 88.2% | 88.2% | 70.0% | 91.7% |
| Mean | 88.3% | 88.3% | 80.0% | 82.9% |
| Internal | 88.6% | 89.0% | 81.5% | 82.6% |

FIG. 5

| Probability of case | Drivers | | | Target | |
|---|---|---|---|---|---|
| | Worst EIS | Worst FNA | | Overall Pathology Dx | |
| | | | | Benign | Cancer |
| 0.399% | 1- Definitely Benign | Inadequate | | 100% | 0.0% |
| 0.956% | 2- Probably Benign | Inadequate | | 100% | 0.0% |
| 0.501% | 3- Suspicious for Cancer | Inadequate | | 100% | 0.0% |
| 0.502% | 4- Probably Cancer | Inadequate | | 100% | 0.0% |
| 0.373% | 5- Definitely Cancer | Inadequate | | 100% | 0.0% |
| 4.729% | 1- Definitely Benign | Indeterminate | | 94.3% | 5.7% |
| 12.155% | 2- Probably Benign | Indeterminate | | 87.8% | 12.2% |
| 6.161% | 3- Suspicious for Cancer | Indeterminate | | 90.9% | 9.1% |
| 13.59% | 4- Probably Cancer | Indeterminate | | 41.3% | 58.7% |
| 15.766% | 5- Definitely Cancer | Indeterminate | | 26.4% | 73.6% |
| 1.75% | 1- Definitely Benign | Negative | | 98.9% | 1.1% |
| 4.246% | 2- Probably Benign | Negative | | 97.6% | 2.4% |
| 2.212% | 3- Suspicious for Cancer | Negative | | 98.2% | 1.8% |
| 2.735% | 4- Probably Cancer | Negative | | 79.7% | 20.3% |
| 2.427% | 5- Definitely Cancer | Negative | | 66.7% | 33.3% |
| 0.446% | 1- Definitely Benign | Positive | | 14.9% | 85.1% |
| 2.255% | 2- Probably Benign | Positive | | 7.1% | 92.9% |
| 0.877% | 3- Suspicious for Cancer | Positive | | 9.5% | 90.5% |
| 11.398% | 4- Probably Cancer | Positive | | 0.7% | 99.3% |
| 16.512% | 5- Definitely Cancer | Positive | | 0.4% | 99.6% |

FIG. 8

| Probability Of case | Biomarker (relative-fold change) | | | Dx (% Probability) | |
|---|---|---|---|---|---|
| | LAMC2 | MMP7 | | SF | TG |
| 16.0% | Up to 0.52 | Up to 1.04 | | 99.1 | 0.9 |
| 10.2% | 0.52 to 2.19 | Up to 1.04 | | 91.1 | 8.9 |
| 6.6% | 2.19 plus | Up to 1.04 | | 63.6 | 36.4 |
| 13.3% | Up to 0.52 | 1.04 to 2.77 | | 98.3 | 1.7 |
| 9.0% | 0.52 to 2.19 | 1.04 to 2.77 | | 84.9 | 15.1 |
| 7.0% | 2.19 plus | 1.04 to 2.77 | | 48.9 | 51.1 |
| 5.1% | Up to 0.52 | 2.77 plus | | 73.5 | 26.5 |
| 10.3% | 0.52 to 2.19 | 2.77 plus | | 21.1 | 78.9 |
| 22.5% | 2.19 plus | 2.77 plus | | 4.4 | 95.6 |

FIG. 13

| ACTA2 | ACVR1 | ADM | ALCAM | ANGPT1 | ANGPT2 | ANGPT4 | BAX | BCL2 | BCL2L1 | 18S | 18S |
| --- | --- | --- | --- | --- | --- | --- | --- | --- | --- | --- | --- |
| CAV2 | CCL1 | CCL11 | CCL17 | CCL19 | CCL2 | CCL20 | CCL22 | CCL25 | CCL27 | CCL28 | CCL3 |
| COL3A1 | COL4A1 | COL4A3 | CSF1 | CSF2 | CSF3 | CTGF | CX3CL1 | CXCL1 | CXCL10 | CXCL11 | CXCL12 |
| FGF10 | FGF11 | FGF12 | FGF13 | FGF17 | FGF2 | FGF3 | FGF5 | FGF7 | FGF8 | FGF9 | FIGF |
| IFNG | IGF1 | IGF2 | IGFBP1 | IGFBP2 | IGFBP3 | IGFBP4 | IGFBP5 | IGFBP6 | IGFBP7 | IL10 | IL11 |
| IL6 | IL7 | IL8 | IL9 | ITGA5 | ITGAL | ITGAM | ITGB2 | KDR | KITLG | LBP | LTA |
| MMP7 | MMP8 | MMP9 | MPO | NCAM2 | NFKB1 | NFKB2 | NOS2A | OSMR | PDGFA | PDGFB | PECAM1 |
| SMAD6 | SMAD7 | SOCS1 | SOCS3 | SOCS5 | STAT3 | TEK | TGFA | TGFB1 | TGFB2 | TGFB3 | TGFBR1 |
| BCL2L2 | BMP1 | BMP15 | BMP3 | BMP4 | BMP5 | BMP6 | BMP7 | BMP8B BMP8A | CALCA | CALCB | CAV1 |
| CCL4 CCL4L1 CCL4L2 | CCL5 | CCL7 | CD14 | CD4 | CD40 | CD40LG | CD83 | CD8A | CD8B | COL18A1 | COL1A1 |
| CXCL13 | CXCL2 | CXCL5 | CXCL9 | ECGF1 | EDN1 | EGF | EGR1 | EPO | FADD | FAS | FGF1 |
| FLT1 | FN1 | GAPDH | GDF3 | GDF5 | MSTN | GDF9 | HGF | HMGB1 | IAPP | ICAM2 | IFNB1 |
| IL12A | IL13 | IL15 | IL16 | IL17A | IL18 | IL1A | IL1B | IL2 | IL3 | IL4 | IL5 |
| MAPK14 | MET | MMP1 | MMP10 | MMP11 | MMP12 | MMP13 | MMP14 | MMP15 | MMP2 | MMP24 | MMP3 |
| PF4 | PLA2G4A | PTGS1 | PTGS2 | SELE | SELP | SERPINE1 | SLPI | SMAD1 | SMAD2 | SMAD3 | SMAD4 |
| TIE1 | TIMP1 | TIMP2 | TIMP3 | TNC | TNF | TNFSF10 | VCAM1 | VEGFA | VEGFB | VEGFC | XCL1 XCL2 |

| Protein Quantitation | RNA Quantitation | Gene Name |
|---|---|---|
| | 18s (card 1) | Eukaryotic 18S rRNA |
| | 18s (card 2) | Eukaryotic 18S rRNA |
| | ACTA2 | actin, alpha 2, smooth muscle, aorta |
| | ACVR1 | activin A receptor, type I |
| | ALCAM | activated leukocyte cell adhesion molecule |
| | ANGPT1 | angiopoietin 1 |
| | ANGPT2 | angiopoietin 2 |
| | ANGPT4 | angiopoietin 4 |
| | BAX | BCL2-associated X protein |
| | BCL2 | B-cell CLL/lymphoma 2 |
| | BCL2L1 | BCL2-like 1 |
| | BCL2L2 | BCL2-like 2 |
| | BMP1 | bone morphogenetic protein 1 |
| | BMP15 | bone morphogenetic protein 15 |
| | BMP3 | bone morphogenetic protein 3 (osteogenic) |
| | BMP4 | bone morphogenetic protein 4 |
| | BMP5 | bone morphogenetic protein 5 |
| | BMP6 | bone morphogenetic protein 6 |
| | BMP7 | bone morphogenetic protein 7 (osteogenic protein 1) |
| | BMP8B | bone morphogenetic protein 8b (osteogenic protein 2) |
| | CAV1 | caveolin 1, caveolae protein, 22kDa |
| | CAV2 | caveolin 2 |
| | CCL1 | chemokine (C-C motif) ligand 1 |
| Eotaxin (CCL11; eosinophils chemotaxis; receptors are CCR2, CCR3, and CCR5 on eosinophils) | CCL11 | chemokine (C-C motif) ligand 11 |

FIG. 15B

| | | |
|---|---|---|
| MCP-1 (CCL2; monocyte chemotactic protein-1; regulates expression of cytokines iL1 and IL6) | CCL17 | chemokine (C-C motif) ligand 17 |
| | CCL19 | chemokine (C-C motif) ligand 19 |
| | CCL2 | chemokine (C-C motif) ligand 2 |
| | CCL20 | chemokine (C-C motif) ligand 20 |
| | CCL22 | chemokine (C-C motif) ligand 22 |
| | CCL25 | chemokine (C-C motif) ligand 25 |
| | CCL27 | chemokine (C-C motif) ligand 27 |
| | CCL28 | chemokine (C-C motif) ligand 28 |
| MIP-1a (CCL3;macrophage inflammatory protein-1-alpha) | CCL3 | chemokine (C-C motif) ligand 3 |
| | CCL4;CCL4L1; CCL4L2 | chemokine (C-C motif) ligand 4;chemokine (C-C motif) ligand 4-like 1;chemokine (C-C motif) ligand 4-like 2 |
| RANTES (CCL5; Regulated upon Activation, Normal T-cell Expressed, and Secreted) | CCL5 | chemokine (C-C motif) ligand 5 |
| | CCL7 | chemokine (C-C motif) ligand 7 |
| | CD14 | CD14 molecule |
| | CD4 | CD4 molecule |
| | CD40 | CD40 molecule, TNF receptor superfamily member 5 |
| | CD40LG | CD40 ligand (TNF superfamily, member 5, hyper-IgM syndrome) |
| | CD83 | CD83 molecule |
| | CD8A | CD8a molecule |
| | CD8B | CD8b molecule |
| | COL18A1 | collagen, type XVIII, alpha 1 |
| | COL1A1 | collagen, type I, alpha 1 |
| | COL3A1 | collagen, type III, alpha 1 (Ehlers-Danlos syndrome type IV, autosomal dominant) |

FIG. 15C

| | | |
|---|---|---|
| | COL4A1 | collagen, type IV, alpha 1 |
| | COL4A3 | collagen, type IV, alpha 3 (Goodpasture antigen) |
| | CSF1 (identical to M-CSF) | colony stimulating factor 1 (macrophage) |
| GM-CSF (Identical with CSF-alpha, -beta, CSF-2) | CSF2 | colony stimulating factor 2 (granulocyte-macrophage) |
| | CSF3 | colony stimulating factor 3 (granulocyte) |
| | CTGF | connective tissue growth factor |
| | CX3CL1 | chemokine (C-X3-C motif) ligand 1 |
| | CXCL1 | chemokine (C-X-C motif) ligand 1 (melanoma growth stimulating activity, alpha) |
| IP-10 (CXCL10; INF-inducible protein-10; receptor is CXCR3) | CXCL10 | chemokine (C-X-C motif) ligand 10 |
| | CXCL11 | chemokine (C-X-C motif) ligand 11 |
| | CXCL12 | chemokine (C-X-C motif) ligand 12 (stromal cell-derived factor 1) |
| | CXCL13 | chemokine (C-X-C motif) ligand 13 (B-cell chemoattractant) |
| | CXCL2 | chemokine (C-X-C motif) ligand 2 |
| | CXCL5 | chemokine (C-X-C motif) ligand 5 |
| | CXCL9 | chemokine (C-X-C motif) ligand 9 |
| | ECGF1 | endothelial cell growth factor 1 (platelet-derived) |
| | EDN1 | endothelin 1 |
| | EGF | epidermal growth factor (beta-urogastrone) |
| | EGR1 | early growth response 1 |
| | EPO | erythropoietin |
| | FADD | Fas (TNFRSF6)-associated via death domain |

FIG. 15D

| | |
|---|---|
| FAS | Fas (TNF receptor superfamily, member 6) |
| FGF1 | fibroblast growth factor 1 (acidic) |
| FGF10 | fibroblast growth factor 10 |
| FGF11 | fibroblast growth factor 11 |
| FGF12 | fibroblast growth factor 12 |
| FGF13 | fibroblast growth factor 13 |
| FGF14 | fibroblast growth factor 14 |
| FGF17 | fibroblast growth factor 17 |
| FGF2 | fibroblast growth factor 2 (basic) |
| FGF3 | fibroblast growth factor 3 (murine mammary tumor virus integration site (v-int-2) oncogene homolog) |
| FGF4 | fibroblast growth factor 4 (heparin secretory transforming protein 1, Kaposi sarcoma oncogene) |
| FGF5 | fibroblast growth factor 5 |
| FGF7 | fibroblast growth factor 7 (keratinocyte growth factor) |
| FGF8 | fibroblast growth factor 8 (androgen-induced) |
| FGF9 | fibroblast growth factor 9 (glia-activating factor) |
| FIGF | c-fos induced growth factor (vascular endothelial growth factor D) |
| FLT1 | fms-related tyrosine kinase 1 (vascular endothelial growth factor/vascular permeability factor receptor) |
| FN1 | fibronectin 1 |
| GAPDH (card1) | glyceraldehyde-3-phosphate dehydrogenase |
| GAPDH (card2) | glyceraldehyde-3-phosphate dehydrogenase |

FIG. 15E

| | | |
|---|---|---|
| | GDF2 | growth differentiation factor 2 |
| | GDF3 | growth differentiation factor 3 |
| | GDF5 | growth differentiation factor 5 (cartilage-derived morphogenetic protein-1) |
| | GDF8 | growth differentiation factor 8 |
| | GDF9 | growth differentiation factor 9 |
| | HGF | hepatocyte growth factor (hepapoietin A; scatter factor) |
| | HMGB1 | high-mobility group box 1 |
| | ICAM2 | intercellular adhesion molecule 2 |
| | IFNB1 | interferon, beta 1, fibroblast |
| IFNγ | IFNG | interferon, gamma |
| | IGF1 | insulin-like growth factor 1 (somatomedin C) |
| | IGF2 | insulin-like growth factor 2 (somatomedin A) |
| | IGFBP1 | insulin-like growth factor binding protein 1 |
| | IGFBP2 | insulin-like growth factor binding protein 2, 36kDa |
| | IGFBP3 | insulin-like growth factor binding protein 3 |
| | IGFBP4 | insulin-like growth factor binding protein 4 |
| | IGFBP5 | insulin-like growth factor binding protein 5 |
| | IGFBP6 | insulin-like growth factor binding protein 6 |
| | IGFBP7 | insulin-like growth factor binding protein 7 |
| IL-10 | IL10 | interleukin 10 |
| | IL11 | interleukin 11 |
| IL-12(p40) IL-12(p70) | IL12A | interleukin 12A (natural killer cell stimulatory factor 1, cytotoxic lymphocyte maturation factor 1, p35) |
| IL-13 | IL13 | interleukin 13 |
| IL-15 | IL15 | interleukin 15 |
| | IL16 | interleukin 16 (lymphocyte chemoattractant factor) |

FIG. 15F

| | | |
|---|---|---|
| | IL17A | interleukin 17A |
| | IL18 | interleukin 18 (interferon-gamma-inducing factor) |
| IL-1a | IL1A | interleukin 1, alpha |
| IL-1B | IL1B | interleukin 1, beta |
| IL-2 | IL2 | interleukin 2 |
| IL-3 | IL3 | interleukin 3 (colony-stimulating factor, multiple) |
| IL-4 | IL4 | interleukin 4 |
| IL-5 | IL5 | interleukin 5 (colony-stimulating factor, eosinophil) |
| IL-6 | IL6 | interleukin 6 (interferon, beta 2) |
| IL-7 | IL7 | interleukin 7 |
| IL-8 | IL8 | interleukin 8 |
| | IL9 | interleukin 9 |
| | ITGA5 | integrin, alpha 5 (fibronectin receptor, alpha polypeptide) |
| | ITGAL | integrin, alpha L (antigen CD11A (p180), lymphocyte function-associated antigen 1; alpha polypeptide) |
| | ITGAM | integrin, alpha M (complement component 3 receptor 3 subunit) |
| | ITGB2 | integrin, beta 2 (complement component 3 receptor 3 and 4 subunit) |
| | KDR | kinase insert domain receptor (a type III receptor tyrosine kinase) |
| | KITLG | KIT ligand |
| | LBP | lipopolysaccharide binding protein |
| | LTA | lymphotoxin alpha (TNF superfamily, member 1) |
| | MAPK14 | mitogen-activated protein kinase 14 |

FIG. 15G

| | | |
|---|---|---|
| | MET | met proto-oncogene (hepatocyte growth factor receptor) |
| | MMP1 | matrix metallopeptidase 1 (interstitial collagenase) |
| | MMP10 | matrix metallopeptidase 10 (stromelysin 2) |
| | MMP11 | matrix metallopeptidase 11 (stromelysin 3) |
| | MMP12 | matrix metallopeptidase 12 (macrophage elastase) |
| MMP-13 | MMP13 | matrix metallopeptidase 13 (collagenase 3) |
| | MMP14 | matrix metallopeptidase 14 (membrane-inserted) |
| | MMP15 | matrix metallopeptidase 15 (membrane-inserted) |
| MMP-2 | MMP2 | matrix metallopeptidase 2 (gelatinase A, 72kDa gelatinase, 72kDa type IV collagenase) |
| | MMP24 | matrix metallopeptidase 24 (membrane-inserted) |
| MMP-3 | MMP3 | matrix metallopeptidase 3 (stromelysin 1, progelatinase) |
| MMP-7 | MMP7 | matrix metallopeptidase 7 (matrilysin, uterine) |
| | MMP8 | matrix metallopeptidase 8 (neutrophil collagenase) |
| MMP-9 | MMP9 | matrix metallopeptidase 9 (gelatinase B, 92kDa gelatinase, 92kDa type IV collagenase) |
| | MPO | myeloperoxidase |
| | NCAM2 | neural cell adhesion molecule 2 |
| | NFKB1 | nuclear factor of kappa light polypeptide gene enhancer in B-cells 1 (p105) |

FIG. 15H

| | |
|---|---|
| NFKB2 | nuclear factor of kappa light polypeptide gene enhancer in B-cells 2 (p49/p100) |
| NOS2A | nitric oxide synthase 2A (inducible, hepatocytes) |
| OSMR | oncostatin M receptor |
| PDGFA | platelet-derived growth factor alpha polypeptide |
| PDGFB | platelet-derived growth factor beta polypeptide (simian sarcoma viral (v-sis) oncogene homolog) |
| PECAM1 | platelet/endothelial cell adhesion molecule (CD31 antigen) |
| PF4 | platelet factor 4 (chemokine (C-X-C motif) ligand 4) |
| PLA2G4A | phospholipase A2, group IVA (cytosolic, calcium-dependent) |
| PTGS1 | prostaglandin-endoperoxide synthase 1 (prostaglandin G/H synthase and cyclooxygenase) |
| PTGS2 | prostaglandin-endoperoxide synthase 2 (prostaglandin G/H synthase and cyclooxygenase) |
| SELE (CD62-E) | selectin E (endothelial adhesion molecule 1) |
| SELP (CD62-P) | selectin P (granule membrane protein 140kDa, antigen CD62) |
| SERPINE1 | serpin peptidase inhibitor, clade E (nexin, plasminogen activator inhibitor type 1), member 1 |
| SLPI | secretory leukocyte peptidase inhibitor |
| SMAD1 | SMAD, mothers against DPP homolog 1 (Drosophila) |

FIG. 15l

| | |
|---|---|
| SMAD2 | SMAD, mothers against DPP homolog 2 (Drosophila) |
| SMAD3 | SMAD, mothers against DPP homolog 3 (Drosophila) |
| SMAD4 | SMAD, mothers against DPP homolog 4 (Drosophila) |
| SMAD6 | SMAD, mothers against DPP homolog 6 (Drosophila) |
| SMAD7 | SMAD, mothers against DPP homolog 7 (Drosophila) |
| SOCS1 | suppressor of cytokine signaling 1 |
| SOCS3 | suppressor of cytokine signaling 3 |
| SOCS5 | suppressor of cytokine signaling 5 |
| STAT3 | signal transducer and activator of transcription 3 (acute-phase response factor) |
| TEK | TEK tyrosine kinase, endothelial (venous malformations, multiple cutaneous and mucosal) |
| TGFA | transforming growth factor, alpha |
| TGFB1 | transforming growth factor, beta 1 (Camurati-Engelmann disease) |
| TGFB2 | transforming growth factor, beta 2 |
| TGFB3 | transforming growth factor, beta 3 |
| TGFBR1 | transforming growth factor, beta receptor I (activin A receptor type II-like kinase, 53kDa) |
| TIE1 | tyrosine kinase with immunoglobulin-like and EGF-like domains 1 |
| TIMP1 | TIMP metallopeptidase inhibitor 1 |
| TIMP2 | TIMP metallopeptidase inhibitor 2 |
| TIMP3 | TIMP metallopeptidase inhibitor 3 (Sorsby fundus dystrophy, pseudoinflammatory) |

| | | |
|---|---|---|
| TNFa | TNC | tenascin C (hexabrachion) |
| | TNF | tumor necrosis factor (TNF superfamily, member 2) |
| | TNFSF10 | tumor necrosis factor (ligand) superfamily, member 10 |
| | VCAM1 | vascular cell adhesion molecule 1 |
| | VEGF | vascular endothelial growth factor |
| | VEGFB | vascular endothelial growth factor B |
| | VEGFC | vascular endothelial growth factor C |
| | XCL1;XCL2 | chemokine (C motif) ligand 1;chemokine (C motif) ligand 2 |
| | ADM | adrenomedullin |
| | CALCA | calcitonin/calcitonin-related polypeptide, alpha |
| | CALCB | calcitonin-related polypeptide, beta |
| | IAPP | islet amyloid polypeptide |

FIG. 15J

| | No. of Wounds N=29 | Normal Healing n=20 (69%) | Impaired Healing n=9 (31%) | p= |
|---|---|---|---|---|
| Age (years) † | | 23 ±5 | 21 ±2 | 0.66 |
| Gender (%) | | | | NA |
| Male | 29 (100%) | 20 (69%) | 9 (31%) | |
| Female | 0 | | | |
| Body Mass Index † | | 25.9 ±4.5 | 22.0 ±3.7 | 0.42 |
| Tobacco use (%) | 7 (24%) | 4 (57%) | 3 (43%) | 0.65 |
| Injury Severity Score † | | 20 ±11 | 39 ±7 | 0.001 |
| Traumatic Brain Injury (%) | 8 (28%) | 5 (63%) | 3 (37%) | 0.66 |
| Mechanism of injury (%) | | | | 0.25 |
| GSW | 2 (7%) | 2 (100%) | 0 | |
| Blast | 26 (90%) | 18 (69%) | 8 (31%) | |
| Crush | 1 (3%) | 0 | 1 (100%) | |
| Wound location (%) | | | | 0.20 |
| Upper extremity | 9 (31%) | 8 (89%) | 1 (11%) | |
| Lower extremity | 20 (69%) | 12 (60%) | 8 (40%) | |
| Traumatic amputation (%) | 11 (38%) | 7 (64%) | 4 (36%) | 0.69 |
| Size of wound (cm$^3$) † | | 192 ±276 | 583 ±673 | 0.03 |
| Associated vascular injury (%) | 7 (24%) | 2 (29%) | 5 (71%) | 0.016 |
| Wound closure method (%) | | | | 0.40 |
| Suture | 20 (69%) | 15 (75%) | 5 (25%) | |
| Skin Graft | 9 (31%) | 5 (56%) | 4 (44%) | |

† Mean ±SD

FIG. 16

| Characteristic | | Age Category (years) | | | | P-value Chi-Square |
|---|---|---|---|---|---|---|
| | | <30 | 30-34 | 35-39 | 40-49 | |
| Menopausal Status | | | | | | <0.001 |
| | Pre-menopausal | 124 | 114 | 122 | 171 | |
| | Post-menopausal | 0 | 5 | 15 | 34 | |
| | Peri-menopausal | 0 | 0 | 1 | 4 | |
| | Not Recorded | 0 | 0 | 1 | 0 | |
| Screening Breast EIS Result | | | | | | 0.4515 |
| | Negative | 120 | 117 | 132 | 199 | |
| | Positive | 4 | 2 | 7 | 10 | |
| Clinical Breast Exam Result | | | | | | 0.0077 |
| | No Findings | 78 | 88 | 77 | 141 | |
| | Not Suspicious | 45 | 28 | 52 | 57 | |
| | Suspicious | 1 | 3 | 10 | 11 | |
| Hormone Replacement Therapy | | | | | | 0.0263 |
| | Current | 0 | 2 | 2 | 11 | |
| | Past | 0 | 1 | 0 | 3 | |
| | Never | 124 | 116 | 137 | 195 | |
| Mammogram Results | | | | | | <0.001 |
| | BIRADS 0 | 1 | 0 | 3 | 10 | |
| | BIRADS I or II | 6 | 16 | 61 | 109 | |
| | BIRADS III | 1 | 6 | 8 | 21 | |
| | BIRADS IV | 0 | 2 | 10 | 23 | |
| | BIRADS V | 0 | 1 | 2 | 1 | |
| | No mammogram | 116 | 94 | 55 | 45 | |
| Breast Biopsy Category | | | | | | 0.4076 |
| | Benign No Atypia | 19 | 12 | 27 | 34 | |
| | Premalignant | 1 | 0 | 2 | 4 | |
| | Infiltrating Cancer or DCIS | 0 | 1 | 2 | 3 | |
| | No biopsy (Assumed Benign) | 104 | 106 | 108 | 168 | |
| Family History Category | | | | | | 0.4080 |
| | One 1st Degree | 9 | 12 | 20 | 18 | |
| | One 2nd Degree | 22 | 24 | 24 | 38 | |
| | One 1st and one or more 2nd | 9 | 9 | 12 | 11 | |
| | Two or more 1st Degree | 0 | 1 | 4 | 2 | |
| | Two or more 2nd Degree | 7 | 12 | 10 | 21 | |
| | No Significant Family History | 77 | 61 | 69 | 119 | |
| Gail Model 5-year Risk Category | | | | | | <0.001 |
| | <1.66% | 108 | 119 | 132 | 175 | |
| | ≥1.66% | 0 | 0 | 3 | 27 | |

FIG. 22

| Characteristic | Biopsy Category | | | | |
|---|---|---|---|---|---|
| *p-value of cancer and pre-malignant populations compared to benign population | Benign No Atypia | Infiltrating Cancer or DCIS | Pre-malignant | No biopsy (Benign) | P-value Chi-Square |
| Mean age at menarche (years)* | 13 | 12 | 13 | 13 | 0.9997 |
| Mean age at 1st Pregnancy (years)* | 25 | 22 | 24 | 24 | 0.8622 |
| % Nulliparous | 79.1% | 100.0% | 66.7% | 75.8% | 0.9299 |
| Mean age at diagnosis (years)* | 36 | 38 | 38 | 35 | 0.0959 |
| Menopausal Status | | | | | 0.0307 |
| Pre-menopausal | 86 | 6 | 6 | 433 | |
| Post-menopausal | 6 | 0 | 0 | 48 | |
| Peri-menopausal | 0 | 0 | 1 | 4 | |
| Screening Breast EIS Result | | | | | <0.001 |
| Negative | 87 | 4 | 4 | 473 | |
| Positive | 5 | 2 | 3 | 13 | |
| Clinical Breast Exam Result | | | | | <0.001 |
| No Findings | 19 | 2 | 4 | 359 | |
| Not Suspicious | 55 | 1 | 2 | 124 | |
| Suspicious | 18 | 3 | 1 | 3 | |
| Hormone Replacement Therapy | | | | | 0.9460 |
| Current | 1 | 0 | 0 | 14 | |
| Past | 1 | 0 | 0 | 3 | |
| Never | 90 | 6 | 7 | 469 | |
| Bra Cup Size | | | | | 0.0094 |
| A | 4 | 3 | 0 | 39 | |
| B | 25 | 1 | 3 | 123 | |
| C | 18 | 0 | 1 | 110 | |
| D+ | 6 | 1 | 1 | 65 | |
| Not Recorded | 39 | 1 | 2 | 149 | |
| Mammogram Results | | | | | <0.001 |
| BIRADS 0 | 3 | 0 | 3 | 8 | |
| BIRADS I or II | 27 | 0 | 2 | 163 | |
| BIRADS III | 6 | 0 | 0 | 30 | |
| BIRADS IV | 26 | 3 | 2 | 4 | |
| BIRADS V | 0 | 3 | 0 | 1 | |
| No mammogram | 30 | 0 | 0 | 280 | |
| Family History Category | | | | | 0.1035 |
| One 1st Degree | 7 | 1 | 0 | 51 | |
| One 2nd Degree | 18 | 1 | 2 | 87 | |
| One 1st and one or more $2^{nd}$ | 0 | 1 | 0 | 6 | |
| Two or more 1st Degree | 6 | 0 | 2 | 42 | |
| Two or more 2nd Degree | 55 | 2 | 3 | 266 | |
| No Significant Family History | 6 | 1 | 0 | 34 | |
| Gail Model 5-year Risk Category | | | | | <0.001 |
| <1.66% | 86 | 2 | 5 | 441 | |
| >/=1.66% | 4 | 3 | 1 | 22 | |
| Not Recorded | 2 | 1 | 1 | 23 | |

FIG. 23

|  | AUC | | | PV | | |
|---|---|---|---|---|---|---|
| Internal | Benign | Cancer | Premalignant | Benign | Cancer | Premalignant |
|  | 0.98 | 0.98 | 0.97 | 100.0% | 66.7% | 50.0% |
| Exercise 1 | 0.94 | 0.98 | 0.58 | 100.0% | 33.3% | 0.0% |
| Exercise 2 | 0.81 | 0.98 | 0.53 | 94.4% | NA | 0.0% |
| Exercise 3 | 0.92 | 0.98 | 0.90 | 93.8% | 33.3% | 0.0% |
| Exercise 4 | 0.89 | 0.95 | 0.95 | 100.0% | 50.0% | 16.7% |
| Exercise 5 | 0.86 | 0.98 | 0.79 | 94.4% | 50.0% | NA |
| Mean | 0.88 | 0.97 | 0.75 | 96.5% | 41.7% | 4.2% |
| 95% CI Low | 0.82 | 0.96 | 0.51 | 92.6% | 26.4% | 0.0% |
| 95% CI High | 0.95 | 0.99 | 0.98 | 100.0% | 57.0% | 17.4% |

FIG. 25

| Case Frequency | Known Evidence | | Estimated Outcome | | |
|---|---|---|---|---|---|
| | EIS Result | Gail Cutoff | Benign No Atypia | Infil Cancer or DCIS | Premalignant |
| 74% | Negative | Negative | 91% | 3% | 7% |
| 16% | Positive | Negative | 65% | 9% | 26% |
| 7% | Negative | Positive | 53% | 27% | 19% |
| 3% | Positive | Positive | 18% | 45% | 37% |

FIG. 27

BAYESIAN CLINICAL DECISION MODEL FOR DETERMINING PROBABILITY OF TRANSPLANT GLOMERULOPATHY

This application is a continuation of PCT Application No. PCT/US2009/060850, filed on Oct. 15, 2009, which claimed the benefit of U.S. Patent Application No. 61/105,786 filed Oct. 15, 2008 and U.S. Patent Application No. 61/166,245 filed Apr. 2, 2009, which are hereby incorporated by reference. The International Application No. PCT/US2009/060850 was published on Apr. 22, 2010.

I. FIELD OF THE INVENTION

The present invention relates to a model for providing a patient-specific diagnosis of disease using clinical data. More particularly, the present invention relates to a fully unsupervised, machine-learned, cross-validated, and dynamic Bayesian Belief Network model that utilizes clinical parameters for determining a patient-specific probability of transplant glomerulopathy.

II. BACKGROUND OF THE INVENTION

Within this application several publications are referenced by arabic numerals within brackets. Full citations for these, and other, publications may be found at the end of the specification immediately preceding the claims. The disclosures of all these publications in their entireties are hereby expressly incorporated by reference into the present application for the purposes of indicating the background of the present invention and illustrating the state of the art.

Thyroid nodules represent a common problem brought to medical attention. Four to seven percent of the United States adult population (10-18 million) has palpable thyroid nodules, and up to 50% of American women older than age 50 have nodules visible by thyroid ultrasound [1]. The majority (>95%) of thyroid nodules are benign; however, malignancy risk increases with male gender, nodule size, rapid growth and associated symptoms, extremes of age (<30 and >60 years), underlying autoimmune disease (e.g. Graves' Disease), nodule growth under thyroid hormone suppression, personal or family history of thyroid malignancy, and radiation exposure [2].

Thorough history and physical examination, serum thyrotropin (TSH) level, thyroid ultrasound, and fine need aspiration biopsy (FNAB) are utilized to evaluate patients with thyroid nodules. Patients with thyroid nodules and normal or elevated serum TSH typically undergo thyroid ultrasound to determine if FNAB is warranted. Nodules with a maximum diameter greater than 1.0-1.5 cm with solid elements, or nodules of any size demonstrating suspicious features on ultrasound should undergo FNAB [3]. Given the increased risk of malignancy in thyroid incidentalomas detected by 18FDG-PET (Fluorodeoxyglucose or Fludeoxyglucose positron emission tomography) (14-50%) or sestamibi scan (22-66%), FNAB is indicated under these circumstances [4, 5]. Functioning thyroid nodules (suppressed TSH, hyperfunctioning on radionuclide scan) do not require FNAB in the absence of clinically suspicious findings.

Fine needle aspiration biopsy is a cost effective and accurate diagnostic tool for thyroid nodules. In experienced hands, the sensitivity and specificity of FNAB are very high, 95% and 99%, respectively, in positive and negative cases [6]. A six tiered classification system for FNAB is favored that is associated with increased risk of malignancy across the spectrum of: unsatisfactory or non-diagnostic specimen (unknown), benign (<1%), follicular lesion (atypia) of undetermined significance (5-10%), follicular neoplasm (20-30%), suspicious for malignancy (50-75%), and malignant (100%) [3]. Over 20% of patients undergoing FNAB of a thyroid nodule have indeterminate cytology (follicular neoplasm), and they require and are exposed to the function-limiting complications (impaired voice and swallowing) of thyroid lobectomy/isthmusectomy conducted purely for the purpose of attaining a more definitive diagnosis. Given that the majority of patients with follicular neoplasms have benign surgical pathology, thyroidectomy in these patients is conducted principally with diagnostic intent [7]. Electrical impedance scanning (EIS) is another tool for scanning thyroid nodules [9, 10]. Utilization of EIS can result in a significant reduction (67%) in the number of purely diagnostic thyroid resections for follicular neoplasms [8, 9].

Fine needle aspiration cytology has a high diagnostic accuracy and is a practicable test for the initial evaluation of thyroid nodules. However, the efficacy of FNA for the differential diagnosis of follicular and Hurthle cell neoplasms remains imperfect. As the majority of detected thyroid nodules are benign and cytology, even in the best of hands, is indeterminate in 20% of fine needle aspirates, the frequency of diagnostic or non-therapeutic thyroid resection is increasing.

As the majority of patients with indeterminate FNA cytology have benign nodules, surgical operations are undertaken primarily with diagnostic intent. Thus, it is difficult to non-invasively differentiate benign and clinically inconsequential low-risk malignant nodules from those that indeed stand to benefit from resection. Color Doppler sonography with quantitative analysis of tumor vascularity, in conjunction with conventional ultrasonographic assessment of echogenicity, halo, microcalcifications, and tumor size, may provide a means for differentiating malignant from benign solid thyroid nodules in the pre-operative setting [11-14]. However, the predictive value of this combined technique is achieved by compromising diagnostic sensitivity [15]. The predictive value of ultrasonography may be enhanced significantly through the application of ultrasound thyroid elastography [16-17]. The application of 18F-FDG PET shows high sensitivity for the diagnosis of malignancy in thyroid nodules demonstrating indeterminate cytology on pre-operative FNA. However, the low specificity of the technique limits its utility [18-19].

Cellular changes alter the flow of electrical current through living tissue, and differences in cellular electrical signature between malignant and non-malignant tissue has been identified and studied extensively since the 1920's [20]. EIS devices measure tissue impedance characteristics and identify irregularities in conductance and capacitance that are associated with increased levels of cellular activity and malignant transformation [21]. EIS measurements are obtained by introducing a known, low-level, biocompatible, alternating current to the body via a hand-held electrical signal generator. The signal is directed through the measured tissue and collected via a non-invasive surface probe. EIS is safe, feasible, and diagnostically accurate in detecting differences in the bioelectrical signature of benign and malignant tissue through body surface measurements of suspicious skin lesions and lymph nodes, and breast abnormalities [22-30]. EIS is a safe, rapid, realtime, and non-invasive imaging modality with a predictive value sufficient to make it an adjunct to FNA, particularly in the setting of indeterminate cytology [8, 9].

Recognizing that individual variables, though independently associated with thyroid cancer, are insufficient in predicting the risk of malignancy in any given thyroid nodule, multivariate predictive algorithms have been developed to determine the cumulative risk of malignancy for this clinical problem [10, 31]. One predictive algorithm utilizes a multivariate stepwise regression model to predict malignancy in thyroid nodules in a highly selected patient population on the basis of patient age, calcifications in a sonographically solid nodule, and FNAB cytology [10]. Another predictive algorithm applies multivariate modeling in patients with indeterminate thyroid nodules to define male gender, nodule size exceeding 4 cm, and character of the gland by palpation (dominant nodule in multi-nodular goiter) to predict the risk of thyroid malignancy [31]. The development of this predictive algorithm was limited to a narrow population of patients with follicular neoplasia by FNAB, and did not include imaging-based variables according to standard of practice in the predictive model.

Many electronic clinical decision support systems have been developed that rely on human expertise to develop decision-support rules rather than calculating a specific estimate of outcome using historical source data. Such "expert systems" take two forms. The first form is a system where clinical experts, following a systematic review of the literature, devise a system of static decision making rules for clinical decision support. The second form is a system where clinicians in the treating facility, usually basing their judgments on personal experience and the literature, devise a set of rules for clinical decision making in their own institution. The rules developed under both systems can either be implemented in publication format, in the form of published guidelines, or as a set of static decision rules in a clinical informatics system.

Transplant glomerulopathy (TG) is another disease that is difficult to diagnose. Transplant glomerulopathy is a distinctive lesion identified histologically on allograft biopsy and is associated with rapid decline in glomerular filtration rate and poor outcome. It is defined by a characteristic doubling of the glomerular basement membrane as well as increasing evidence that supports an immunologic pathogenesis; however, the molecular pathways involved have not been elucidated. Currently, transplant glomerulopathy must be diagnosed by microscopy, whether light or electron, at a minimum and thus necessitates an advanced disease stage, for which there is no cure.

Long-term kidney allograft function continues to improve modestly, despite dramatic improvements in acute rejection rates and short term patient and graft survivals. Measurement of serum creatinine is typically the primary monitoring modality following kidney transplantation. Significant changes in serum creatinine, and/or the development of proteinuria, result in a series of maneuvers to define the many potential etiologies of acute and chronic allograft dysfunction. Allograft biopsy is the current standard of these maneuvers, although morphologic analysis may not easily distinguish these etiologies. Furthermore, the analysis may be limited in regards to prognostic importance and functional outcome.

Gene expression analysis using microarrays and real-time polymerase chain reaction (PCR) has been applied broadly in the field of renal transplantation. Gene expression changes found in renal biopsies, urine sediment, and peripheral white blood cells have been used to evaluate allografts with stable function, acute rejection, and chronic allograft dysfunction. In addition, gene expression within the renal allograft pre-reperfusion or reperfusion periods has been correlated with delayed graft function and medium term allograft survival.

Several well-established relationships support that such an approach to identifying TG has biologic relevance. The relationship between pathology and cell signaling (chemokine expression), cell trafficking (adhesion molecule expression) and tissue remodeling (MMP expression) is supported by current models of TG. TG is believed to be secondary to binding of donor specific antibodies to endothelium with resulting stimulation and recruiting of secondary mediators leading to an inflammatory response. This inflammatory response and subsequent tissue injury has been associated with chemokine, adhesion molecule and MMP expression. Additionally, adhesion molecule expression has been shown to be associated with both chronic disease and stable function in renal transplant recipients. Alteration of chemokine expression has been linked to costimulatatory molecules (CD28, 40L, 80, 86) and IL-10 has been demonstrated to be elevated in allografts with stable function. The development of TG and Cd4 expression has also been well characterized.

The majority of modern war wounds are caused by blasts and high-energy ballistics [32-34]. Complex traumatic wounds require aggressive surgical care, including serial debridements to remove devitalized tissue and decrease bacterial load. Positive-pressure irrigation, negative-pressure and vacuum-assisted closure (VAC) have improved wound management [35-36]. However, despite these technological advances, the basic surgical decision regarding appropriate timing of surgical traumatic wound closure or coverage remains very subjective.

Poorly defined pathophysiology of acute wound failure partially contributes to the difficulties of objectively assessing wound healing. Current criteria for wound closure or coverage consider many subjective factors, which include the patient's general condition, injury location, adequacy of perfusion, and the gross appearance of the wound. Factors used to assess the patient's general condition include nutritional and nonspecific systemic inflammatory parameters. Relevance of injury location and visual assessment of the wound, such as the appearance of granulation tissue, are subjectively determined by the surgeon. Thus, there is considerable intra-observer variability in wound assessment. Furthermore, the decision making process used to make wound closure determination are ill-defined. After evaluating these factors, surgeons often reach a wound status determination base on his/her experience and discretion. Therefore, even in the hands of seasoned surgeons, some wounds ultimately fail. Unfortunately, other wounds with the biologic ability to heal will undergo unnecessary surgical debridements, adding treatment costs and exposing patients to additional anesthetic and surgical morbidity risk. Objective criteria and decision algorithms to define the appropriate timing of wound closure are needed.

The molecular landscape of the wound ultimately determines the fate of the wound healing process. Acute wounds typically heal by an interdependent sequence of events mediated by inflammatory messengers. The wound healing process generally has three phases. They are the inflammatory phase, the proliferative phase, and the maturational phase (or remodeling phase). The inflammatory phase is characterized by hemostasis and inflammation and typically lasts one to three days. After injury to tissue occurs, damaged cell membranes immediately release thromboxane A2 and prostaglandin 2-alpha, potent vasoconstrictors. This initial response helps to limit hemorrhage. After a short period, capillary vasodilatation occur secondary to local histamine release, and the cells responsible for inflammation are able to migrate to the wound bed. The timeline for cell migration in a normal wound healing process is predictable.

Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. They act to control bleeding and limit the extent of injury. Platelet degranulation also activates the complement cascade, specifically C5a, which is a potent chemoattractant for neutrophils.

As the inflammatory phase continues, more immune response cells migrate to the wound. Neutrophil, the second response cell, is responsible for debris scavenging, complement-mediated opsonization of bacteria, and bacteria destruction via oxidative burst mechanisms (superoxide and hydrogen peroxide formation). The neutrophils kill bacteria and decontaminate the wound from foreign debris.

The next cells present in the wound are the leukocytes and the macrophages (monocytes). Macrophage is essential for wound healing. Numerous enzymes and cytokines are secreted by the macrophage, including collagenases, which debride the wound; interleukins and tumor necrosis factor (TNF), which stimulate fibroblasts (production of collagen) and promote angiogenesis; and transforming growth factor (TGF), which stimulates keratinocytes. This marks the transition into the process of tissue reconstruction, the proliferative phase.

Epithelialization, angiogenesis, granulation tissue formation, and collagen deposition are the principal steps in the proliferative phase of wound healing. Epithelialization occurs early in wound repair. If the basement membrane remains intact, the epithelial cells migrate upwards in the normal pattern, as in first-degree skin burn. The epithelial progenitor cells remain intact below the wound, and the normal layers of epidermis are restored in 2-3 days. If the basement membrane has been destroyed, similar to a second- or third-degree burn, then the wound is reepithelialized from the normal cells in the periphery and from the skin appendages, if intact (eg, hair follicles, sweat glands).

Angiogenesis, stimulated by TNF-alpha, is marked by endothelial cell migration and capillary formation. The new capillaries deliver nutrients to the wound and help maintain the granulation tissue bed. The migration of capillaries into the wound bed is critical for proper wound healing. The granulation phase and tissue deposition require nutrients supplied by the capillaries, and failure for this to occur results in a chronically unhealed wound. Mechanisms for modifying angiogenesis are under study and have significant potential to improve the healing process.

The final part of the proliferative phase is granulation tissue formation. Fibroblasts differentiate and produce ground substance and then collagen. The ground substance is deposited into the wound bed. Collagen is then deposited as the wound undergoes the final phase of repair. Many different cytokines are involved in the proliferative phase of wound repair. The steps and the exact mechanism of control have not been elucidated. Some of the cytokines include PDGF, insulin like growth factor (IGF), and EGF. All are necessary for collagen formation.

The final phase of wound healing is the maturational phase. The wound undergoes contraction, ultimately resulting in a smaller amount of apparent scar tissue. The entire wound healing process is a dynamic continuum with an overlap of each phase and continued remodeling. Wound reaches maximal strength at one year and result in a tensile strength that is 30% of normal skin. Collagen deposition continues for a prolonged period, but the net increase in collagen deposition plateaus after 21 days.

Proper wound healing involves a complex interaction of cells and cytokines working in concert. Particularly, cytokines and chemokines orchestrate the progression of healing and are fundamental to the cellular and biochemical events that occur during acute wound healing. These effectors can be measured in serum and wound effluent using modern molecular techniques.

Currently, the only available commercial product proven to be efficacious in wound healing is PDGF, which is available as recombinant human PDGF-BB. In multiple studies, recombinant human PDGF-BB has been demonstrated to reduce healing time and improve the incidence of complete wound healing in stage III and IV ulcers. Other cytokines being studied for wound healing include TGF-beta, EGF, and IGF-1.

Breast carcinoma is the most commonly diagnosed cancer and the second leading cause of cancer-related mortality among women in the United States [50]. In 2009, there were over 192,000 estimated new cases of cancer of the breast, and over 40,000 disease-specific deaths [50]. Breast cancer-related mortality rates have steadily decreased over the past two decades, largely due to improved disease detection and therapy [51].

As breast cancer in younger (under age 40) women is infrequently diagnosed in the early stages utilizing current screening guidelines, improved cancer screening and detection methods are important in current research, particularly in younger, at-risk women [52]. Breast cancer in younger women typically has unfavorable prognostic characteristics associated with increased disease-specific mortality [53-55]. Younger women are not typically referred for periodic imaging unless they are identified as being "high risk" [56]. "At risk" younger women with significant family history or genetic factors are encouraged to undergo frequent clinical and annual breast imaging surveillance, and to consider chemoprevention.

While increased surveillance for "at risk" women may be beneficial, the value of this approach is restricted by the rarity of breast cancer due to known genetic risk factors [57, 58]. Over 90% of breast cancers are detected in women who are not identified as "high risk" [52]. Furthermore, screening mammography is generally less accurate in younger women and those with increased breast tissue density commonly encountered in women under age 40 [59]. The reduced sensitivity of mammography for dense breasts impacts age groups in which a "life saved" often results in "higher" personal and societal costs in terms of altered life expectancy and personal productivity [60].

MRI is being used increasingly as a screening modality in high-risk women with a significant family history of breast cancer, or BRCA1 or BRCA2 gene mutations resulting in lifetime risk of cancer exceeding 20% [61]. Hence, breast MRI is applied to a relatively small proportion of all women. MRI is unaffected by breast tissue density; however, the high cost, requirement for intravenous contrast administration, and variable specificity limit its feasibility for widespread population-based screening [62, 63].

Tamoxifen is considered in both pre- and post-menopausal women, and Raloxifene is considered in post-menopausal women, with lobular carcinoma in situ (LCIS) or with a 5-year breast cancer risk estimate of $\geq 1.66\%$ (according to the Gail Model or the NCI Breast Cancer Risk Assessment Tool), in order to reduce the risk of estrogen receptor-positive (ER+) breast cancer [64]. In the NSABP P-1 study, Tamoxifen (20 mg/day for 5 years) consistently reduced the incidence of breast cancer by 49% in at-risk women across all study age and risk groups (women age 35-59 with a $\geq 1.66\%$ risk, those $\geq 60$, or with prior LCIS), thereby demonstrating the efficacy of chemoprevention for this disease [65]. The MORE, CORE, RUTH and NSABP STAR Trials demonstrated consistent significant reductions in ER+ breast cancer incidence in at-risk post-menopausal women [64]. Subsequent analyses of the NSABP P-1 study data suggested improved quality-adjusted survival and cost effectiveness when Tamoxifen was initiated as early as age 35 in at-risk (Gail Model 5-year risk≧1.66%) women [66, 67].

Lifetime relative risk assessment tools (e.g., Gail model) are available to identify women over age 35 years who are at-risk for breast cancer. However, the predictive value of mathematical models to estimate breast cancer risk varies according to age, menopausal status, race/ethnicity, and family history of breast cancer. Instruments such as the Gail model are imperfect for identifying increased cancer risk in younger women [68]. Current risk prediction models estimate population, not individual levels of breast cancer risk. Currently, the only criterion generally used to identify high-risk young women who could benefit from chemoprevention is family/genetic history. The value of this risk estimation paradigm is limited by the rarity of breast cancer due to known gene mutations.

III. SUMMARY OF THE INVENTION

An embodiment of the invention provides a highly predictive clinical decision support tool to assist physicians in determining personalized risk of disease (malignancy, transplant glomerulopathy, healing rate of an acute traumatic wound, and/or breast cancer risk). For instance, in at least one embodiment, a Bayesian Belief Network model is trained using a machine learning algorithm applied to the specific patient study population with thyroid nodules characterized by relevant clinical variables. The algorithm is used to develop a model-derived risk assessment tool that supports clinical decision making on the basis of individual patient risk of malignancy rather than traditional risk-pool allocation. An integrated predictive decision model using Bayesian inference, which incorporates readily obtainable thyroid nodule measures (e.g., size, sonographic and impedance characteristics, and aspiration cytology), effectively predicts cancer in patients presenting with thyroid nodules. A broad statistically validated network structure of multiple clinical variables provides a universal method to individualize patient care. This predictive risk assessment tool refines clinical decision making using multiple available parameters as well as partial information by providing case-specific risk scores in an operationally computational manner. The risk assessment tool and predictive model is updated continuously to include new clinical, treatment, and outcome information in order to expand its decision support capability. The dynamic, quantitative case-specific predictions made by the predictive model allow the clinical decision support tool to be adapted to the specific needs and capabilities of a given medical clinic. Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements.

FIG. 5 illustrates a table of the cross-validation results according to an embodiment of the invention;

FIG. 8 illustrates an inference table according to an embodiment of the invention;

Figure 10A:
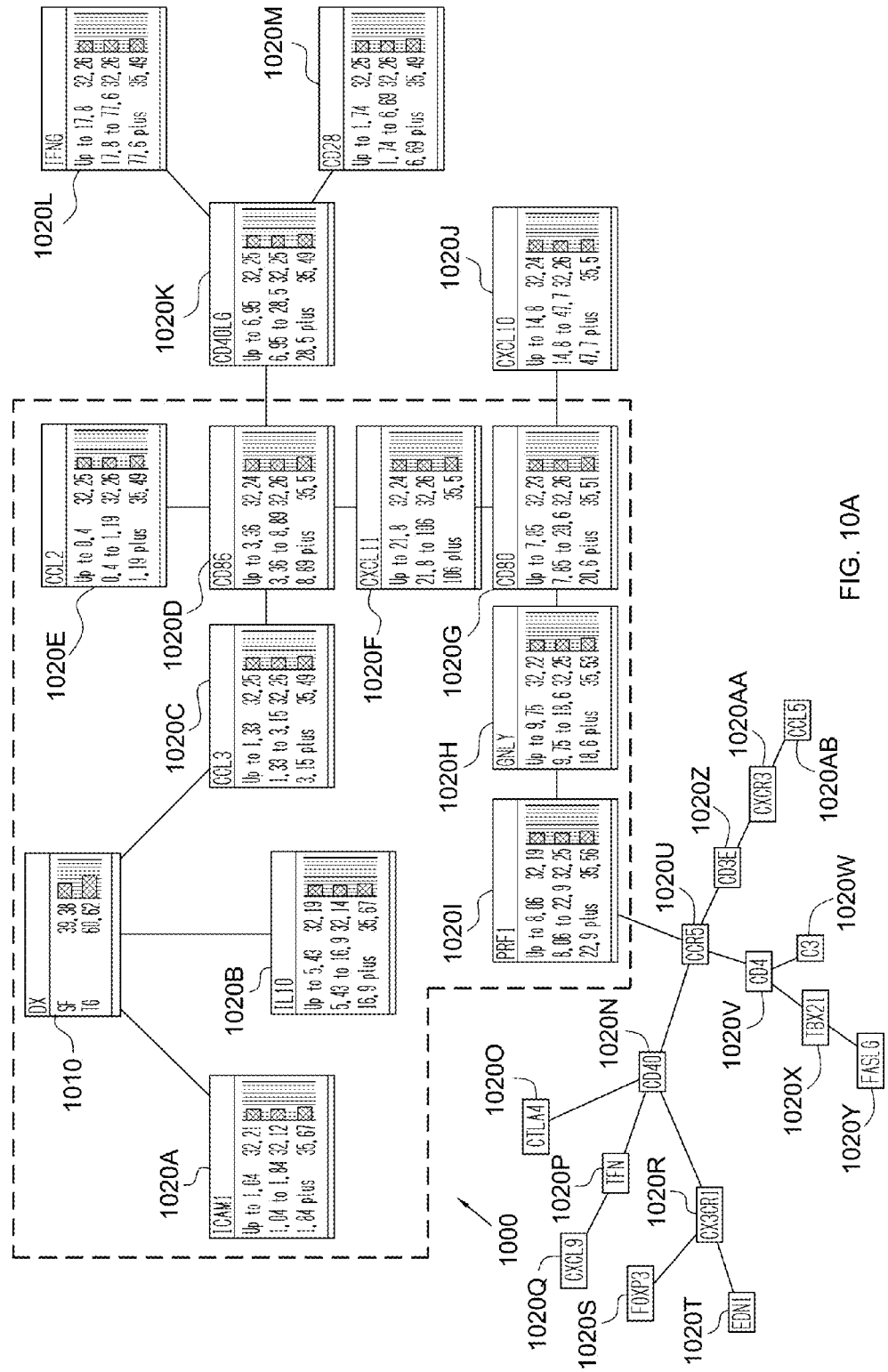
Figure 10B:
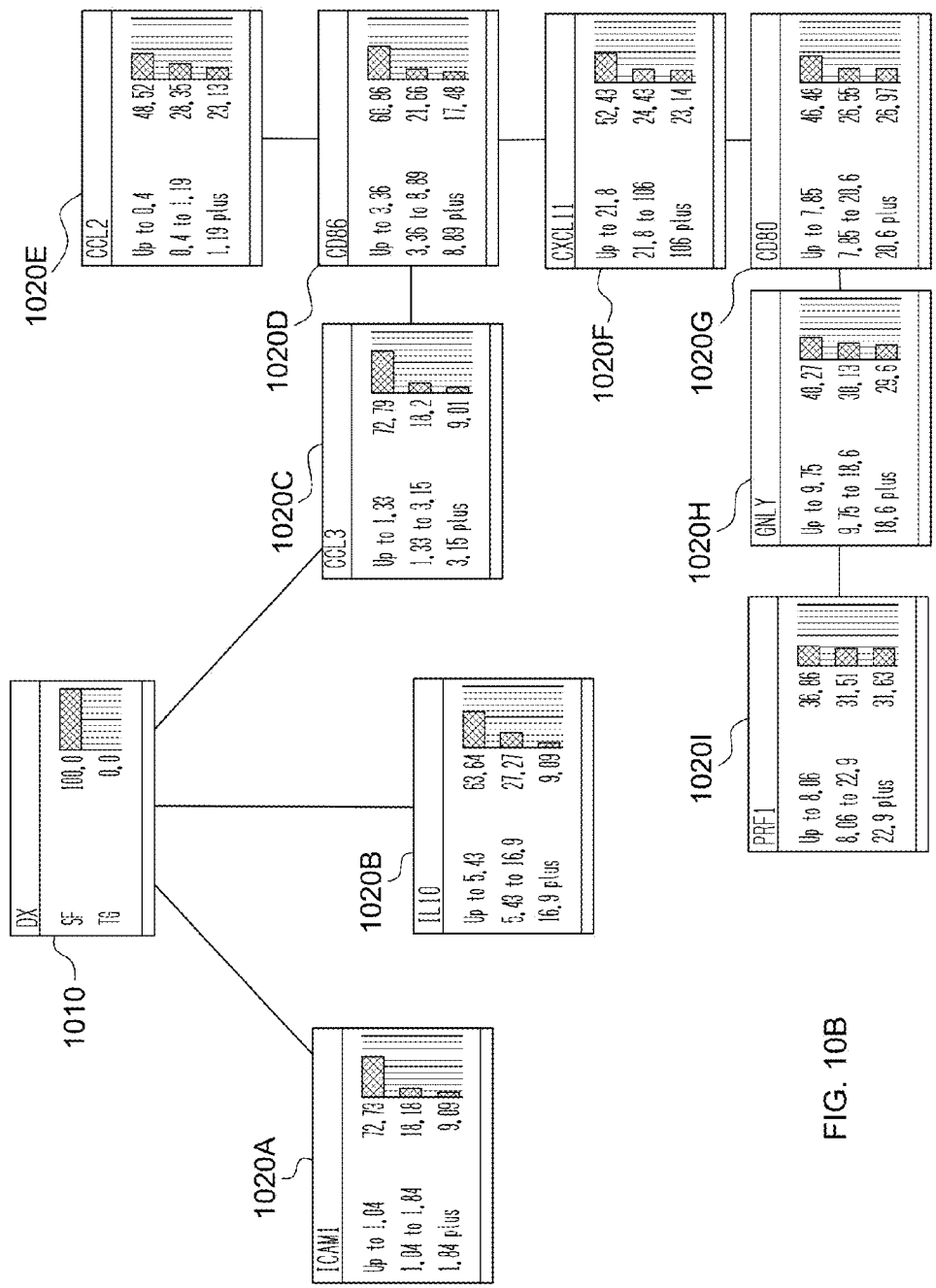
Figure 10C:
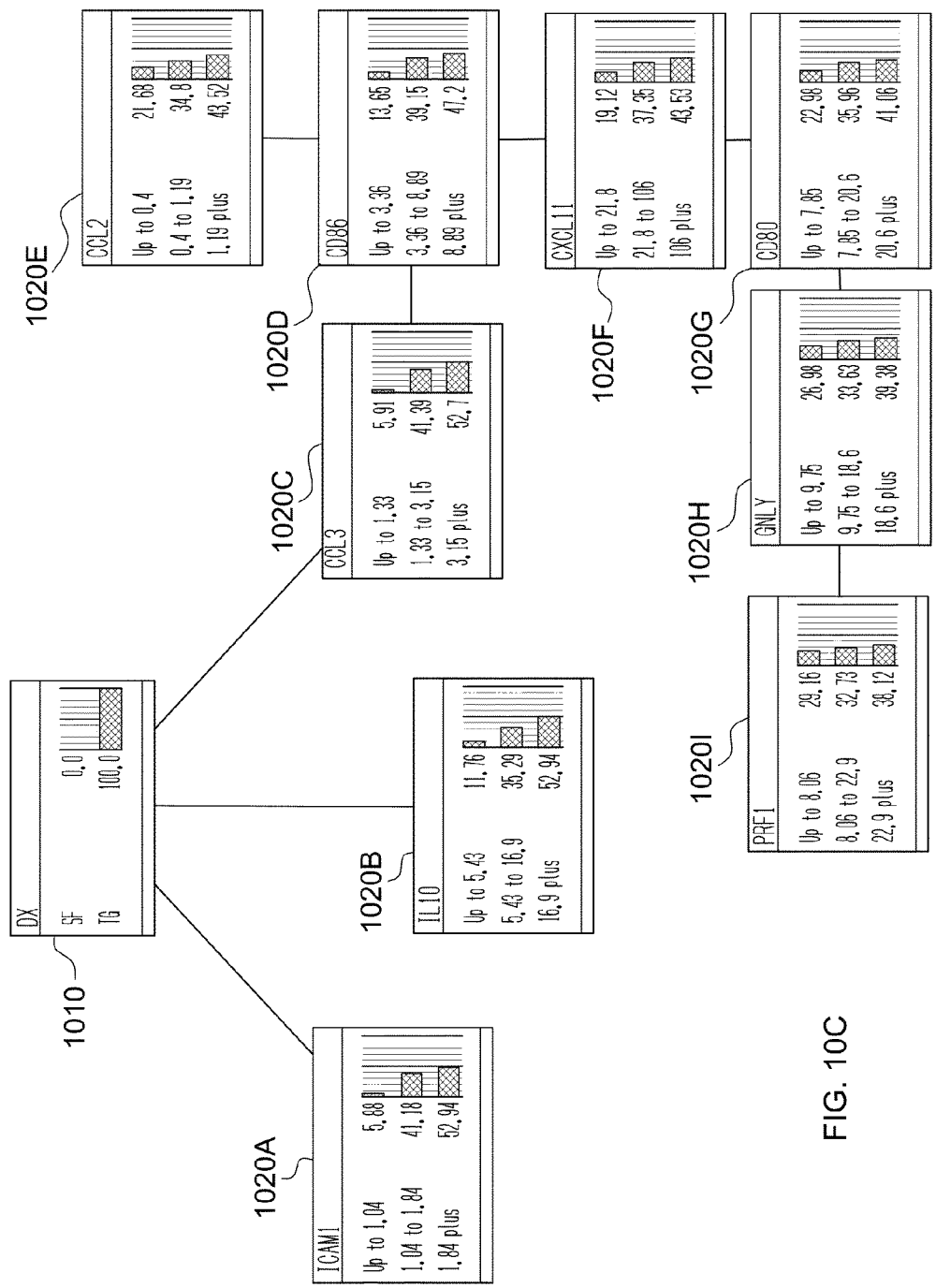
Figure 11A:
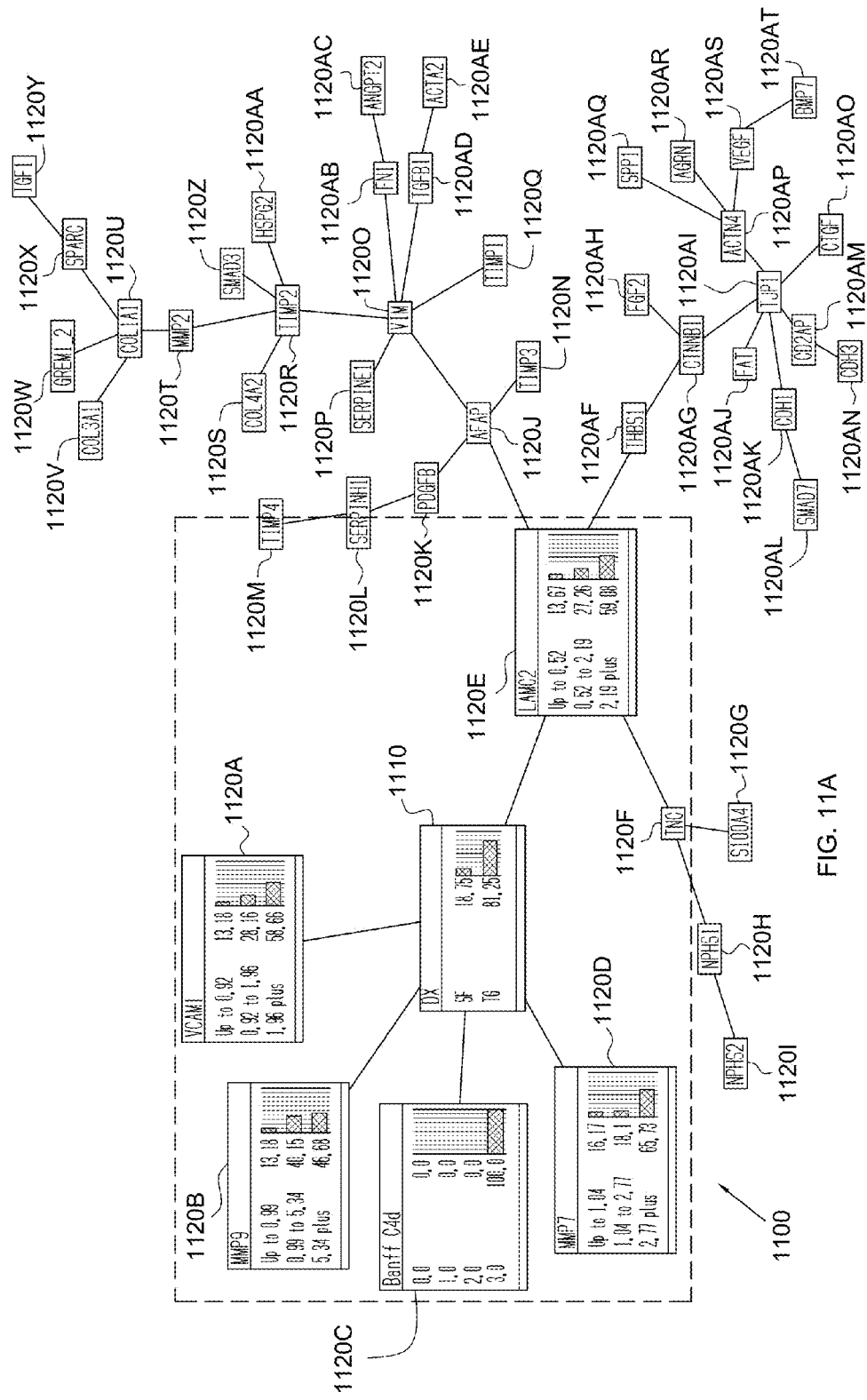
Figure 11B:
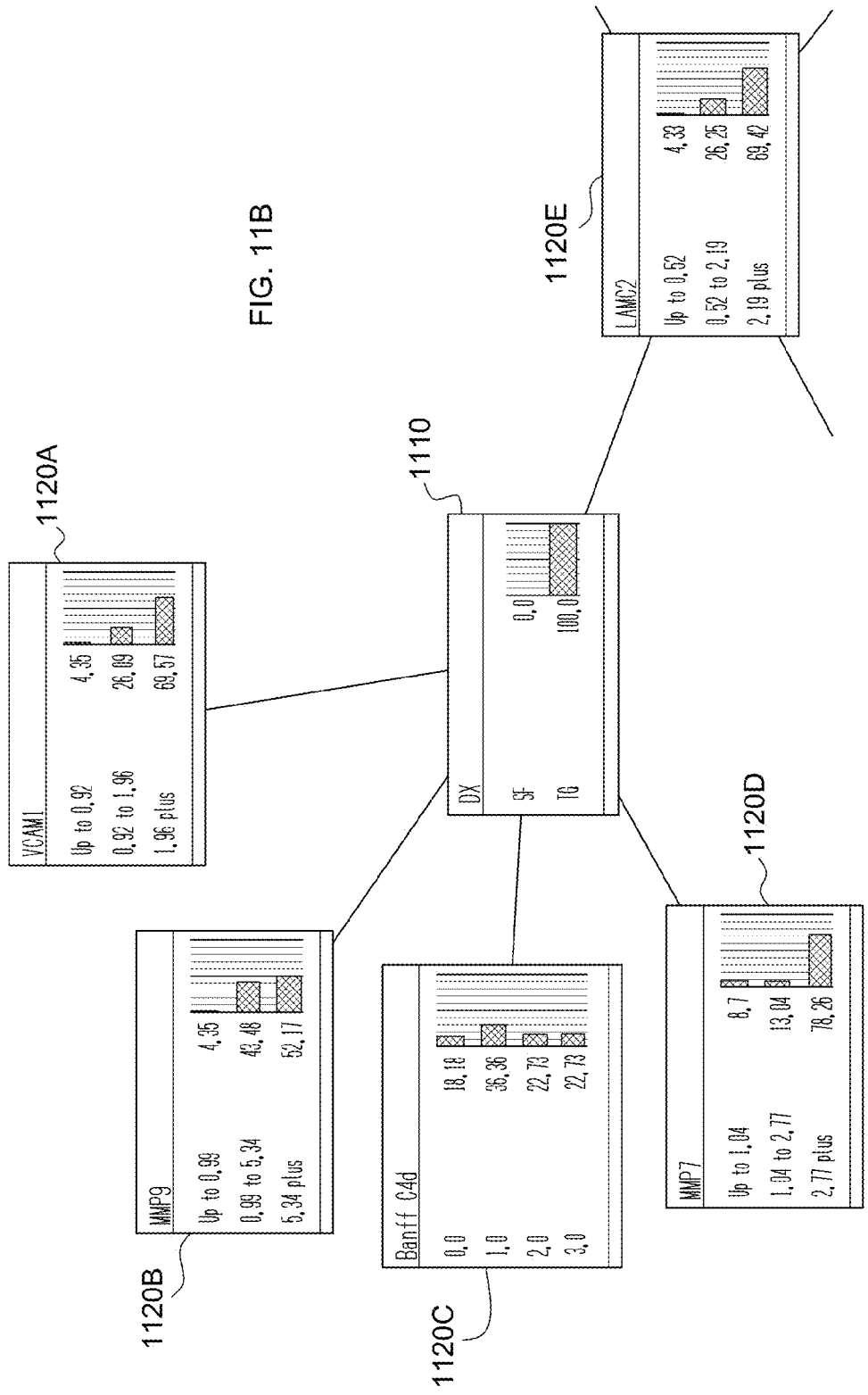
Figure 11C:
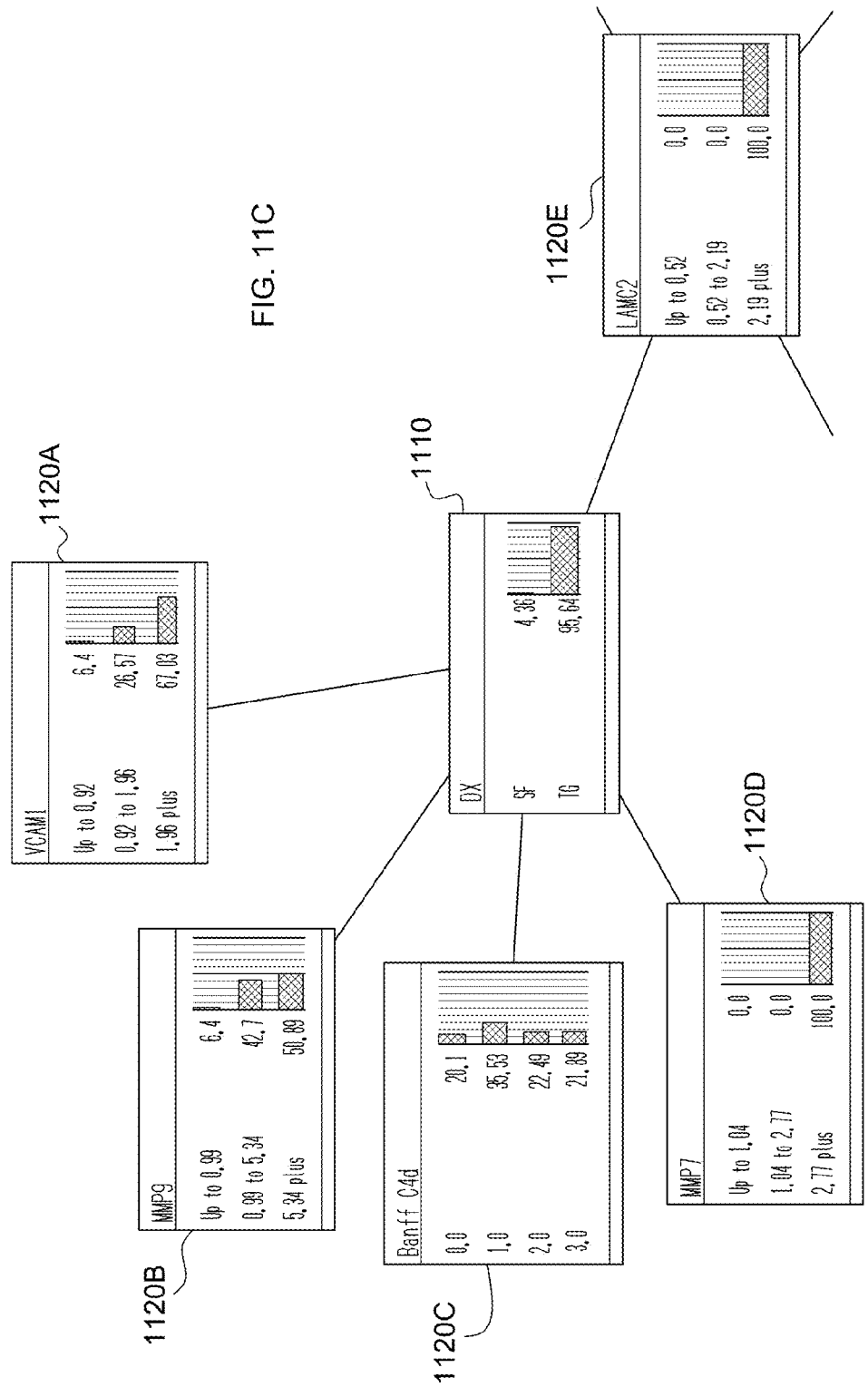
Figure 12A:
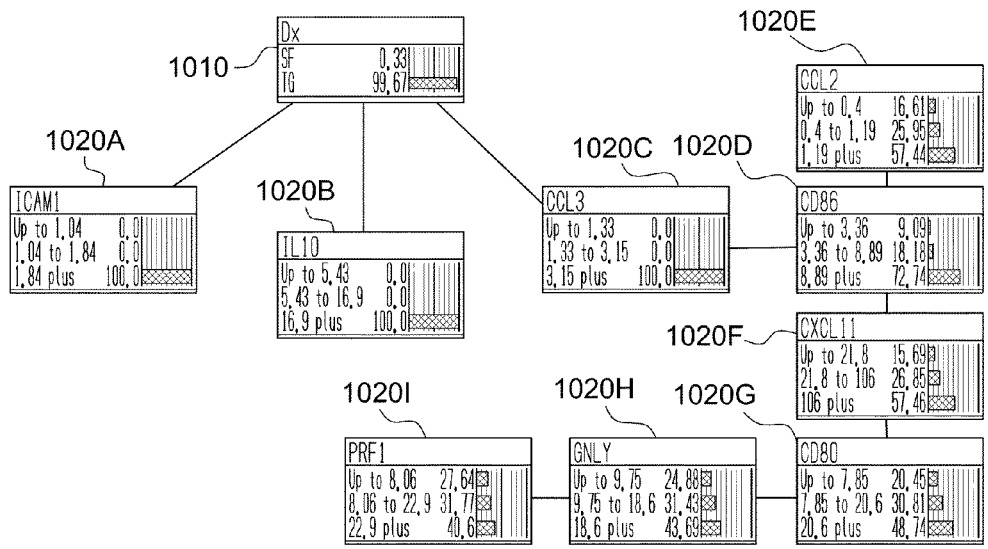
Figure 12B:
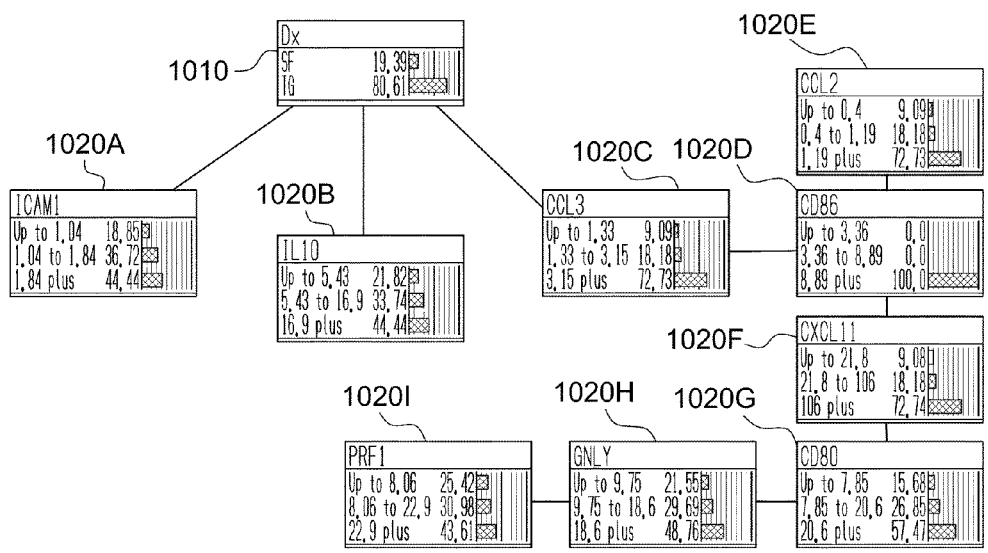
Figure 17:
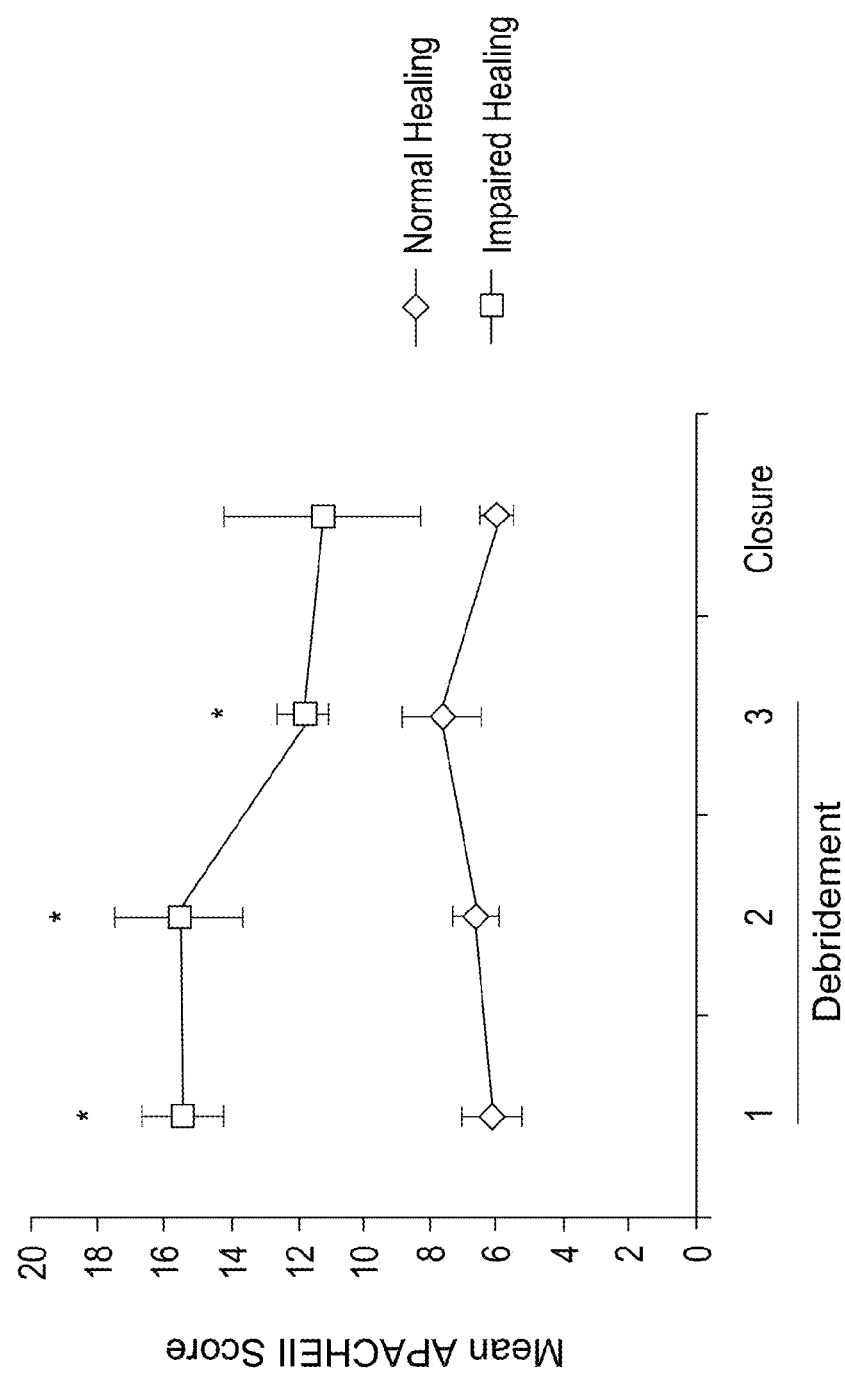
Figure 18:
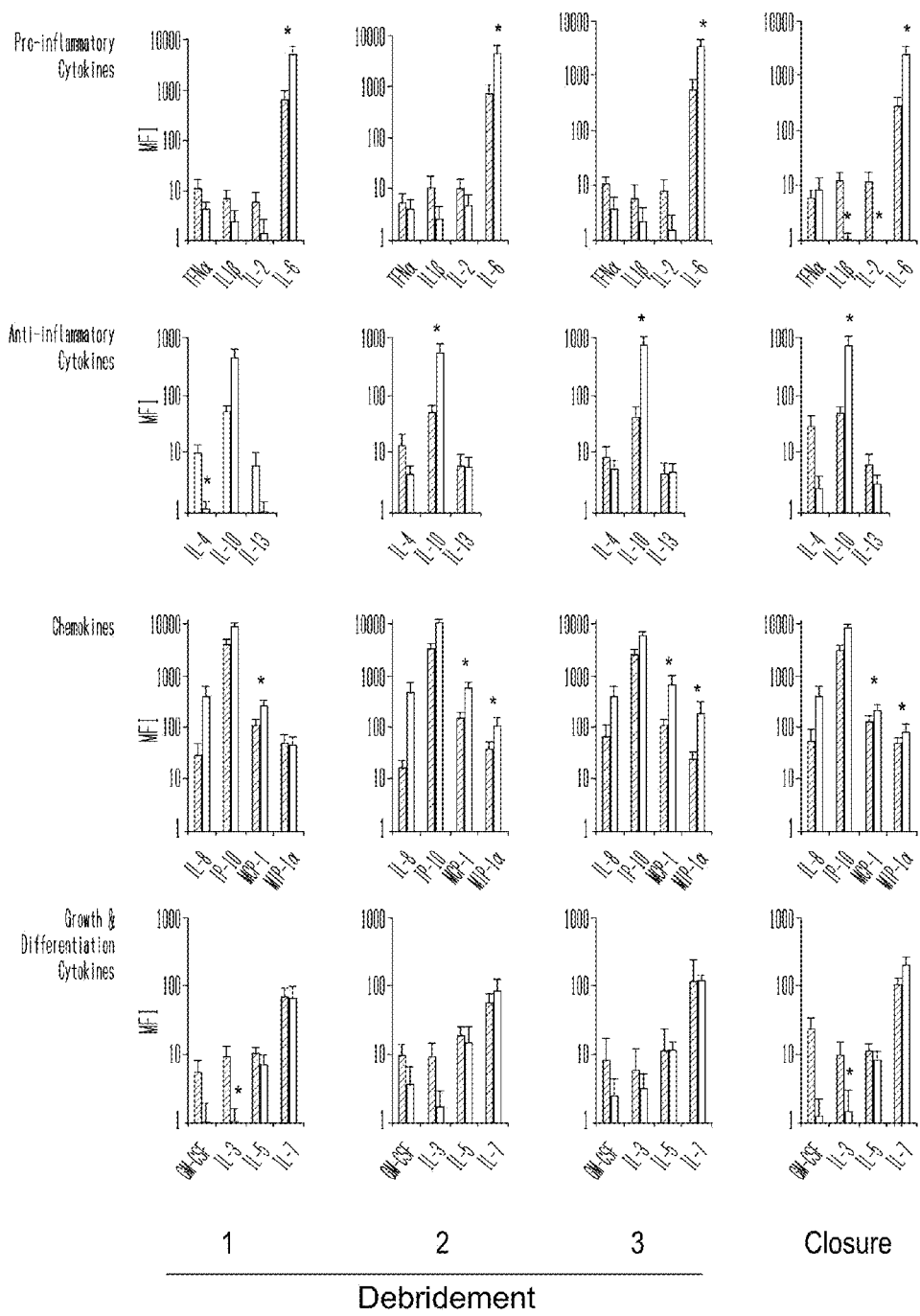
Figure 19:
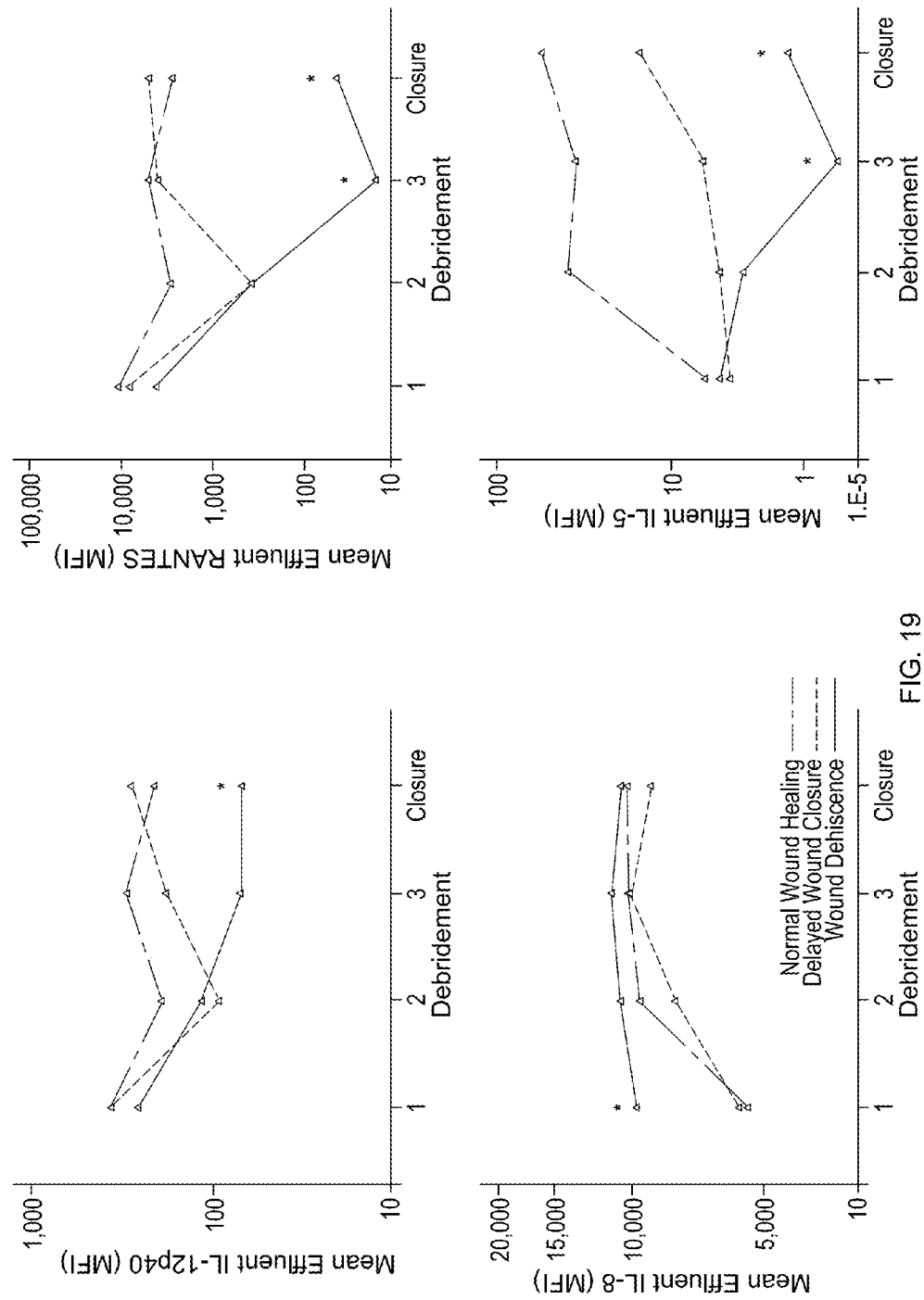
Figure 20A:
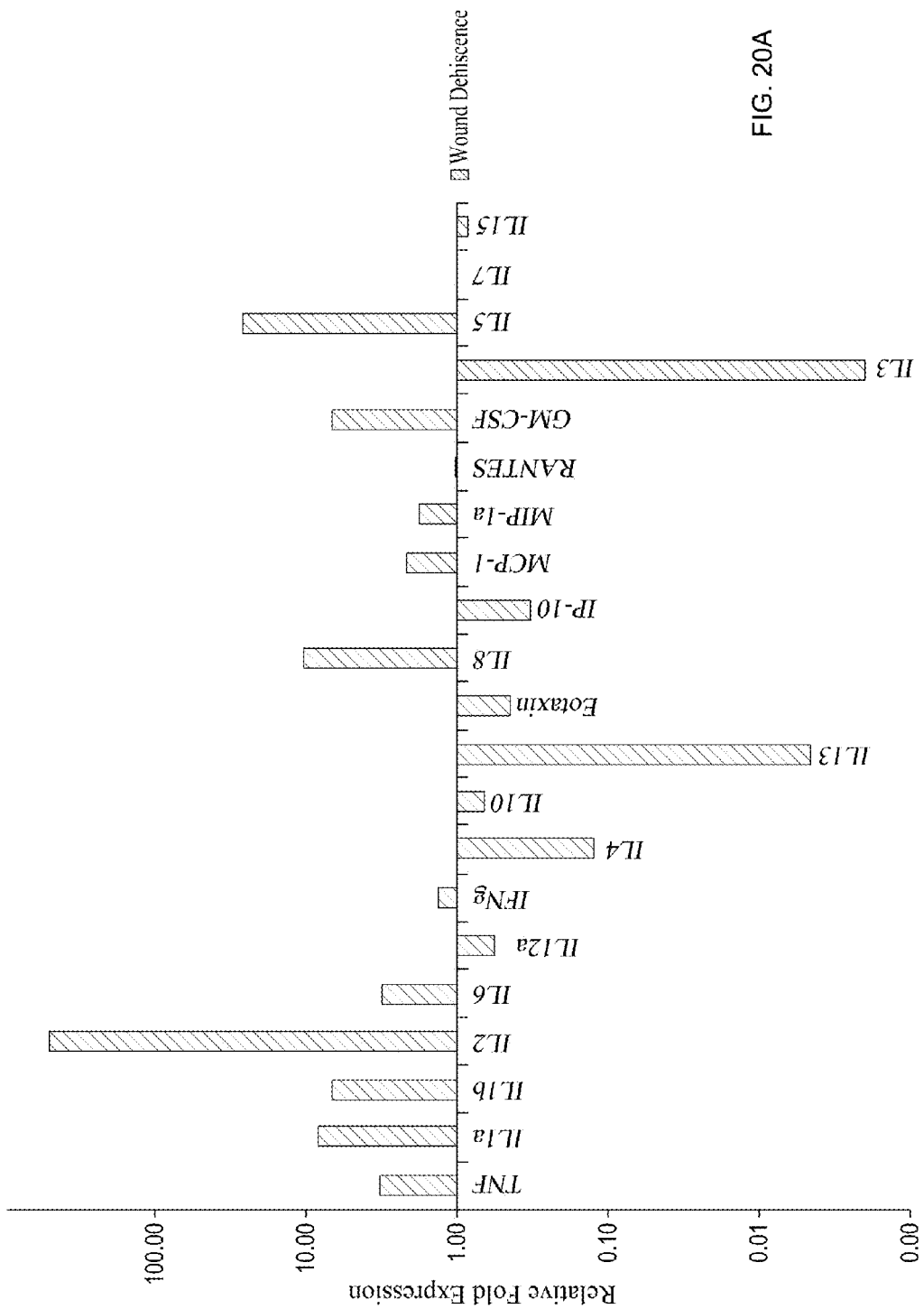
Figure 20B:
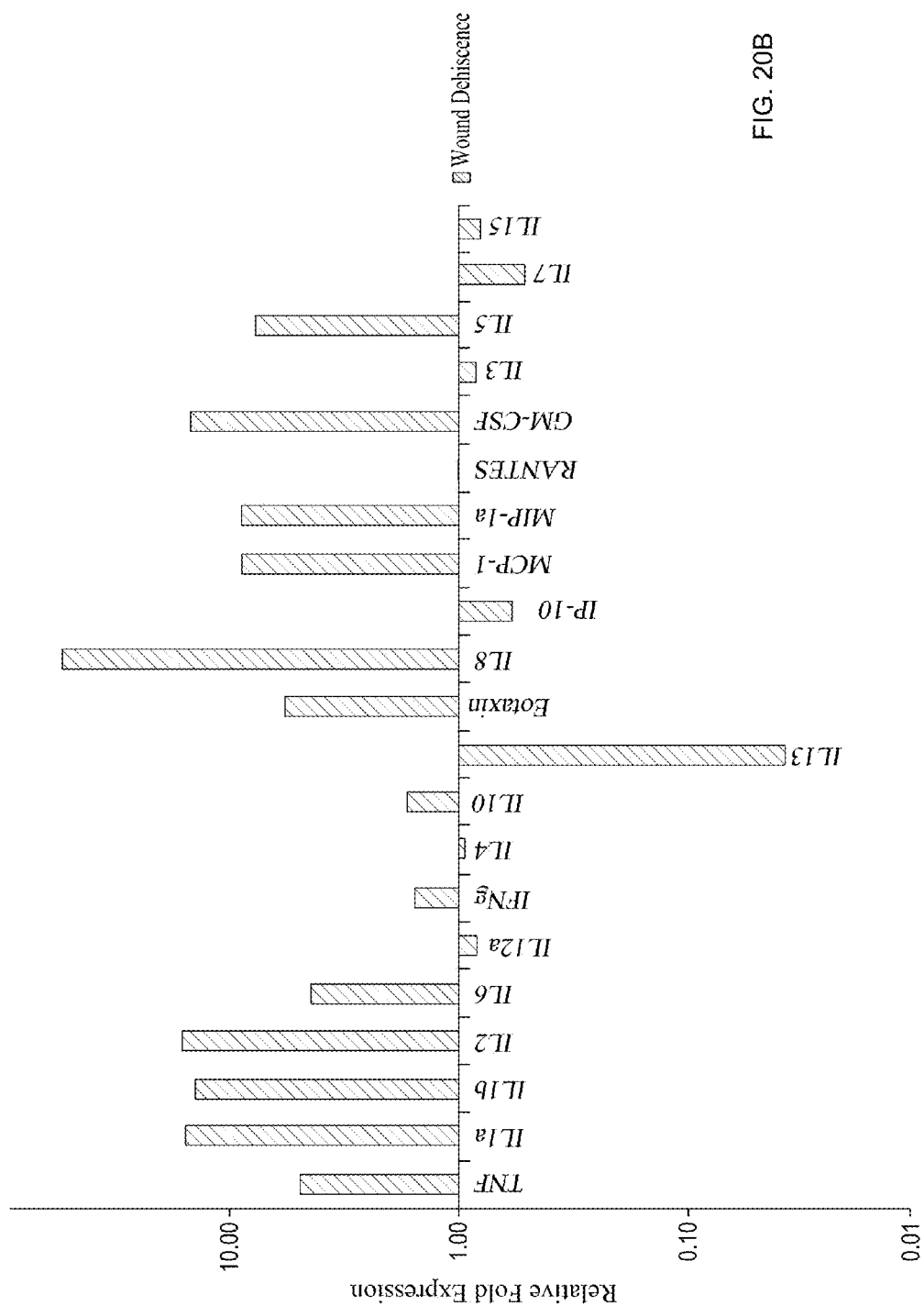
Figure 21A:
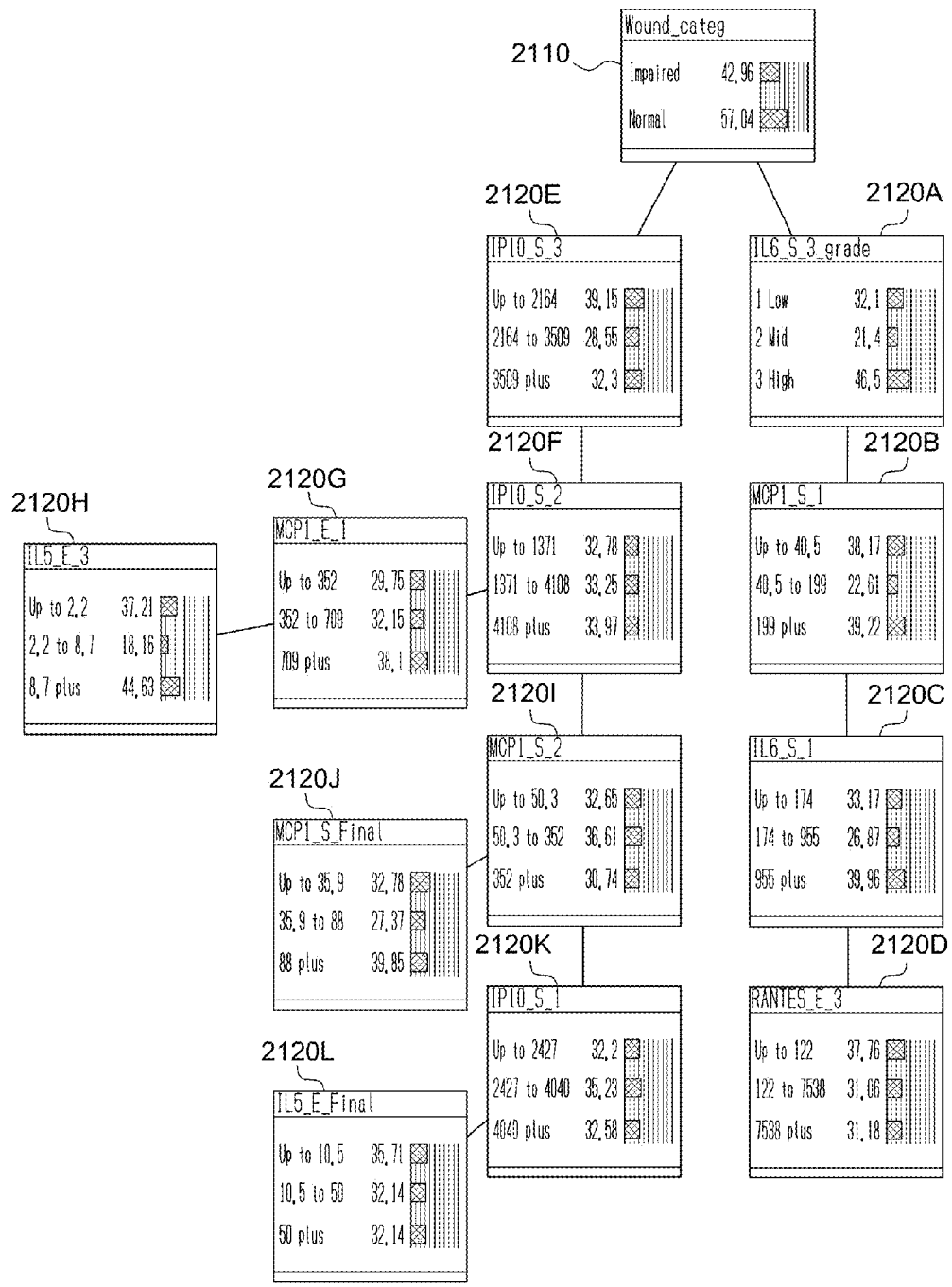
Figure 21B:
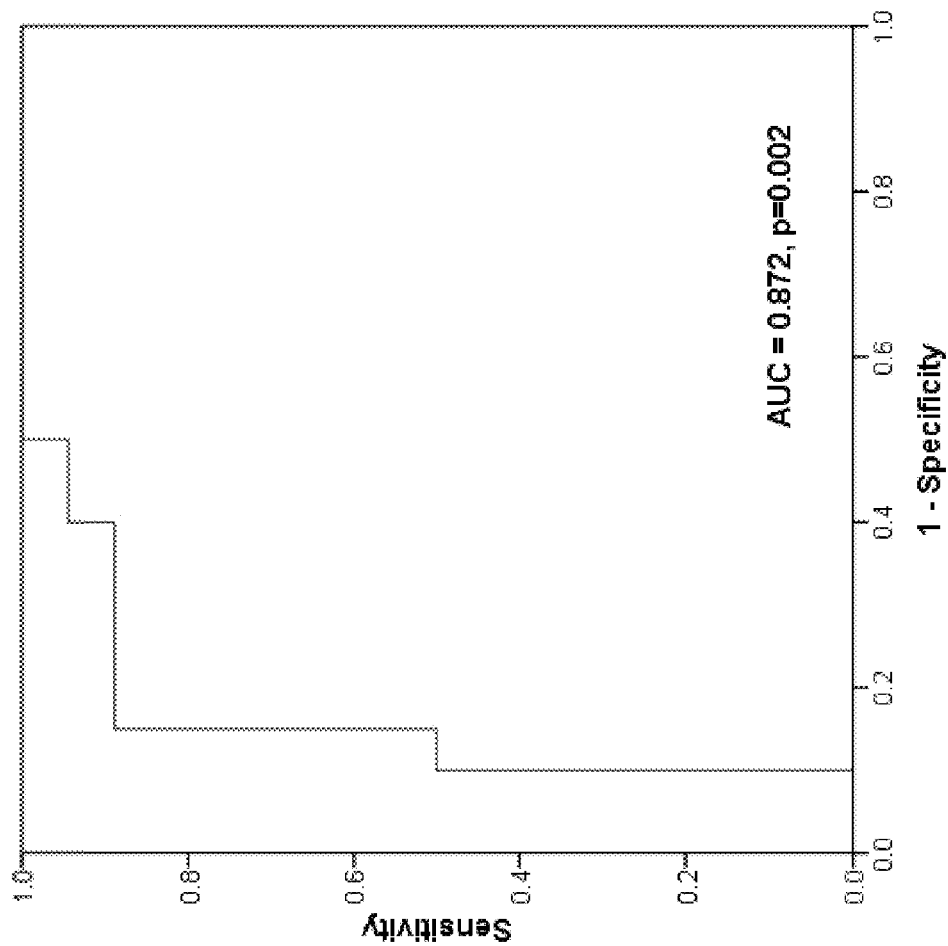
Figure 24:
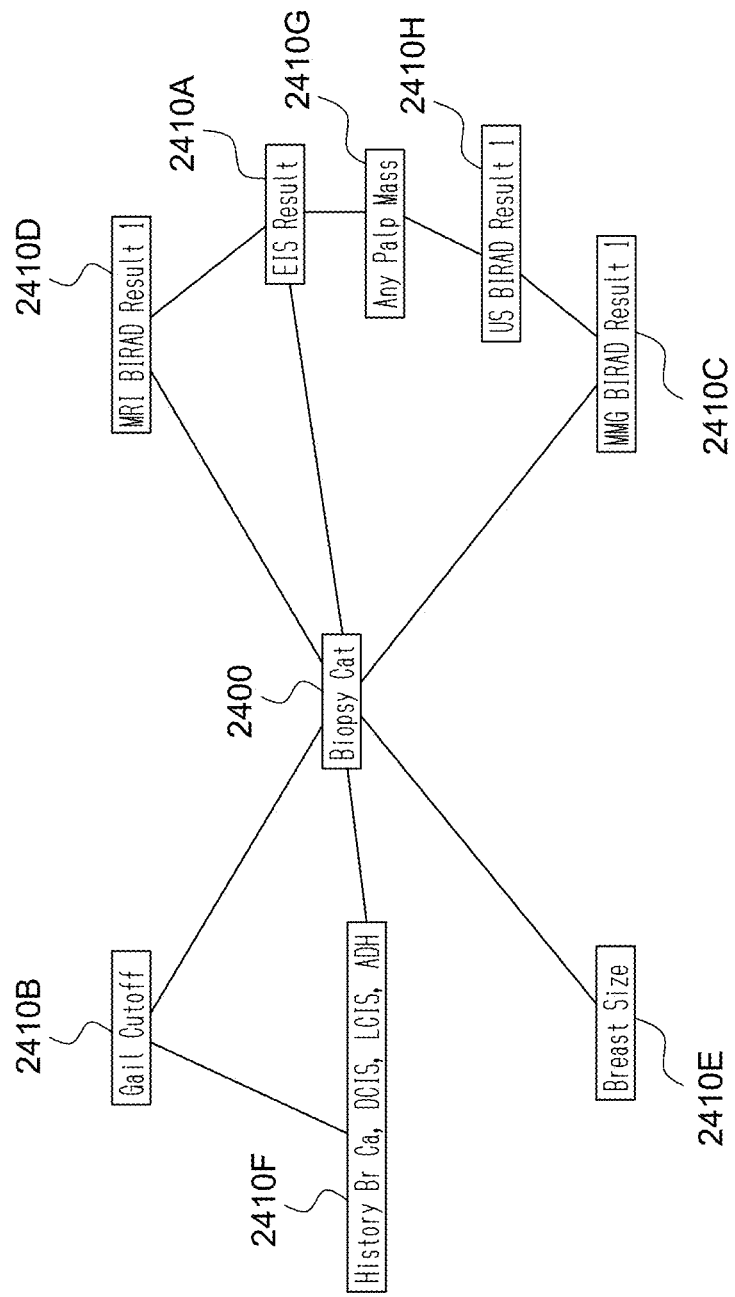
Figure 26A:
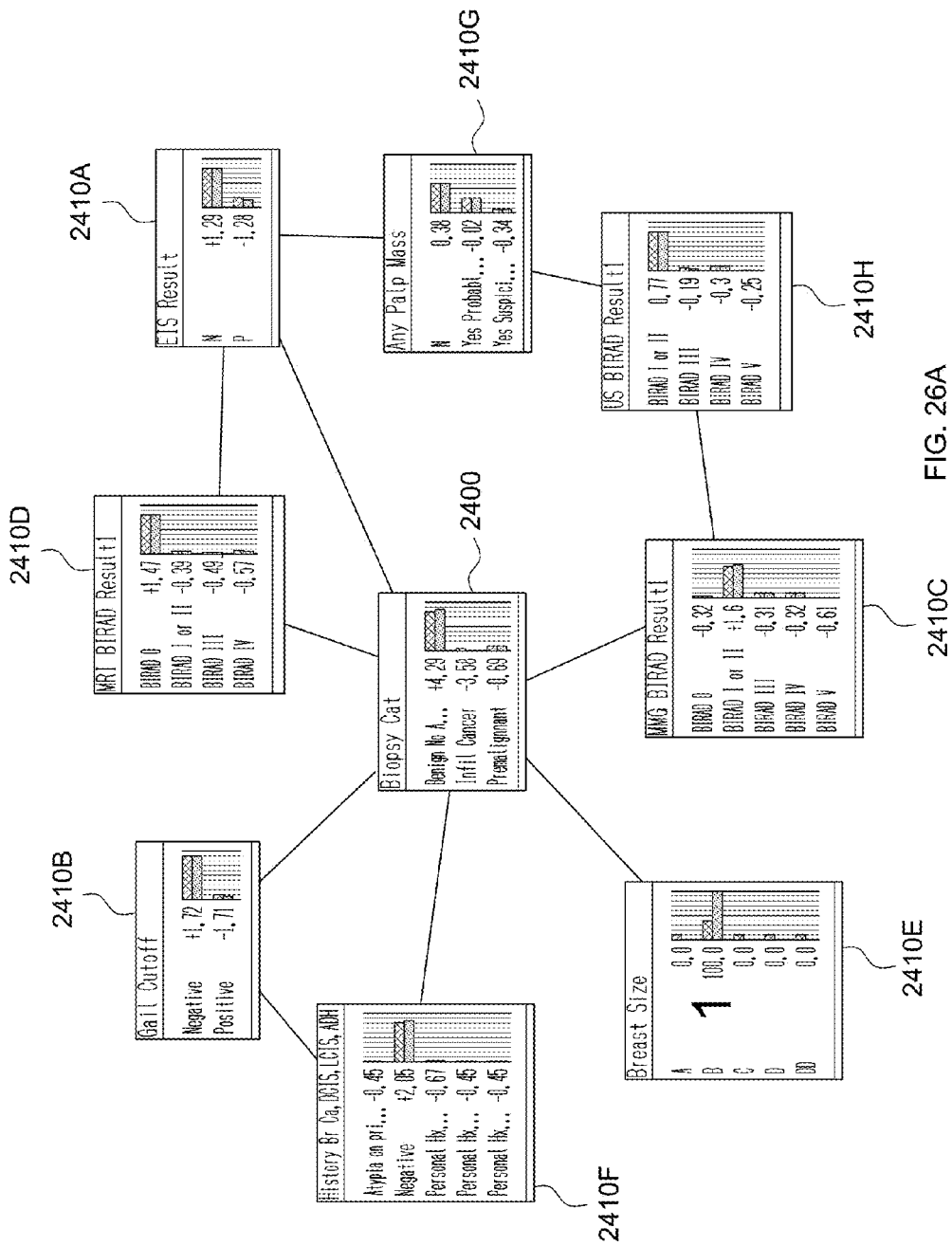
Figure 26B:
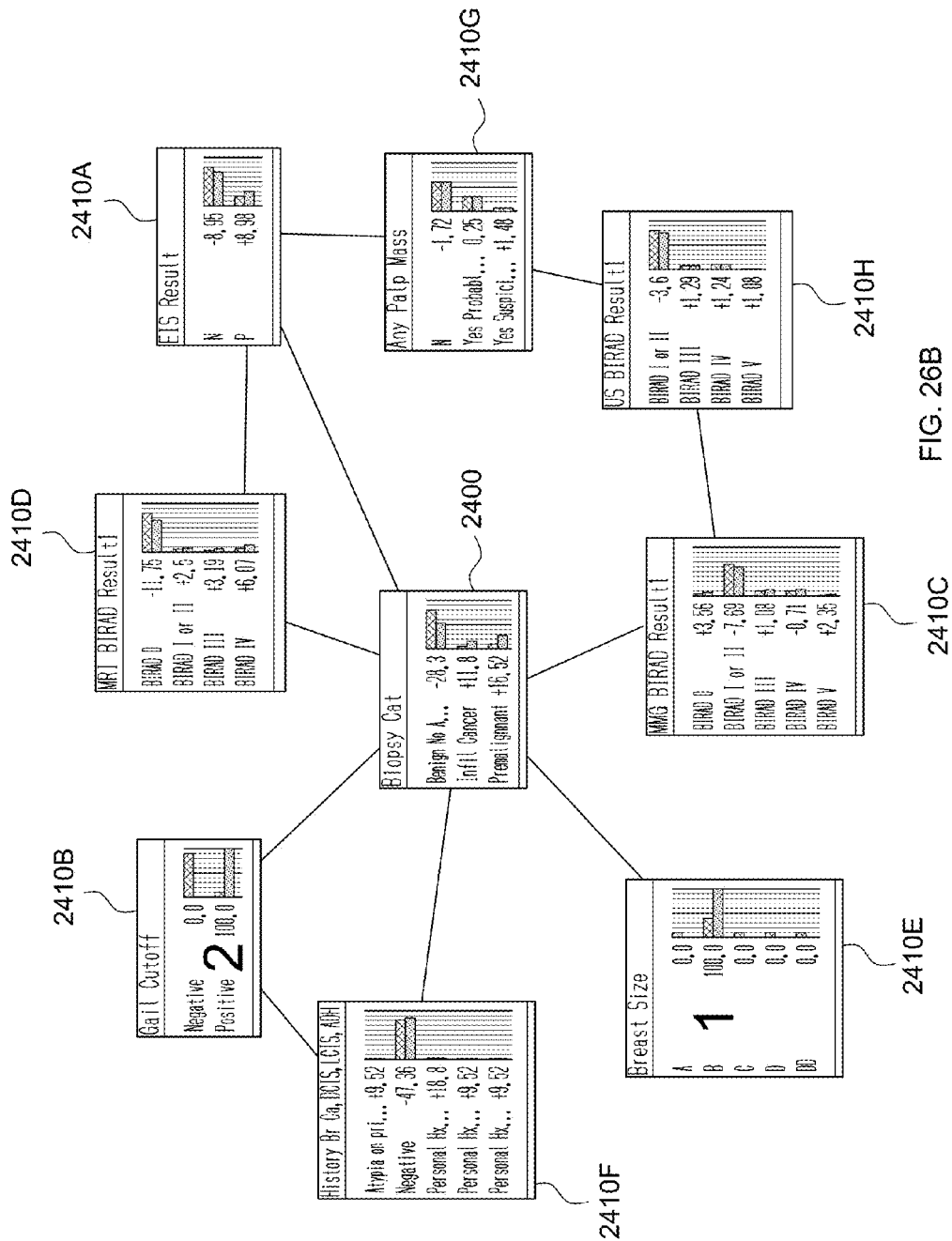
Figure 26C:
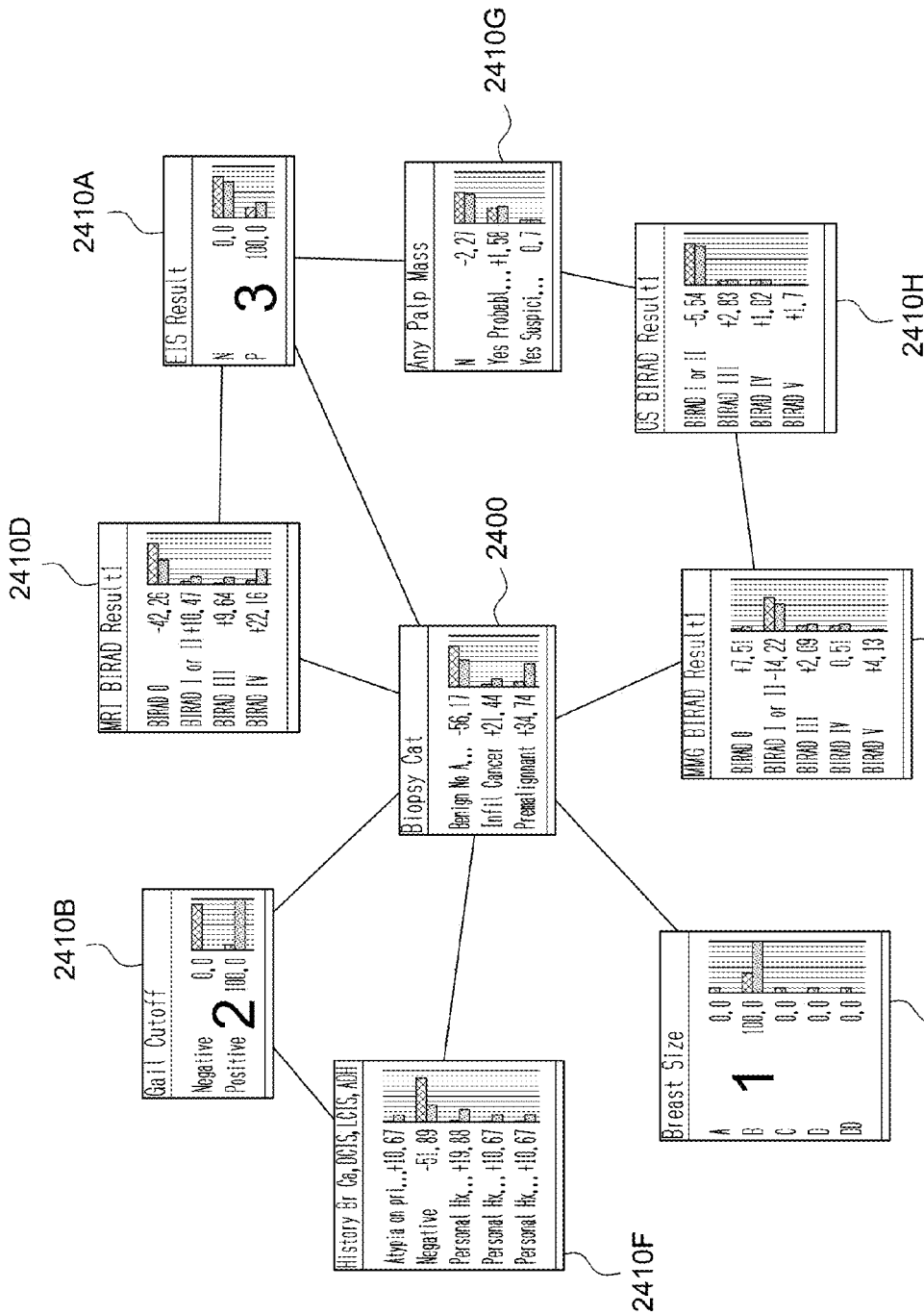
Figure 28:
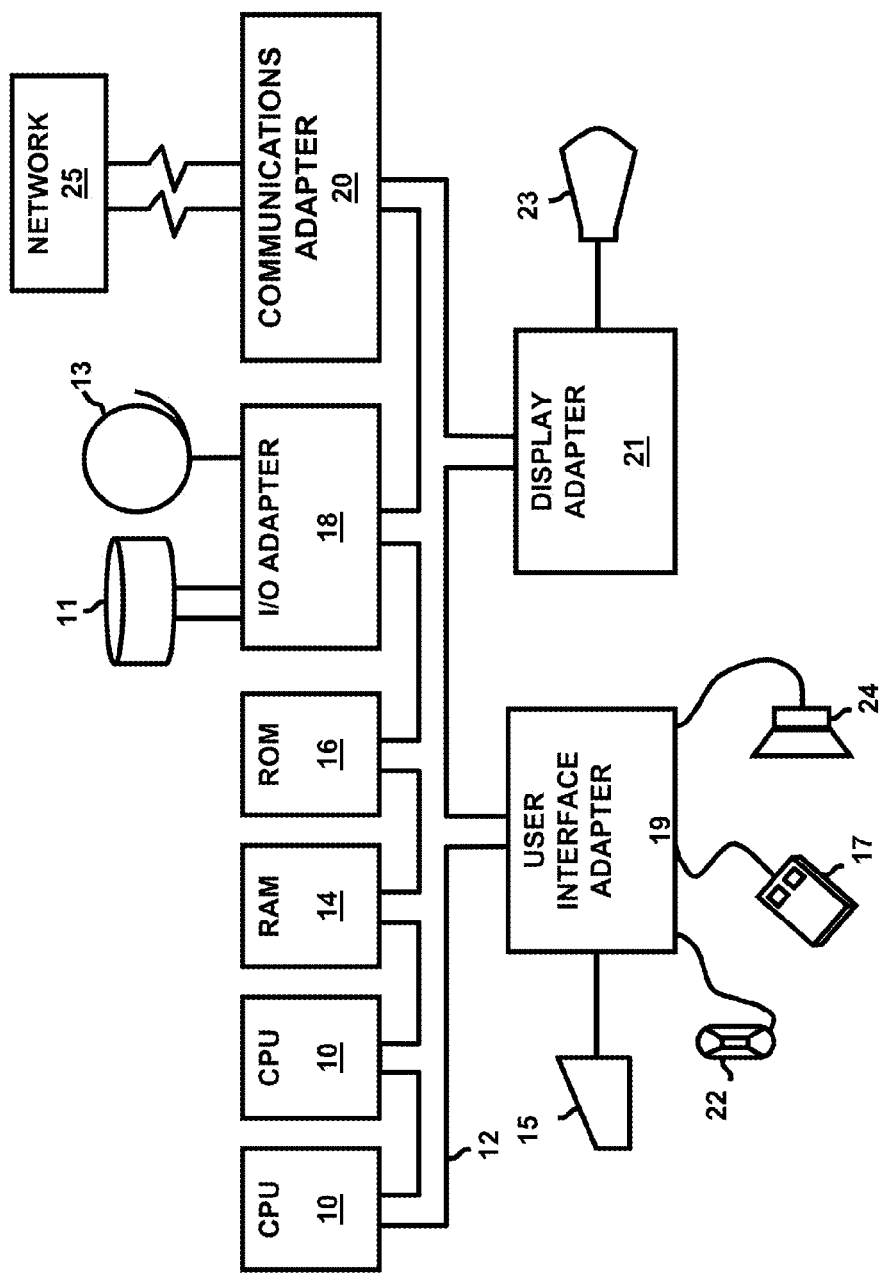

FIGS. 10A-C illustrate a BBN network model of relative-fold expression changes in a panel of genes according to an embodiment of the invention;

FIGS. 11A-C illustrate a BBN network model emphasizing surrogate biomarkers according to an embodiment of the invention;

FIGS. 12A-B illustrate a BBN network model for determining the probability of transplant glomerulopathy using Banff C4d deposition according to an embodiment of the invention;

FIG. 13 is a table illustrating stable function versus transplant glomerulopathy using the Laminin and Matrix Metalloproteinase-7 genes according to an embodiment of the invention;

FIG. 14 is a table illustrating gene symbols of current wound healing target genes according to an embodiment of the invention;

FIG. 15A-15J is a table illustrating gene names according to an embodiment of the invention;

FIG. 16 is a table illustrating patient (wound) demographics according to an embodiment of the invention;

FIG. 17 illustrates mean APACHE II scores at each wound debrigement (P<0.05) according to an embodiment of the invention;

FIG. 18 illustrates serum cytokine and chemokine at each wound debridement of patient with Normal (dark grey) and Impaired (light grey) Wound Healing according to an embodiment of the invention (all data is depicted on a logarithmic scale as mean±SEM. P<0.05; MFI is the mean fluorescent intensity, which correlates to analyte concentration);

FIG. 19 illustrates selected VAC effluent cytokine and chemokine at different debridement according to an embodiment of the invention (IL-12p(40), RANTES, and IL-5 each show a significant difference in concentration at time of closure between wounds that healed and wounds that dehisced);

FIG. 20A illustrates wound biopsy gene expression of dehisced wounds relative to healed wounds at initial debridement according to an embodiment of the invention (the y-axes are fold-expression of the target gene in the wounds that dehisced relative to the wounds that healed);

FIG. 20B illustrates wound biopsy gene expression of dehisced wounds relative to healed wounds at final debridement according to an embodiment of the invention;

FIG. 21A illustrates a wound prediction model according to an embodiment of the invention;

FIG. 21B illustrates the receiver-operating characteristics of the cross validation according to an embodiment of the invention;

FIG. 21C-21G illustrate wound prediction models according to embodiments of the invention;

FIG. 22 is a table illustrating characteristics of the study population by age according to an embodiment of the invention;

FIG. 23 is a table illustrating characteristics of the study population by biopsy according to an embodiment of the invention;

FIG. 24 illustrates a BBN-ML for predicting breast cancer risk according to an embodiment of the invention;

FIG. 25 is a table illustrating cross validation statistics according to an embodiment of the invention;

FIGS. 26A-C illustrate a BBN-ML for predicting breast cancer risk according to an embodiment of the invention;

FIG. 27 illustrates an inference table showing the probability of biopsy diagnosis given the Gail model risk estimate and breast EIS result according to an embodiment of the invention; and FIG. 28 illustrates a program storage device according to an embodiment of the invention.

V. DETAILED DESCRIPTION OF THE DRAWINGS

Figure 1:
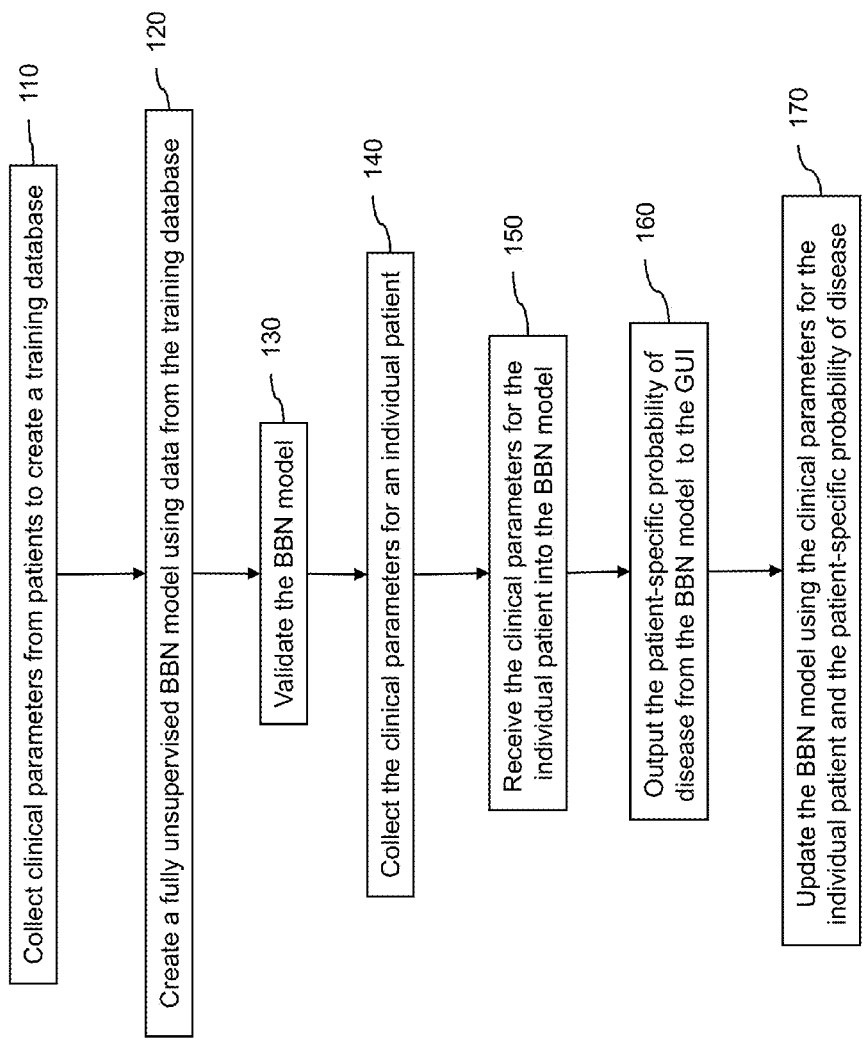
FIG. 1 is a flow diagram illustrating a method for pre-operatively determining a patient-specific probability of disease according to an embodiment of the invention.

FIG. 1 provides a general overview of one method for pre-operatively determining a patient-specific probability of disease (e.g., malignancy in a thyroid nodule, transplant glomerulopathy, wound healing, and breast cancer) according to an embodiment of the invention. Details of this and other embodiments of the invention are described below with reference to FIGS. 2-22. As described more fully below, a fully unsupervised machine-learned Bayesian Belief Network model (referred to herein as the "BBN-ML") is created, updated, and deployed without human-developed decision support rules. A machine learning algorithm allows the BBN-ML to learn dynamically from data that resides in a data warehouse. The machine learning algorithm automatically detects and promotes significant relationships between variables without the need for human interaction. This allows for the processing of vast amounts of complex data quickly and easily into a tractable Bayesian network. The structure of the network provides the user with immediate knowledge about the nature of the problem set and the relative significance of variables to the outcome of interest. By inputting current knowledge into the BBN-ML, the user obtains a probability of outcome and relative risk in real-time.

The method collects clinical parameters from patients to create a training database (110). As described more fully below, examples of the clinical parameters include a plurality of age, ethnicity, functional status of a thyroid nodule, pre-operative assessment, number of cervical lymph nodes, lymph node size, serum thyrotropin level, fine needle aspiration biopsy results, ultrasound data, nuclear medicine rating, imaging data, and/or biomarkers from serum and/or biopsy tissue. Although in some embodiments, not all of the example clinical parameters are use in a particular BBN-ML A fully unsupervised Bayesian Belief Network model is created using data from the training database (120); and, the BBN-ML is validated (130). In at least one embodiment, the structure of the BBN-ML is a directed acyclic graph that is learned natively from prior probabilities resident in the training database. Each node in the directed acyclic graph represents a clinical parameter and includes two or more bins. Each bin represents a value range for the clinical parameter (e.g., bin 1: gene expression level less than or equal to 1.0; bin 2: gene expression level greater than 1.0). As described below, a node can be created such that each bin in the node includes an equal number of data points. For example, the value ranges of bins 1-3 can be created such that 33% of the training population is in each bin. In at least one embodiment, cross-validation is performed, wherein the data is randomized into groups of matched training and test data, a classifier is trained on each of the training sets created in the data preparation step using the same data discretization and modeling parameters. Then each corresponding test set is used to create a set of case-specific predictions. A Receiver-Operating Characteristic (ROC) curve is plotted for each test exercise to estimate model robustness and classification accuracy. Upon completion, the best model structure is documented in, for example, XML format for deployment as the BBN-ML. In at least one embodiment, the relevant learning parameter and modeling log files are stored if future audits are performed.

The method in at least one embodiment collects the clinical parameters from an individual patient (140), which are received into the BBN-ML (150). The patient-specific probability of disease is output from the BBN-ML to a graphical user interface for use by a clinician in pre-operative planning (160). As described more fully below, the Bayesian models are in an interactive format such that a clinician can select an outcome or relative gene expression level by clicking on the graphical user interface and observing corresponding changes to the probability distribution of the remaining variables. The graphical user interface is also used to enter current, patient-specific data and receive an evidence-based prediction of diagnosis (e.g., transplant glomerulopathy or stable function), thus enabling patient-risk stratification and clinical intervention.

Figure 2:
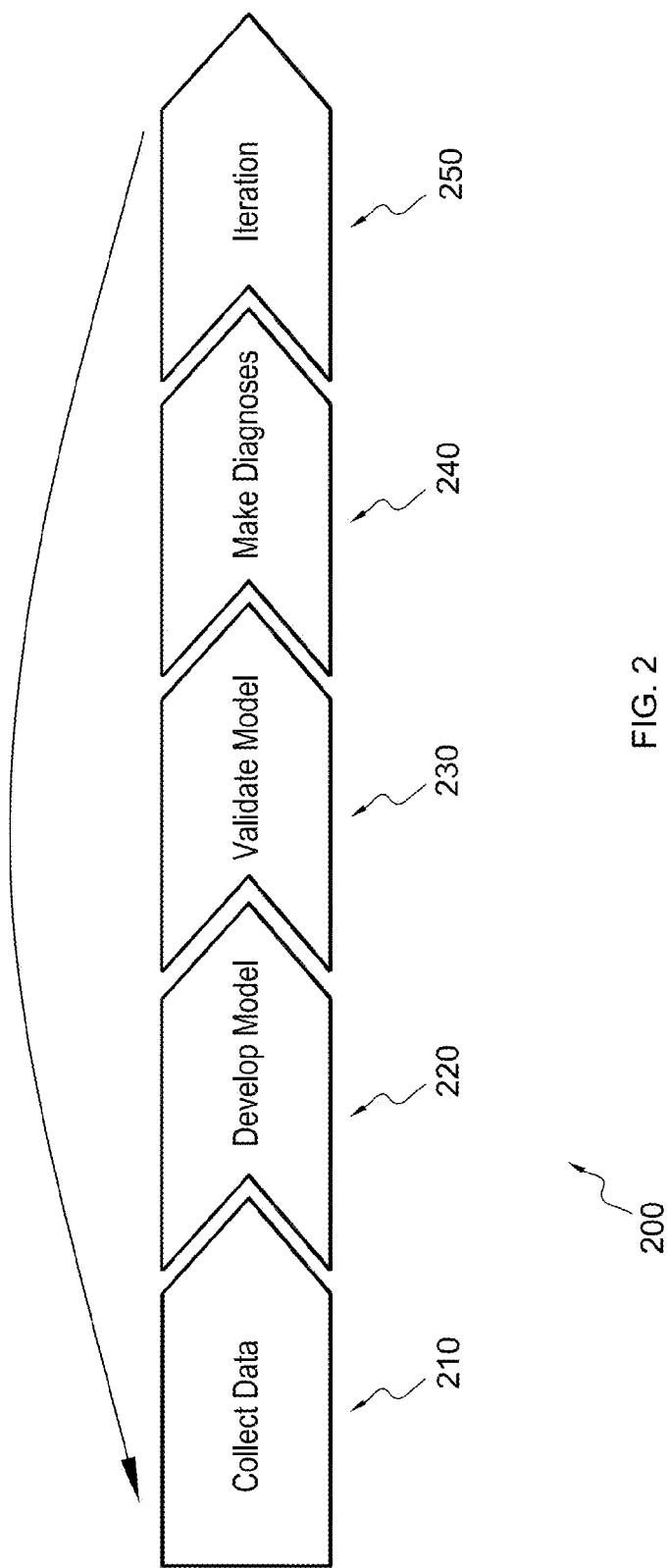
FIG. 2 illustrates a process of model development and deployment according to an embodiment of the invention.

The method updates the BBN-ML using the clinical parameters from the individual patient and the patient-specific probability of disease (170). As illustrated in FIG. 2, according to at least one embodiment, the ongoing process of model development and deployment 200 is one of data collection 210, model development 220, model validation 230, model deployment (i.e., diagnosis) 240, and iteration 250. This process is not static; it includes constant update, validation, and improvement. As new data is collected, models are updated and QC/QA documented.

Figure 3:
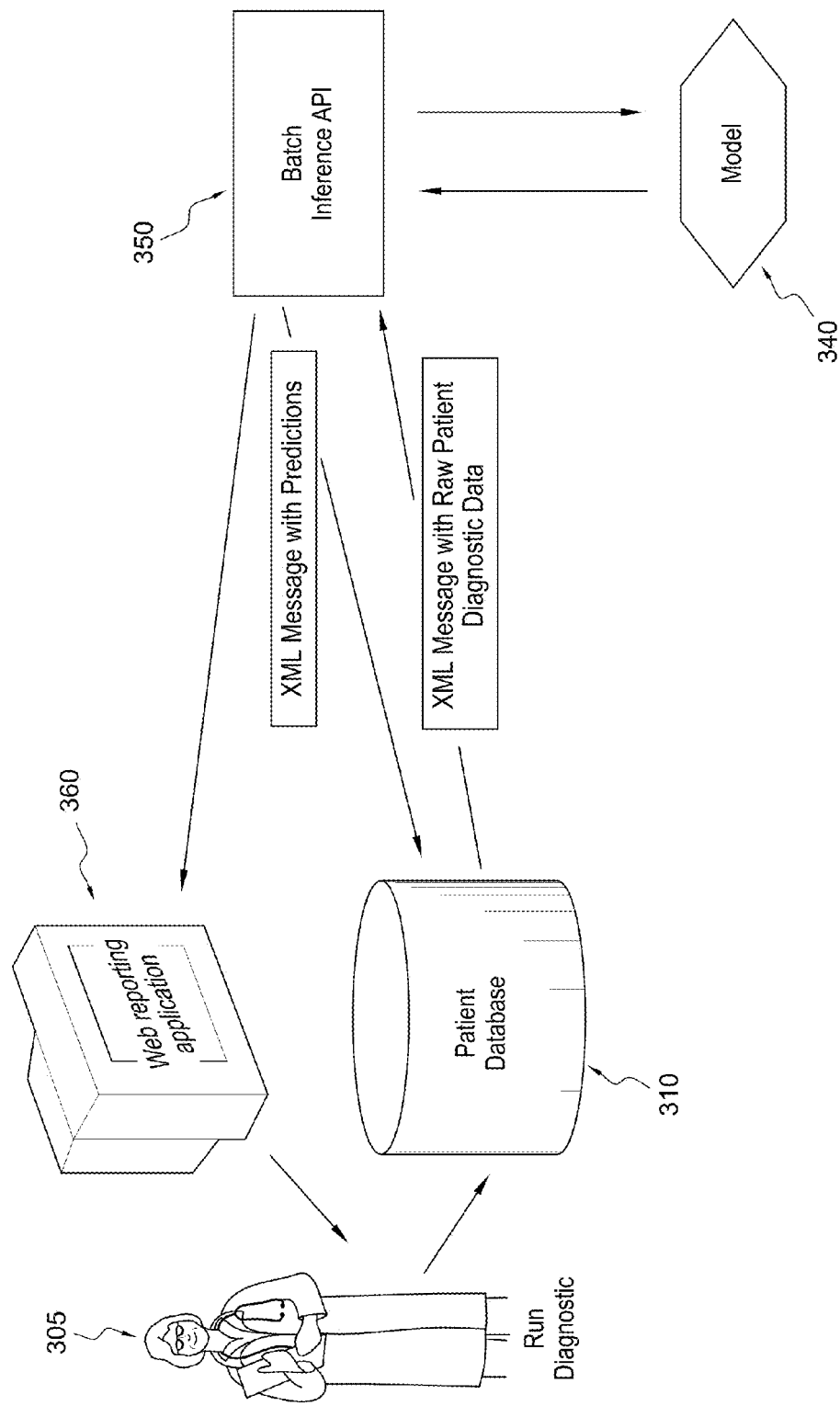
FIG. 3 illustrates a process for implementing the system according to an embodiment of the invention.

FIG. 3 illustrates a process flow for implementing a system for predicting a patient-specific probability of disease according to an embodiment of the invention. A clinician 310 runs diagnostic test(s) on a patient; and, results are written to a patient database 320 (also referred to herein as a "data warehouse" or "training database"). The database 320 sends, for example, an XML message with raw patient diagnostic data to a batch inference application programming interface (API) 330. The batch inference API 330 communicates with a model 340 (also referred to herein as the "BBN-ML") and receives a patient-specific prediction. The batch inference API 330 sends XML messages with the patient-specific prediction to the patient database 320 and a graphical user interface 350.

A. Malignant Thyroid Nodules

The following description provides examples of using the systems and methodologies of the embodiments of the invention for diagnosing malignant thyroid nodules. It is recognized, however, that the embodiments of the invention could be utilized to diagnose other organs and/or diseases, such as, for example transplant glomerulopathy and transplant outcome, wound healing, and breast cancer. One method uses available clinical information (e.g., patient age, ethnicity, thyroid functional status, surgeon pre-operative assessment, and/or number of cervical lymph nodes), available diagnostic information (e.g., fine needle aspiration biopsy results, nodule characterization by ultrasound, nodule size by ultrasound, and/or nuclear medicine rating), imaging technology (e.g., EIS), and a computer classification model (i.e., the BBN-ML).

The clinical and diagnostic (e.g., cytology and imaging) data is collected in the patient's electronic medical record. The EIS data is collected through an examination of the patient by the clinician. The combined data is used to train the BBN-ML, which is validated in at least one embodiment using cross-validation. The validated BBN-ML is used to calculate a probability that the pathology of an individual thyroid nodule is malignant or benign. The BBN-ML provides a probability distribution for the pathology of the nodule, along with an estimated accuracy, which includes sensitivity, specificity, positive and negative predictive value, and overall accuracy. The estimate can be calculated using at least two methods. The first method assembles the relevant data parameters into a tabular file which is read by software using an API, which returns posterior probabilities for outcomes of interest using all evidence in the tabular file. The second method employs a graphical user interface for a physician to enter data manually.

A vexing and common clinical problem is definitively diagnosing the cytologically indeterminate thyroid nodule. This often necessitates diagnostic operation in a large proportion of patients with so-called "follicular neoplasms" to possibly benefit the few patients with actual thyroid malignancy. Accurately predicting malignancy in any given thyroid nodule is a clinical challenge. An embodiment of the invention provides decision support tools and predictive models that are based on clinical, image-based, as well as cytological predictors of malignancy, to guide therapeutic decision making. The sensitivity and specificity derived using the BBN-ML provides a level of confidence and accuracy. The BBN-ML reduces the amount of unnecessary surgical operation with its attendant healthcare system costs and surgical morbidity impairing voice and swallowing function and quality of life. The BBN-ML is a prognostic risk assessment tool constructed and in at least one embodiment cross-validated, which provides an individual patient-specific prediction of cancer in thyroid nodules.

An embodiment of the invention utilizes a BBN-ML that compares known patient characteristics to known outcomes in the training population to arrive at a highly individualized, patient-specific estimate of risk of thyroid malignancy, rather than using generalized rules to assign the patient into a risk/survival pool. Although at least one embodiment of the invention creates the BBN-ML utilizing data collected in a clinical study of EIS on thyroid nodules before thyroidectomy [8, 9], it is recognized that training data may be obtained from other sources. A Bayesian classifier was trained on a prospectively enrolled cohort collected over a four year period (September 2002-December 2006) in the context of a previously published institutional review board (IRB) approved clinical trial including thyroid impedance, ultrasound imaging, cytological and histopathological outcome data [8, 9]. Thus, a prospective single arm observational cohort trial was used evaluating the diagnostic accuracy of pre-operative thyroid EIS in patients scheduled to undergo thyroidectomy.

In at least one embodiment of the invention, thyroid EIS was conducted prior to thyroid surgery using a T-Scan 2000ED (available from TransScan Medical (Mirabel®, Anchorage, Ak.)). Baseline conductivity and capacitance measurements of the sternocleidomastoid muscle were obtained. The thyroid gland was scanned in a high-resolution targeted mode with a flat multi-array thyroid probe held by the clinician while the patient held a metal cylinder. The source of a low-level and biocompatible (e.g., alternating current) electrical signal (e.g., 1.0 to 2.5 volts, maximum current 5 mA) was transmitted from the cylinder, up the arm, and across the neck. Impedance recordings of conductivity and capacitance were obtained over the entire thyroid gland in a predetermined sequence using a real-time image acquisition technique over a broad frequency range (e.g., frequency range, 50-20,000 Hz). A gray-scale impedance map was obtained that provides an anatomical image corresponding to the area of interest directed to a palpable or sonographic thyroid nodule.

Homogeneous gray scale impedance maps (uniform conductivity and capacitance) are characteristic of normal or benign thyroid nodules, which demonstrate similar conductivity and capacitance (or impedance) to normal thyroid tissue. A focal disturbance in the electrical field distribution can be seen by a malignant tumor due to its increased conductivity and/or capacitance (or decreased impedance), which appears as a focal bright white spot on the gray scale impedance map. Skin surface lesions and/or artifacts (e.g., incomplete probe contact, insufficient conducting gel, clavicular head) can appear as white spots as well. In order to arrive at an appropriate malignancy risk determination, the lesions and artifacts are taken into account and correlated with specific localization of the thyroid nodule(s). Changes from baseline sternocleidomastoid conductivity and capacitance are calculated for the thyroid nodule(s). A positive EIS examination is defined as a focal bright spot over a thyroid nodule, correlating with increased conductivity (decreased impedance) and/or capacitance greater than 25% of the baseline sternocleidomastoid muscle impedance, absent confounding local artifacts [8, 9].

An embodiment of the invention includes reviewing impedance scans conducted in the previous trial [8, 9], blinded to fine needle aspirate cytology and surgical pathology results. An EIS level of suspicion (LOS) score was developed on the basis of a focal white spot presence and increased conductivity and/or capacitance (with the previously established cutoff) associated with the palpable or sonographic thyroid abnormality. Thyroid nodule level of suspicion was classified as follows: LOS1: definitely benign; LOS 2: highly unlikely to be malignant; LOS 3: unlikely to be malignant; LOS 4: likely to be malignant; and, LOS 5: highly likely to be malignant. Thyroid nodules corresponding to a palpable or sonographic abnormality determined to have LOS of 4 or 5 was considered EIS-positive; otherwise the nodules were regarded as EIS-negative.

In one embodiment of the invention, the study subjects underwent thyroid resection after thyroid US, FNA, and EIS. Surgical histopathology was correlated with sonographic, cytological, and impedance findings and interpretations. FNAB and surgical specimens were evaluated by experienced board-certified cytologists and thyroid pathologists who rendered a cytological and histopathological diagnosis without knowledge of EIS level or suspicion for malignancy. In at least one embodiment, the study data was collected and curated into a data set consisting of 218 subjects. Biopsy results were classified based on established clinical guidelines into either benign or malignant diagnoses and assembled into a master data set. The master data set was randomized into additional (e.g., 10) cross-validation sets. Each subject record was assigned a randomly generated number. These numbers were used to assign the subjects to a number of test groups (e.g., 10). A matched training set was created for each test group, which excluded the test group.

In at least one embodiment, once the data set was prepared, the data for modeling was prepared using a discretization engine consisting of algorithms for curating the data prior to modeling. Discrete factors (e.g., binaries, text or qualitative data) were prepared using discrete binning, wherein each state in the field corresponded to a state in the distribution. Continuous factors (e.g., cost and length of stay) were prepared using a granular equal-probability-density binning approach that provided for stratification while acknowledging and controlling for the non-normal distributions observed in a clinical population. Thus, within the allowable range of a given feature with a continuous distribution, this method ensured that the prior probability distributions for each feature used for training the classifier had an equal population in each numeric range.

The predictive models are built by applying a set of heuristics to generate predictive models with different conditional independence assumptions. The conditional independence assumptions are represented as a directed acyclic graph, wherein the structure of the network represents a hierarchy of conditional independence which allows the user to identify the best estimators of a given outcome and also to identify other features that can act as proxies when critical prior probabilities are missing. The BBN-MLs encode the joint probability distributions of all of the variables in the clinical data set from the previous clinical trial by building a network of conditional probabilities [8, 9]. The BBN-MLs provide a network incorporating parent-child relationships between nodes. The network is queried to provide estimates for posterior probabilities given a priori knowledge, and tested for accuracy using data withheld from the training model. The predictive models are constructed using a machine learning algorithm (e.g., FasterAnalytics™ (available from DecisionQ, Washington, D.C.)) that supports a Minimum Description Length (MDL) scoring metric for network optimization. MDL scoring ensures that the final model represents the most likely model given the data used for learning and the model variations under consideration.

The machine learning algorithm allows the computer to learn dynamically from the data that resides in the data warehouse. The machine learning algorithm automatically detects and promotes significant relationships between variables without the need for human interaction using a scoring algorithm to optimize the network for robustness. This allows for the processing of vast amounts of complex data quickly and easily into a tractable Bayesian network. The structure of the network provides the user with immediate knowledge about the nature of the problem set and the relative significance of variables to the outcome of interest. By inputting current knowledge into the BBN-ML, the user obtains a probability of outcome and relative risk in real-time. Further, a graphical representation of the network is provided to the user. This provides the user with the likely rationale for the outcome of interest and knowledge about additional information used to confirm or refute the predicted outcome. An embodiment of the invention utilizes a step-wise modeling process to optimize the accuracy of the BBN-ML. The development of the BBN-ML is an iterative process consisting of several steps, the end product of which is a predictive model that supports subsequent dynamic re-training with new data. The process streamlines variable selection and preparation to produce the optimum outcome.

In at least one embodiment of the invention, model creation begins with preliminary modeling to identify appropriate machine learning parameters and data quality issues. A base level of association in the dataset and obvious associations that are interfering with the base level (confounding features) are also identified. Feature analogs (i.e., features that are proxies for one another and reduce accuracy) are identified and removed by the operator. Next, the operator uses the pruned features to train a new classifier in order to assess and set appropriate machine learning parameters. Appropriate changes are made to the data set, including the removal of analogs and confounding features and further binning. The model is explored relative to the literature and domain expertise as a "check" and to analyze relationships. Linear naïve modeling is also performed on dependent outcomes of interest to identify the relative contribution of features. A quantitative contribution report is also prepared in at least one embodiment.

Following the pruning and qualitative validation process, final focused modeling is performed, wherein heuristic search is performed using only subsets of variables identified in prior steps discussed in the previous paragraph. A network is obtained that is more focused than the network produced in the prior steps. By excluding certain variables, the remaining variables are explored more exhaustively. The focused model is explored and preliminary reports are automatically created. In at least one embodiment, manual modeling is also performed to enhance the focused model. Specifically, the structure of relationships is changed manually using a user interface to incorporate expert information beyond what the data contains.

Cross-validation is performed, wherein classifier is trained on each of the training sets created in the data preparation step using the same data discretization and modeling parameters. Each corresponding test set is used to create a set of case-specific predictions. Moreover, a ROC curve is plotted for each test exercise to calculate classification accuracy. In at least one embodiment, a 10% holdback dataset is withheld from the initial dataset to be used for prospective validation. Upon completion of cross-validation, the best model is documented in XML format for deployment as the BBN-ML. The relevant learning parameter and modeling log files are stored if audits are performed in the future. All cross-validation files are also stored for future audits; and, a report summarizing the results is prepared.

In at least one embodiment, the network is validated using a train-and-test ten-fold cross-validation methodology. Ten-fold cross-validation is performed, wherein ten unique sets of data are used that have been randomized in 90% train/10% test pairs. This produces classification accuracy estimates across ten exercises and calculates the classification error. Predictive values are calculated by classifying the outcome (i.e., surgical pathology diagnosis) for a given instance and comparing this prediction to the known value in an independent test set. The test set predictions are used to calculate a ROC curve and confusion matrix by threshold for each test set by the clinical feature of interest. The ROC curve is calculated by comparing the predicted value for each feature of interest to the known value in the test set on a case-specific basis. The ROC curve is used to calculate the area-under-the-curve (AUC), a metric of overall model quality, and positive predictive value (PPV), a measure of the probability that a positive is a true positive given a specified probability threshold for the variable of interest. The BBN analysis determines if a clinically relevant BBN-ML-derived prognostic risk assessment tool can be constructed and cross-validated.

Figure 4:
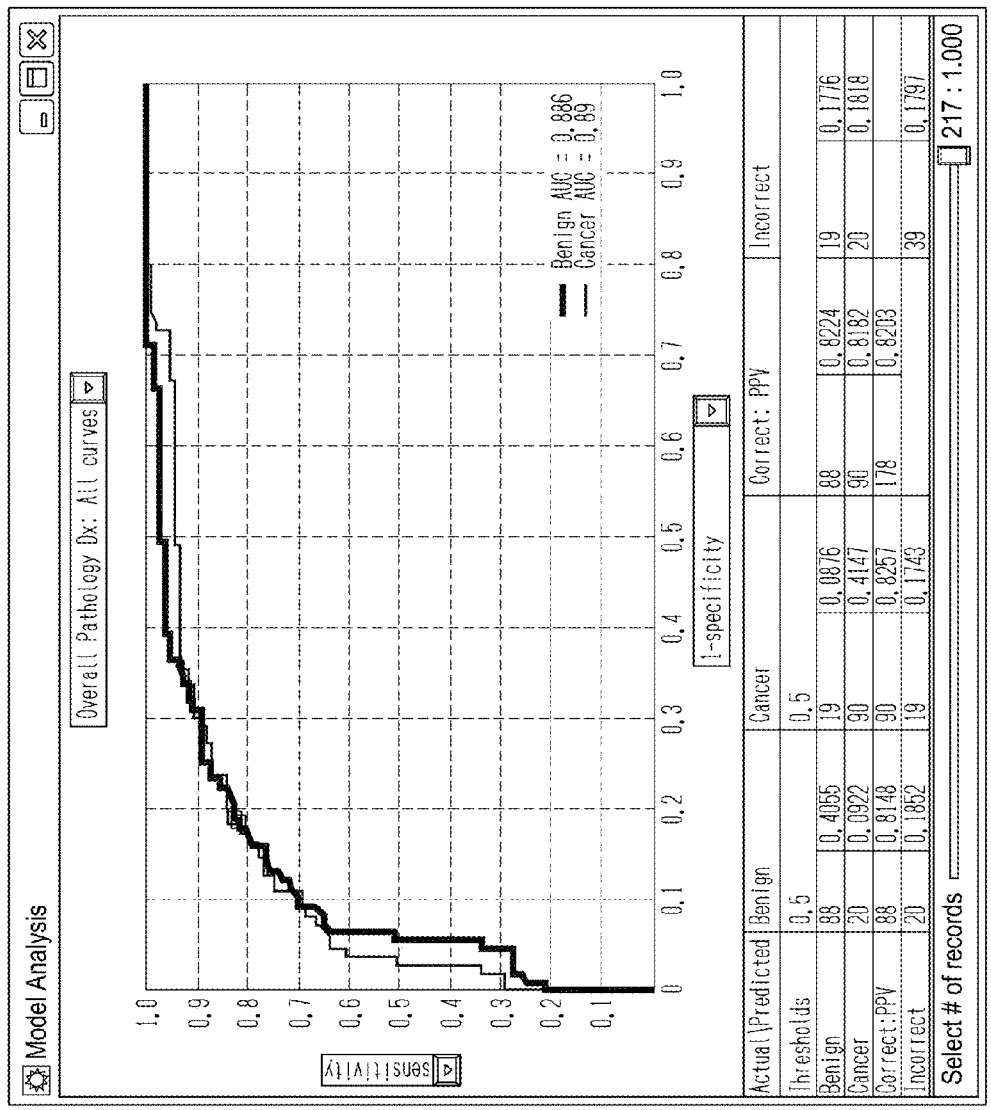
FIG. 4 illustrates a receiver-operating characteristic curve according to an embodiment of the invention.

According to one embodiment of the invention, FIG. 4 illustrates the ROC curve and predictive values for the BBN-ML as tested a posteriori with the master data set. The completed BBN-ML is cross-validated using the train and test sets and also tested a posteriori against the master data set to assess predictive power. FIG. 5 illustrates a table of the cross-validation results for each train-and-test pair and the a posteriori testing results according to an embodiment of the invention. Because the internal a posteriori testing results are very similar to the cross-validation results and the cross-validation results are internally consistent, it is accurate to describe this model as highly robust and highly predictive and it is appropriate to use the internal ROC curves. The model operates at an 80% negative predictive value (NPV) and an 83% PPV, as well as an 88% AUC for both outcomes (benign and malignant thyroid nodules).

Figure 6:
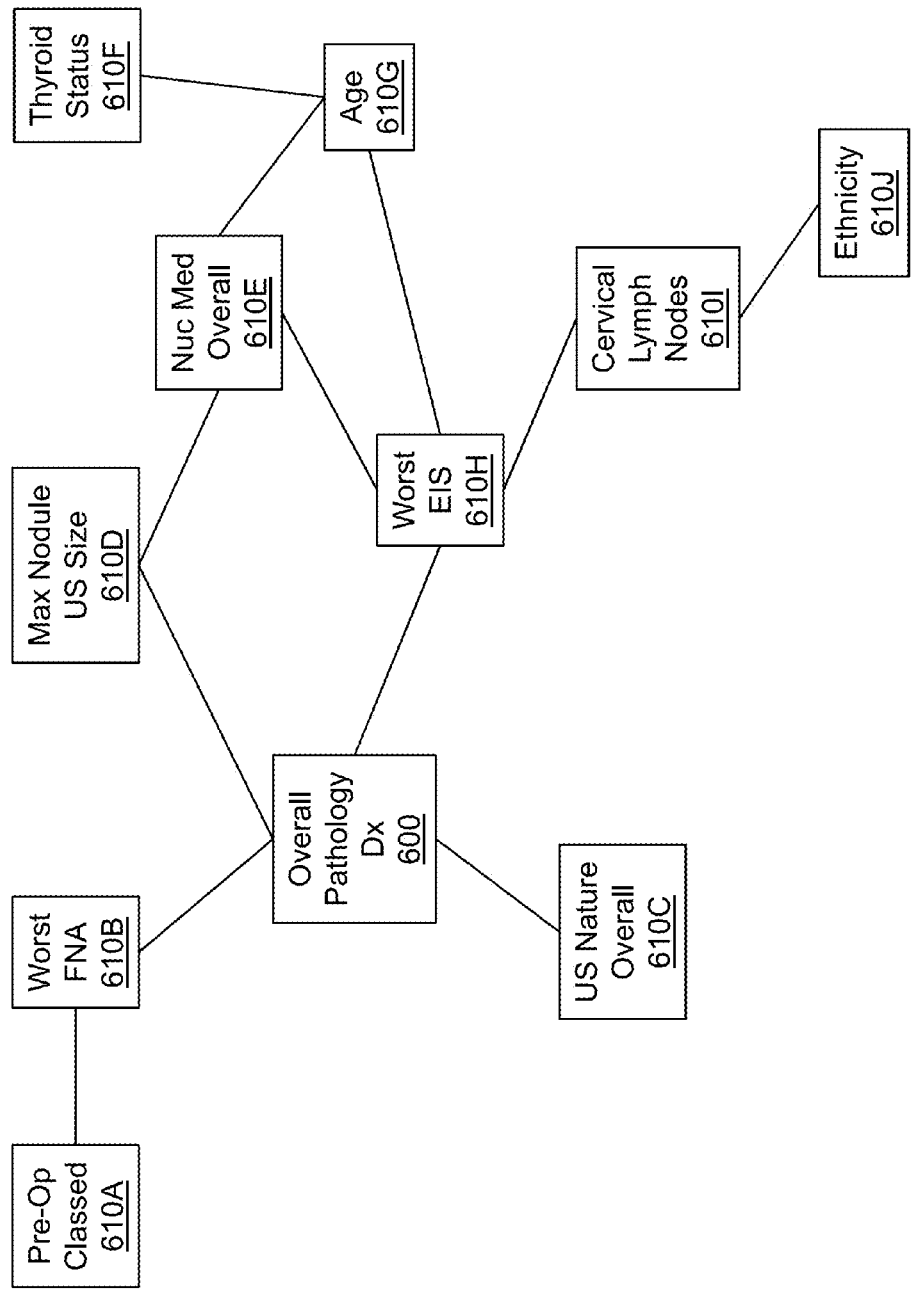
FIG. 6 illustrates the structure of the BBN network model according to an embodiment of the invention.

FIG. 6 illustrates the structure of a BBN-ML for predicting an overall pathology diagnosis (DX) 600 (i.e., benign or malignant thyroid) according to an embodiment of the invention. Predictors (also referred to herein as "clinical parameters") of the BBN-ML include pre-operative diagnosis 610A, worst FNA 610B, ultrasound nature overall 610C, maximum nodule ultrasound size 610D, nuclear medicine overall 610E, thyroid status 610F, age 610G, worst EIS 610H, cervical lymph nodes 610I, and ethnicity 610J. Because the BBN-ML provides an estimate of the probability diagnosis 600, whether a result is classified as benign or malignant is a function of the probability threshold used to determine whether a result is considered a positive or negative. Thus, the predictive values (NPV and PPV) are a function of the threshold used and can be optimized for the relative cost of Type I and Type II errors. In the cross-validation process described above, it was determined that a 50% threshold (most likely case) produced optimum results.

In one embodiment of the invention, the BBN-ML structure defines four predictors of thyroid nodule histopathology: FNA cytology (i.e., worst FNA 610B), maximum nodule size (i.e., maximum nodule ultrasound size 610D), EIS characteristics (i.e., worst EIS 610H), and ultrasound characteristics of the nodule (i.e., ultrasound nature overall 610C). The relative contribution of each of these four factors is determined by excluding each factor one at a time in a posteriori analysis against the master data set. When the worst EIS 610H predictor is eliminated from the BBN-ML, the AUC for benign and cancer is 84.2% and 84.6%, respectively, and the PV value (at 50%) for benign and cancer is 75.8% and 71.3%, respectively. When the worst FNA 610B predictor is eliminated from the BBN-ML, the AUC for benign and cancer is 88.0% and 83.0%, respectively, and the PV value (at 50%) for benign and cancer is 79.5% and 82.9%, respectively. Eliminating the ultrasound nature overall 610C predictor from the BBN-ML, yields a AUC for benign and cancer of 88.2% and 88.4%, respectively, and a PV value (at 50%) for benign and cancer of 80.4% and 81.6%, respectively. When the maximum nodule ultrasound size 610D predictor is eliminated from the BBN-ML, the AUC for benign and cancer is 92.0% and 91.9%, respectively, and the PV value (at 50%) for benign and cancer is 83.5% and 81.6%, respectively. The only predictor that significantly degraded the BBN-ML's predictive power when eliminated from the network is the worst EIS 610H predictor. Elimination of the maximum nodule ultrasound size 610D predictor improved the predictive power of the BBN-ML; thus, this predictor is included in the BBN-ML.

Figure 7A:
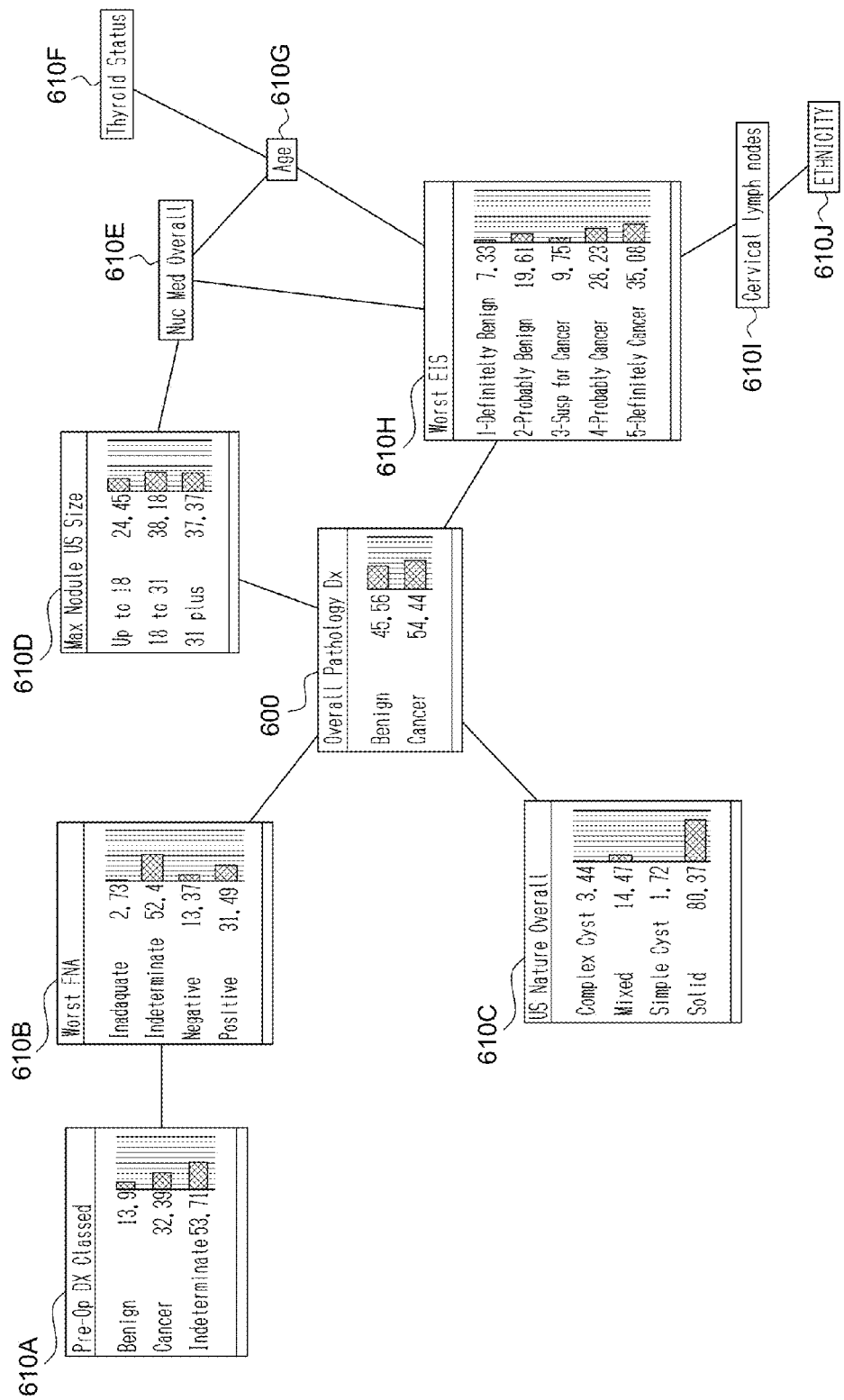
FIGS. 7A-7F illustrate BBN network models for predicting thyroid malignancy according to embodiments of the invention.

According to one embodiment of the invention, model structure is interpreted based on these results. First order predictors of thyroid pathology are FNA cytology 610B, ultrasound characteristics 610C, maximum nodule size 610D, and EIS characteristics 610H of the thyroid nodule. Diagnosis 600 is conditionally dependent with FNA cytology 610B, as FNA is incorporated in pre-operative diagnosis. Furthermore, patient age, thyroid nodule size, scintigraphic findings (hot, warm, cold), and EIS characteristics are clustered together in a conditional dependence network. The conditional dependence between these factors accounts for the potential overlap of predictors and prevents over-fitting of the BBN-ML to the data. This supports the overall robustness of the BBN-ML. In at least one embodiment, as the training database is updated and new knowledge is interpreted, the structure of the BBN-ML (i.e., dependency relationships between the nodes) is revised by the heuristic search and scoring algorithms. FIG. 7A illustrates the expected reference probability distributions for each variable (i.e., 610A-610J) in the training population according to an embodiment of the invention. Each reference distribution represents the expected distribution of a given model feature in a normal pre-operative population similar to the study population utilized herein, prior to the addition of knowledge about an individual case.

Figure 7B:
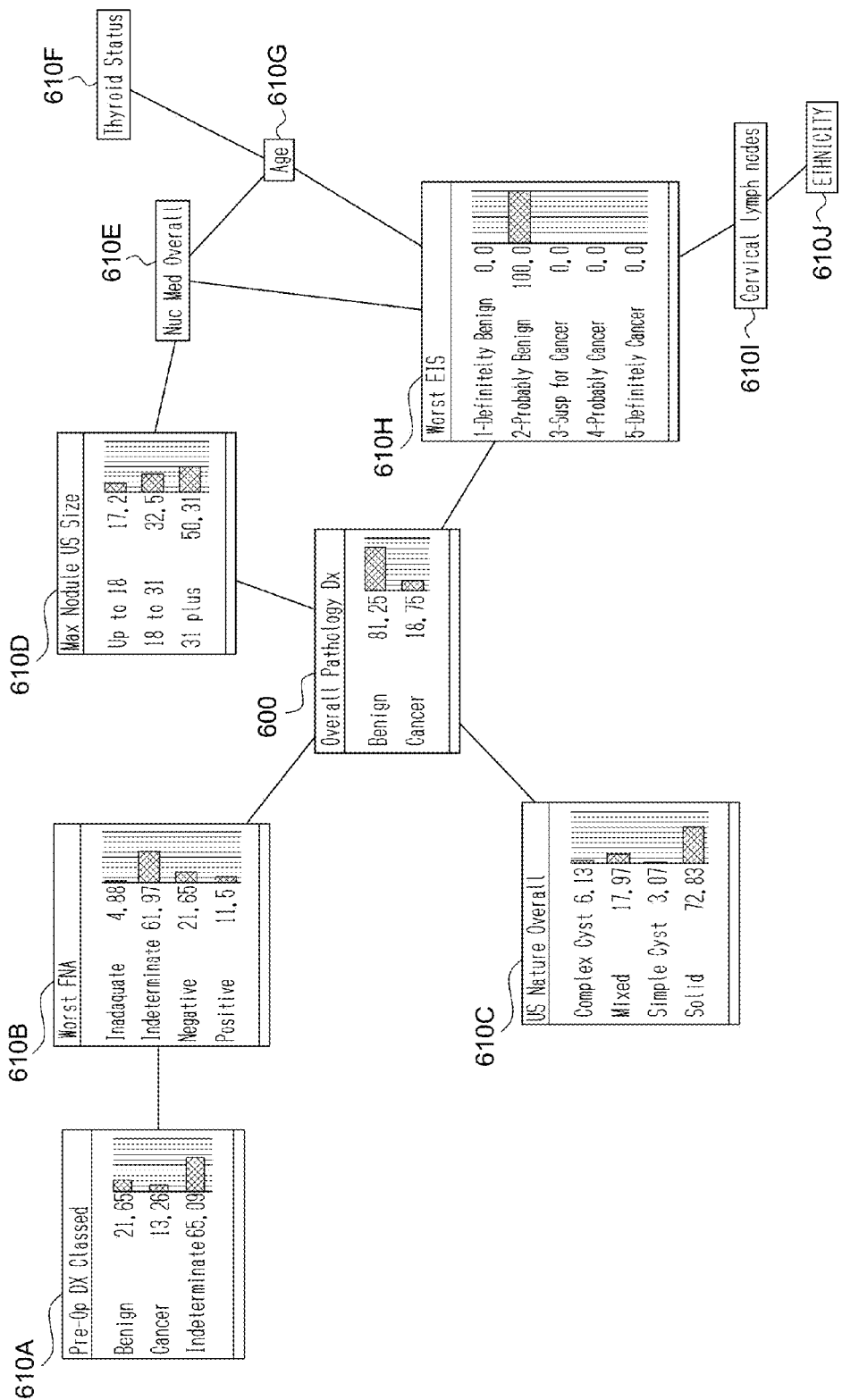

With a trained, tested, and cross-validated BBN-ML, case-specific predictions are made by adding prior knowledge about a given case, such as, for example an EIS result (i.e., worst EIS 610H) or ultrasound characterization of a thyroid nodule (i.e., US nature overall 610C). FIG. 7B illustrates a posterior estimate of surgical pathology outcome according to an embodiment of the invention. The final estimated pathology diagnosis 600 for a given case with thyroid nodule EIS level of suspicion of 2 (worst EIS 610H=highly unlikely to be malignant) has a posterior probability of cancer of 19%.

Figure 7C:
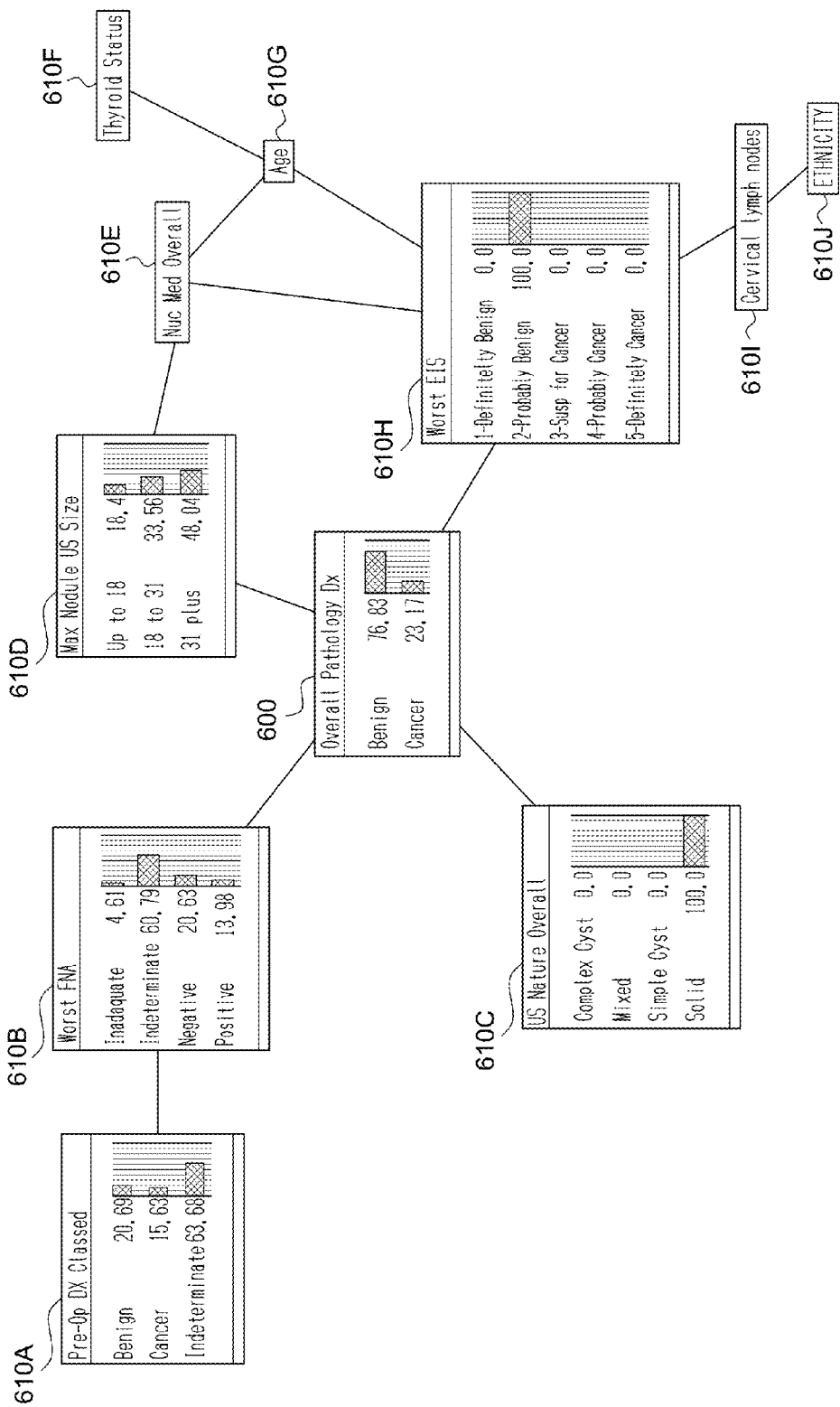
Figure 7D:
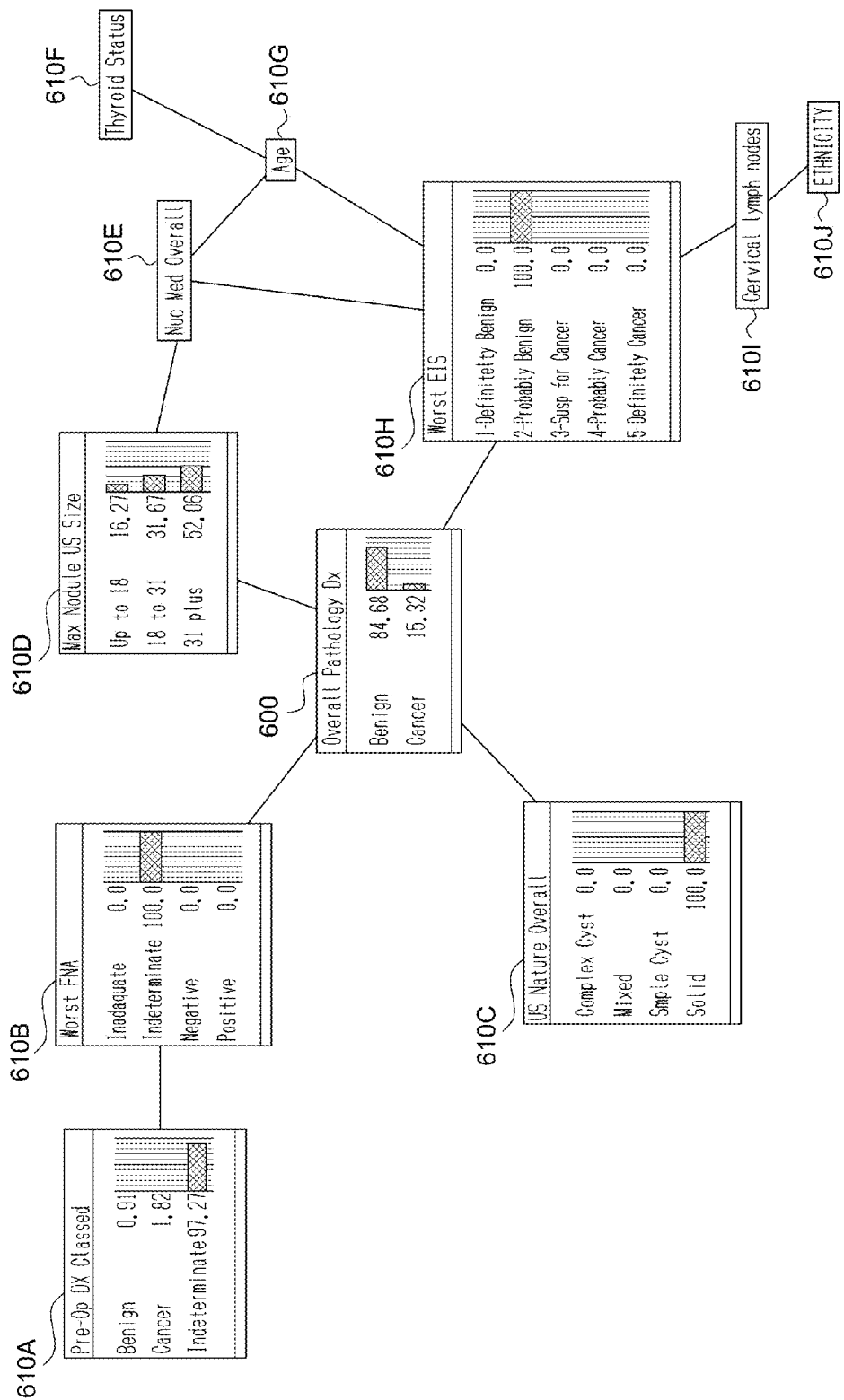
Figure 7E:
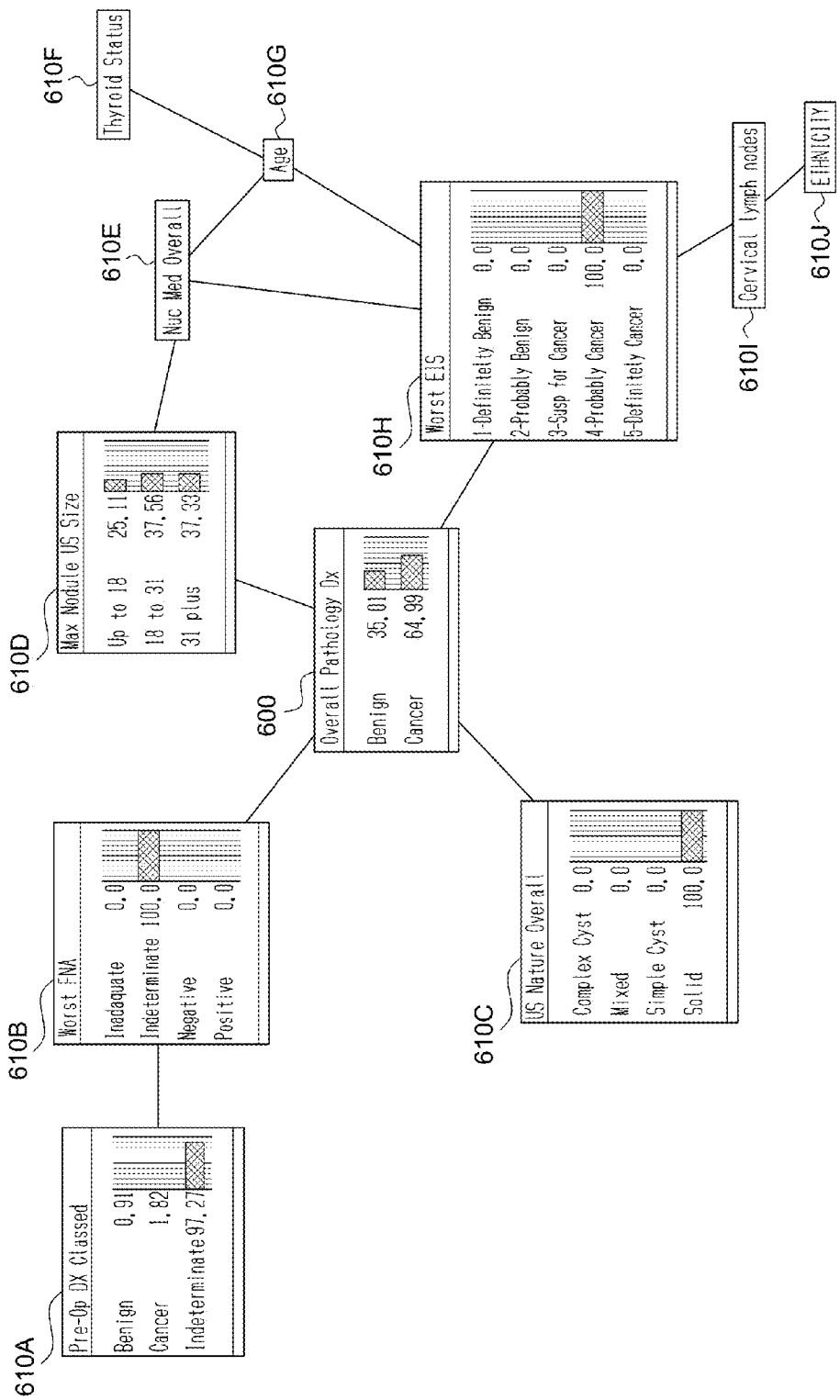

As illustrated in FIG. 7C, adding a thyroid nodule ultrasound finding 610C of solid to the EIS level of suspicion 610H of 2 refines the case-specific posterior estimate of malignancy 600 to 23%, which is less than the cancer rate in the study population (54%). Additional data refines the prediction of malignancy 600 even further, such as an indeterminate FNA cytology 610B. As illustrated in FIG. 7D, a solid nodule by ultrasound 610C having an EIS level of suspicion 610H of 2 has a posterior probability of benignity 600 of 85% (15% probability of malignancy). Further, as illustrated in FIG. 7E, changing the EIS result 610H from probably highly unlikely to be malignant to level of suspicion of 4 (likely to be malignant) increases the posterior probability of malignancy 600 from 15% to 65%.

Figure 7F:
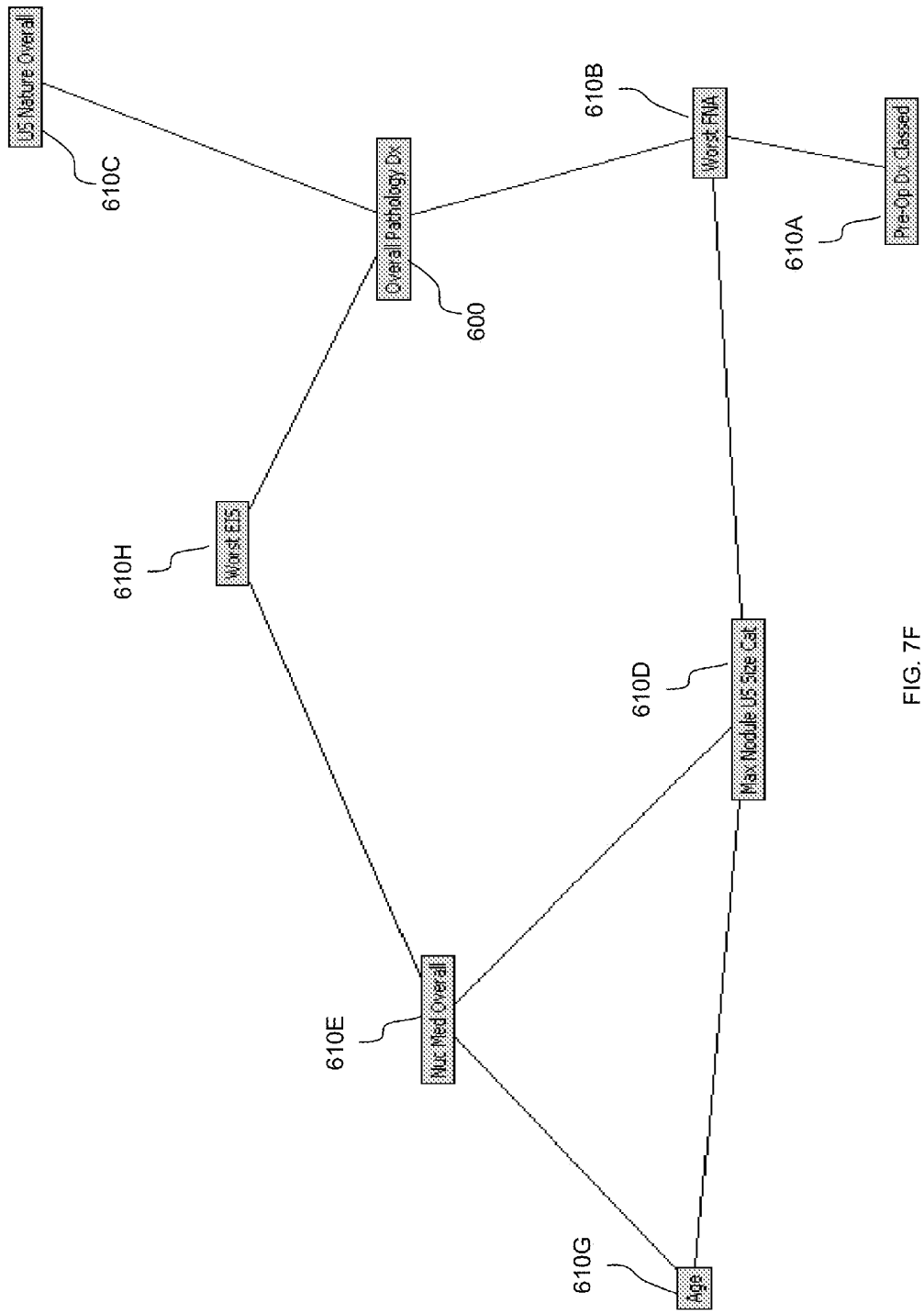

As described above, the conditional dependency of the predictors 610A-610J, and thus the configuration of the nodes in the BBN-ML can change depending upon the data in the training database. FIG. 7F illustrates a BBN-ML for predicting malignancy in a thyroid nodule according to another embodiment of the invention, wherein US nature overall 610C, worst EIS 610H, and worst FNA 610B are the first order predictors of thyroid pathology. Worst FNA 610B is conditionally dependent upon pre-op Dx classed 610A and maximum nodule US size 610D. Nuclear medicine overall 610E can be used to predict worst EIS 610H; and, age 610G can be used to predict nuclear medicine overall 610E and maximum nodule US size 610D. Moreover, maximum nodule US size 610D and nuclear medicine overall 610 E are conditionally dependent upon one another.

Inference-based individual case-specific estimates of posterior probability from the Bayesian Belief Network can be attained by applying the BBN-ML to new data sets in either batch inference mode or by tabulating all potential combinations in an inference table. FIG. 8 illustrates an inference table calculated using the BBN-ML for all potential combinations of EIS 610H and FNA 610B results according to an embodiment of the invention. For example, in row 6 of the table, a Definitely Benign EIS (Level of Suspicion of 1) and an Indeterminate FNA cytology has a frequency estimate of 4.7% in the population and a probability of cancer of 5.7%. However, in row 9 of the table, a patient with an indeterminate nodule with an EIS Level of Suspicion of 4 (likely to be malignant) has a 13.6% estimated frequency in the training population and a 58.7% probability of thyroid malignancy.

Figure 9:
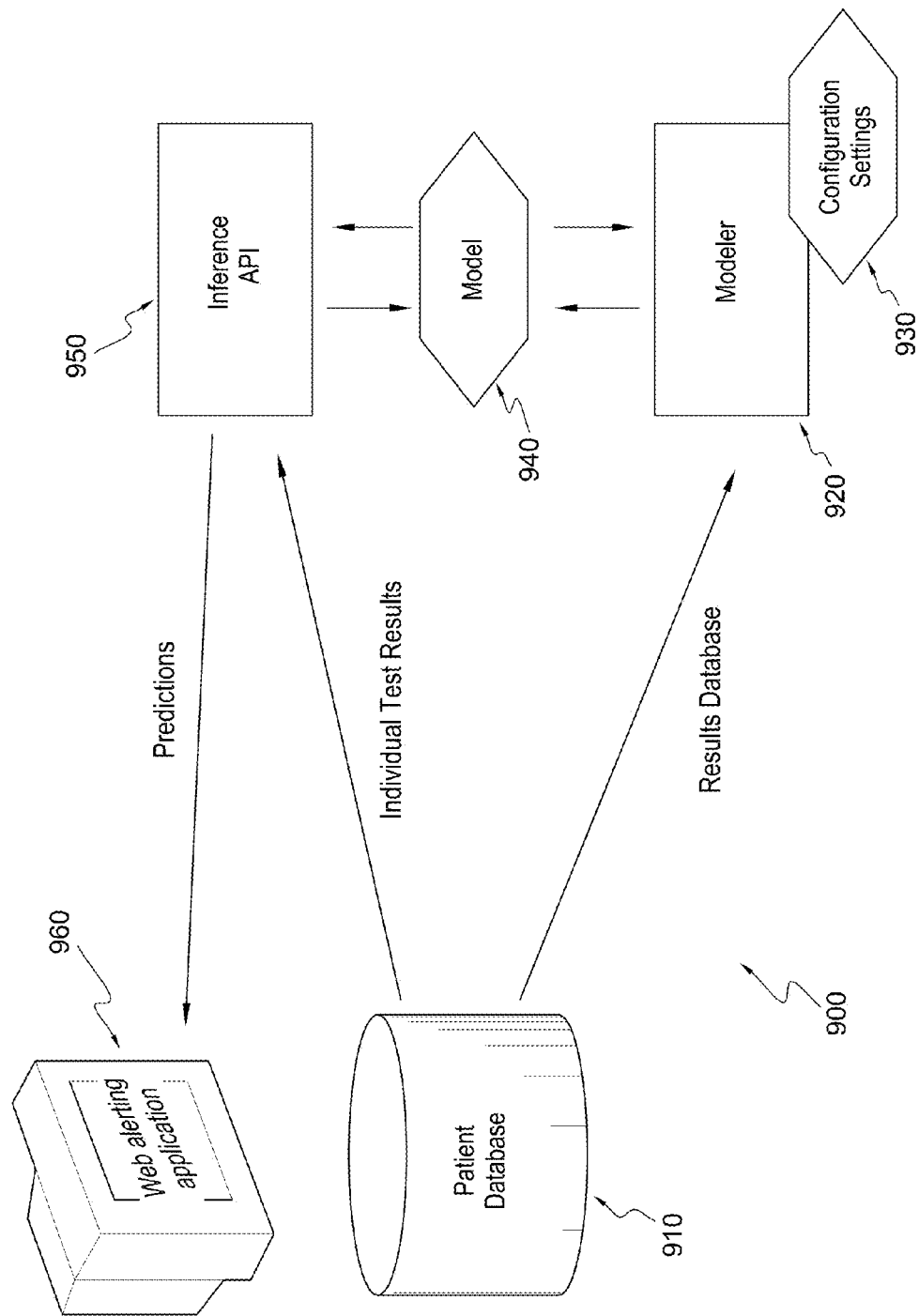
FIG. 9 illustrates a system for pre-operatively determining a patient-specific probability of malignancy in a thyroid nodule according to an embodiment of the invention.

FIG. 9 illustrates a system 900 for pre-operatively determining a patient-specific probability of malignancy in a thyroid nodule according to an embodiment of the invention. A patient database 910 includes individual patient records. This can either be a standalone database or an existing clinical information system, such as an electronic health record database. The system 900 uses patient data to train new iterations of the model 940 (also referred to herein as the "BBN-ML") and to make individual patient predictions.

Machine learning software 920 is also used to retrain the model 940 with new data. The machine learning software 920 includes a configurations file 930, which contains the settings for learning. The model 940 is an XML model that specifies structure and joint probability distributions. The batch inference API 950 uses the model 940 and individual patient data from the patient database 910 to produce patient-specific predictions. A graphical user interface (GUI) 960 (e.g., web-based or client-server) receives the patient-specific predictions in the form of reports.

B. Transplant Glomerulopathy

Another embodiment of the invention inputs real-time PCR data into the BBN-ML to predict biomarker expression in renal allograft biopsy specimens. The biomarker expression is highly predictive of renal transplant glomerulopathy versus stable allograph function. The BBN-ML analyzes large datasets of diverse data types to identify associations between clinical, genomic, and proteomic variables. Use of the BBN-ML is extendable to define surrogate marker profiles of specific pathologies within renal allografts using biological products of gene expression found in blood, serum, urine, and/or tissue biopsies as surrogate endpoints.

At least one embodiment of the invention utilizes gene expression data from allograph biopsies to create a network of Bayesian models. The most robust model is documented in XML format for deployment as the BBN-ML. As described below, the Bayesian models are in an interactive format such that a clinician can select an outcome or relative gene expression level by clicking on the graphical user interface and observing corresponding changes to the probability distribution of the remaining variables. The graphical user interface is also used to enter current, patient-specific data and receive an evidence-based prediction of diagnosis (e.g., transplant glomerulopathy or stable function), thus enabling patient-risk stratification and clinical intervention.

An embodiment of the invention built the network of Bayesian models based on a retrospective review of 963 renal transplant core biopsies from 166 patients. It is recognized, however, that other studies could be utilized to build the network of Bayesian models. The review of 166 patients identified transplant glomerulopathy in 20 biopsies from 18 patients using (10.8%) Banff classification. The mean grade (±SD) of transplant glomerulopathy was 2.65±0.49. A cohort of patients (n=32) with stable function allografts were studied for comparison. The biopsies were analyzed for transcript expression of 87 genes, across two gene panels, with quantitative real-time PCR. An embodiment of the invention derives relative transcript quantification using quantitative, real-time PCR and the $2^{-Ct}$ method [70]. This calculation was performed with normalization to 18S ribosomal RNA expression as an internal control per sample and is relative to pooled cDNA from live donors undergoing open donor nephrectomy. Data was analyzed (e.g., using the machine learning algorithm) and dependence relationships between transcript expression and transplant glomerulopathy was established. A probabilistic Bayesian model was generated for each gene panel and validated to predict histopathology based on gene expression signatures (e.g., FIGS. 10A-C and FIG. 11A-C). Ten non-overlapping sets of ten percent of the biopsies were excluded randomly from the initial dataset (i.e., 90% train, 10% test) and subsequently used for a ten-fold cross-validation of model robustness. In the validation analysis, the Gene Panel 1 Bayesian model effectively identified stable function versus transplant glomerulopathy with an overall sensitivity of 87.5% and a specificity of 85.7%. The Gene Panel 1 also yielded a PPV of 77.8% and a NPV of 92.3%. The Gene Panel 2 model was just as robust with 84.4% sensitivity and 80.0% specificity. The Gene Panel 2 also yielded a PPV of 87.1% and a NPV of 76.2%.

FIGS. 10A-C illustrate Bayesian models of relative-fold expression changes in a panel of genes related to immune function (i.e., Model 18b, Gene Panel 1) according to an embodiment of the invention. The Gene Panel 1, in this example, includes the following genes: ICAM1, IL10, CCL3, CD86, CCL2, CXCL11, CD80, GNLY, PRF1, CD40LG, IFNG, CD28, CXCL10, CCR5, CD40, CTLA4, TNF, CXCL9, CX3CR1, FOXP3, EDN1, CD4, TBX21, FASLG, C3, CD3E, CXCR3, and CCL5 (i.e., variables 1020A-1020AB, respectively). In the Bayesian model illustrated in FIG. 10A, diagnosis 1010 is divided into stable function (SF) or transplant glomerulopathy (TG). Probability distributions are shown immediately left of the bar graph. For instance, the diagnosis 1010 has a 39.38% probability of SF and a 60.62% probability of TG. Variables (also referred to herein as "clinical parameters" or "predictors") 1020A-1020M are divided into three equal-area bins of fold expression relative to pooled normal kidney expression levels. These ranges are derived by normalizing the available range of information into units contained equal densities of observations. For instance, for the variable 1020A, 32.21% of the patients in the training database have a ICAM1 gene expression level less than 1.04 relative fold expression; 32.12% of the patients in the training database have a ICAM1 gene expression level between 1.04 and 1.84 relative fold expression; and 35.67% of the patients in the training database have a ICAM1 gene expression level greater than 1.84 relative fold expression. The dotted box 1000 indicates a subset of genes (i.e., 1020A-1020I) for the focus illustrated in FIGS. 10B and 10C. In at least one embodiment, the ranges are derived by normalizing the available range of information into unit ranges such that each range contains equal numbers of observations.

A diagnosis 1010 of SF is associated with a down regulation of gene expression or only small increases in gene expression. For instance, as illustrated in FIG. 10B, the upper binned expression levels for variables 1020A-1020I (i.e., genes ICAM1, IL10, CCL3, CD86, CCL2, CXCL11, CD80, GNLY, and PRF1) are: >1.04=9.09%; >22.9=9.09%; >3.15=9.01%; >8.89=17.48%; >1.19=23.13%; >106=23.14%; >20.6=26.97%; >18.6=29.6%; and >22.9=31.63%, respectively. On the other hand, a diagnosis 1010 of TG is associated with increased expression of several genes within the biopsies. For instance, as illustrated in FIG. 10C, the upper binned expression levels for variables 1020A-1020I are: >1.04=52.94%; >22.9=52.94%; >3.15=52.7%; >8.89=47.2%; >1.19=43.52%; >106=48.53%; >20.6=41.06%; >18.6=39.38%; and >22.9=39.12%, respectively.

In regards to the variable 1600A discussed above with reference to FIG. 10A, changing the diagnosis 1010 to 100% stable function automatically adjusts the expected expression levels for the ICAM1 gene. Thus, for a patient with stable function, the Bayesian model estimates a 72.73% probability that the patient would have an ICAM1 gene expression level less than 1.04 relative fold expression. Moreover, the Bayesian model estimates an 18.18% probability that the patient would have an ICAM1 gene expression level less between 1.04 and 1.84 relative fold expression and a 9.09% probability of an ICAM1 gene expression level greater than 1.84 relative fold expression.

FIGS. 11A-C illustrate Bayesian models emphasizing surrogate biomarkers over a current C4d grade in predicting transplant glomerulopathy (Model 19b, Gene Panel 2) according to an embodiment of the invention. The Gene Panel 2 in this example includes the following genes: VCAM1, MMP9, Banff C4d, MMP7, LAMC2, TNC, S100A4, NPHS1, NPHS2, AFAP, PDGF8, SERPINH1, TIMP4, TIMP3, VIM, SERPINE1, TIMP1, FN1, ANGPT2, TGFB1, ACTA2, TIMP2, COL4A2, MMP2, COL1A1, COL3A1, GREM1$_{13}$ 2, SPARC, IGF1, SMAD3, HSPG2, FN1, ANGPT2, TGFB1, ACTA2, THBS1, CTNNB1, FGF2, TJP1, FAT, CDH1, SMAD7, CD2AP, CDH3, CTGF, ACTN4, SPP1, AGRN, VEGF, and BMP7 (variables 1120A-1120AT, respectively). The dotted box 1100 indicates a subset of variables (i.e., variables 1120A-1120E) for the focus of the Bayesian models illustrated in FIGS. 11B and 11C.

Banff C4d 1120C is an immunohistochemical stain used in transplantation. It is associated with transplant glomerulopathy. The probability of case is the probability of that scenario occurring in the dataset. Model grade of C4d staining (Banff C4d 1120C), along with expression patterns of genes related to endothelial activation and fibrosis, yielded a Bayesian model that accurately related a higher grade with transplant glomerulopathy (FIG. 11A; diagnosis 1110=TG probability of 81.25%). However, this Bayesian model further illustrates that transplant glomerulopathy biopsies (100% for 3.0 fold expression) have a fairly even distribution of C4d grades, thereby suggesting a high rate of false negatives for this variable alone (FIG. 11B; diagnosis 1110=TG probability of 100.00%). Elevated expression of the MMP7 1120D and LAMC2 1120E genes is more clearly related to a diagnosis 1110 of transplant glomerulopathy. Setting MMP7 1120CD and LAMC2 1120E with knowledge of their coincident expression levels indicates a 96.64% probability of transplant glomerulopathy (FIG. 11C).

FIGS. 12A-C illustrate Bayesian models for determining the probability of transplant glomerulopathy (i.e., diagnosis 1210) using relative-fold expression of the ICAM1, IL10, CCL3 and CD86 genes (variables 1220A-1220D, respectively) (Model 18b, Gene Panel 1) according to an embodiment of the invention. Given known, relative expression levels of genes, both directly and indirectly related to the diagnosis 1210, the Bayesian models provide a biopsy-specific outcome estimate. Coincident upregulation of the ICAM1, IL10, and CCL3 genes (variables 1220A-1220C, respectively) is indicative of transplant glomerulopathy (FIG. 12A; diagnosis 1210=TG probability of 99.67%). Additionally, upregulation of the CD86 gene (variable 1220D) of 8.89-fold or greater estimates the probability of transplant glomerulopathy as 81.61% (FIG. 12B). The interactive Bayesian models quickly bring to light biological pathways as illustrated by the adjusted probability distributions throughout the models when known evidence is set.

A clinician interested in describing the biological pathways closely associated with stable function versus those associated with transplant glomerulopathy utilizes the Bayesian models to elucidate potential targets by setting evidence of diagnosis to either option, which is done by clicking on the graphs (i.e., adjusting the cross-hatched bars in the diagnosis box 1210). The respective changes in posterior probability distributions (changes in cross-hatched bars in the gene boxes, relative to the cross-hatched bars FIG. 10A and FIG. 11A) instantaneously reports the coordinated dependence of each variable on the specific diagnosis. In other words, the clinician can adjust the diagnosis to either TG or SF by clicking on the cross-hatched bars in the diagnosis box 1210. This automatically adjusts the cross-hatched bars in the gene boxes, respective to the new diagnosis.

Conversely, setting known relative expression levels of genes immediately yields a posterior estimate of diagnosis. In other words, adjusting the relative expression level of a gene by clicking on a cross-hatched bar in one of the gene boxes automatically adjusts the diagnosis in diagnosis box 1210. For instance, FIG. 12A illustrates that the current dataset (by up regulation of ICAM1, IL10, and CCL3 gene expression relative to pooled normal renal biopsies) yields a diagnosis 1210 of 99.67% likelihood of transplant glomerulopathy. When the upper expression level of the CD86 gene is adjusted from 72.74 (FIG. 12A) to 100.00 (FIG. 12B), the diagnosis 1210 is automatically adjusted to an 80.61% likelihood of transplant glomerulopathy.

A subset (43/52) of the biopsies in the study utilized herein has been stained for peritubular C4d deposition, which was identified in 15/18 (83.3%) with transplant glomerulopathy and 8/25 (32.0%) with stable function (p<0.001). A Banff C4d grade of 3 is strongly associated with the presence of transplant glomerulopathy (81% probability in FIG. 11A). Additional genes (e.g., matrix metallopeptidase 7 (MMP7) and laminin (gamma 2; LAMC2)) are more likely to be associated with transplant glomerulopathy (FIG. 11B) and together predict transplant glomerulopathy with a higher probability (96% probability in FIG. 11C). A current quantitative marker of transplant glomerulopathy (the Banff C4d grade) does not identify the subset of transplant glomerulopathy cases that were identified via histology. Thus, the BBN-ML considers a more complete picture of transplant status (e.g., MMP7 and LAMC2) to correctly diagnose the biopsies with transplant glomerulopathy.

A Banff C4d deposition grade of 0.0 has a 44.7% probability of case, an SF probability of 83.9%, and a TG probability of 16.1%. The probability of case is the estimated probability of the scenario occurring in the study population. A Banff C4d deposition grade of 1.0 has a 24.8% probability of case, an SF probability of 41.9%, and a TG probability of 58.1%. A Banff C4d deposition grade of 2.0 has a 19.4% probability of case, an SF probability of 53.6%, and a TG probability of 46.4%; and, a Banff C4d deposition grade of 3.0 has a 11.1% probability of case, an SF probability of 18.8%, and a TG probability of 81.2%. FIG. 13 is a table illustrating stable function versus transplant glomerulopathy using the Laminin and Matrix Metalloproteinase-7 genes according to an embodiment of the invention. Rather than only having access to two values of C4d (grade 0 or grade 3) to reliably differentiate between stable function and transplant glomerulopathy, an embodiment of the invention enables the clinician to make a diagnosis based on a comprehensive picture of the individual patient's current status. This is then interpreted into an outcome that is described by multiple, interdependent variables (FIG. 13). Molecular pathways associated with transplant glomerulopathy are also identified.

In addition to post-transplant renal biopsies, gene expression changes can be followed in urine sediment, peripheral white blood cells, and renal allograft biopsies before and during reperfusion to evaluate allografts. In at least one embodiment of the invention, the predicted disease-specific outcome includes acute rejection, chronic allograft dysfunction, delayed graft function, and/or medium term allograft survival likelihoods.

C. Impaired Wound Healing

Another embodiment of the invention inputs data into the BBN-ML to predict the probability of impaired wound healing using biomarkers. More specifically, probabilistic predictive networks are utilized to assess the healing rate of an acute traumatic wound based on the expression level of related biomarkers such as cytokines, chemokines, and/or other gene RNA transcripts and translation products.

Methods are provided for determining wound healing via quantification of a set of biomarkers, or a subset thereof. Sample biomarkers may include selected translation products (cytokines and/or chemokines) in a patient's serum and/or wound effluent, as well as RNA transcripts of selected genes from the patient's wound-bed tissue. A BBN-ML is trained using the sample data, which compares a sample biomarker profile to the biomarker profiles of a patient population with known wound healing outcomes. An expected wound healing rate and patient-specific probability of wound outcome are calculated using the BBN-ML.

Cytokine and chemokine expressions provide an insight into the molecular pathogenesis of acute wound failures. The balance between pro- and anti-inflammatory mediators during wound repair is a factor in achieving tissue homeostasis following injury [37]. The inflammatory response supplies signals for cellular repair and is the first of several overlapping processes that constitute wound healing. However, an exaggerated inflammatory response is deleterious to wound healing. The pathogenesis of chronic wounds is a failure to progress through the normal stages of wound healing, wherein the wounds remain in a state of chronic inflammation [38]. Acute wound failures are the likely result of a detrimental response to injury. Overproduction of the inflammatory cytokines is seen in posttraumatic inflammation [39-41]. Multiple studies in trauma populations demonstrate correlations between inflammatory cytokines and negative outcomes [42, 43]. Increased IL-6, in particular, is an independent risk factor of morbidity and mortality in trauma patients [44, 45]. The anti-inflammatory cytokine IL-10 is also over-expressed in injured patients and is correlated with posttraumatic septic events [46, 47].

In at least one embodiment of the invention, a set of cytokines and/or chemokines are selected as biomarkers for determining wound healing based on their strong associations with wound outcome. Serum/wound effluent samples are collected from a patient at different time points during treatment. The levels of biomarkers in each patient serum and/or wound effluent sample are quantified and entered into the BBN-ML for statistical analysis, which determines the probability of wound outcome. The BBN-ML is constructed using reference biomarker profiles from a patient population with similar wounds and having known wound healing outcomes. In at least one embodiment, the selected cytokines and/or chemokines include IL-1$\alpha$, IL-1$\beta$, IL-2, IL-3, IL-4, IL-5, IL-6, IL-7, IL-8, IL-10, IL-12(p40), IL-12(p70), IL-13, IL-15, IP-10, Eotaxin, IFN-$\gamma$, GM-CSF, MCP-1, MIP-1$\alpha$, RANTES, and TNF$\alpha$, or any subset thereof.

In another embodiment of the invention, the expression profile of selected genes from a patient wound bed biopsy sample are quantified. The sample may be prepared in a number of ways, as is known in the art, e.g., by mRNA isolation from cells where the isolated mRNA is used as is, amplified, employed to prepare cDNA, cRNA, etc., as is known in the differential expression art. The sample is typically prepared from cells or tissue harvested from a subject to be diagnosed, using standard protocols, where cell types or tissues from which such nucleic acids may be generated include any tissue in which the genetic expression pattern to be determined exists.

A number of methods for detecting and/or quantifying the expression level of an RNA or protein in a sample are available in the art and can be employed in the practice of this aspect of the invention. For example, hybridization assays including Northern blotting techniques, hybridization to oligonucleotide probe arrays, oligonucleotide probe microarrays, in situ hybridization, nucleic acid amplification (e.g., reverse transcriptase-polymerase chain reaction, RT-PCR) and other analytical procedures can be employed.

While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled is employed. In these assays, a sample of target nucleic acids is first prepared from the initial sample of interest, where preparation may include labeling of the target nucleic acids via a variety of signal producing system, e.g., coupled fluorescence. Following target nucleic acid sample preparation, the sample is contacted with the array under hybridization conditions, whereby complexes are formed between target nucleic acids and complementary to probe sequences that are attached to the array surface. The presence of hybridized complexes is then detected, either qualitatively or quantitatively.

In at least one embodiment, expression profiles are generated using an array of "probe" nucleic acids, which includes a probe for each of the phenotype determinative genes whose expression is contacted with target nucleic acids, as described above. Contact is carried out under hybridization conditions, and unbound nucleic acid is removed. The resultant pattern of hybridized nucleic acid provides information regarding expression for each of the genes that have been probed, where the expression information is in terms of whether or not the gene is expressed and, typically, at what level, where the expression data (i.e., expression profile) may be both qualitative and quantitative. Alternatively, non-array based methods for quantitating the levels of one or more nucleic acids in a sample may be employed, including quantitative PCR, and the like. Where the expression profile is a protein expression profile, any convenient protein quantitation protocol may be employed, where the levels of one or more proteins in the assayed sample are determined. Representative methods include, but are not limited to, proteomic arrays, flow cytometry, standard immunoassays, etc.

An embodiment of the invention provides a method for identifying biomarkers that impact wound healing. More specifically, the method studied U.S. service members that sustained penetrating injuries to one or more extremities. Up to three wounds per patient were studied. Patients with confounding immunologic co-morbid conditions were excluded. Recorded demographic data collected for this example embodiment, for example, include age, gender, date, body mass index, nicotine use, injury severity score (ISS), Acute Physiology and Chronic Health Evaluation II (APACHE-II) scores, concomitant traumatic brain injury, location and mechanism of injury, wound size, associated major vascular injury to the effected limb, and type of wound closure.

All wounds were examined once daily and patients were followed for 30 days. The primary clinical outcome measure was successful wound healing after definitive closure or coverage with skin graft. Impaired wound healing included delayed wound closure or wound dehiscence after closure or coverage. Delayed wound closure was defined as definitive closure occurring 21 days or more after the injury, or two standard deviations outside of the mean normal wound closure time period of 10 days. Dehiscence was defined as spontaneous partial or complete wound disruption after primary closure or greater than 50% skin graft loss. Wounds that progressed to healing at 30 days without necessitating a return to the operating room were considered healed. Surgical debridement, pulse lavage, and VAC application were repeated every 48-72 hours until wound closure or coverage, according to current institutional standards of practice. Timing of closure was at the discretion of the attending surgeon.

Peripheral venous blood (8 mL) was drawn prior to each surgical debridement from the patient. Wound effluent samples (30 mL or more) were collected from the VAC canister (without gel pack; Kinetic Concepts, Inc., San Antonio, Tex.) 2 hours following the first surgical debridement and over a 12 hour period prior to each subsequent wound debridement. All serum samples were immediately separated using a centrifuge at 2500 g for ten minutes. Serum supernatants and effluent samples were transferred to individually labeled polypropylene tubes (e.g., Cryo-Loc™; Lake Charles Manufacturing, Lake Charles, La.), flash-frozen in liquid nitrogen, and stored at −80° C. until analysis. A 1 cm3 wound tissue specimen was obtained from the center of the wound bed at each debridement and immediately stored (e.g., in RNAlater; Ambion, Austin, Tex.) at 4° C.

In at least one embodiment of the invention, serum and wound effluent proteins of interest were quantified using a Luminex® 100 IS xMAP Bead Array Platform (Millipore Corp, Billerica, Mass.). Serum and wound effluent samples were diluted 2-fold and 100-fold, respectively, and incubated with analyte-specific monoclonal antibodies covalently linked to uniquely fluorescent beads. Subsequently, biotinylated monoclonal antibodies specific for the bead-linked-antibody: analyte complexes were introduced. This secondary complex was then detected by streptavidin-phycoerythrin. An embodiment of the invention performs this procedure using the commercially available Beadlyte® Human 22-Plex Multi-Cytokine Detection System (Millipore, Billerica, Mass.) according to manufacturer's instructions and using the sample dilutions specified above.

Twenty-two cytokines and chemokines (IL-1α, IL-1β, IL-2, IL-3, IL-4, IL-5, IL-6, IL-7, IL-8, IL-10, IL-12(p40), IL-12(p70), IL-13, IL-15, IP-10, Eotaxin, IFN-γ, GM-CSF, MCP-1, MIP-1α, RANTES, and TNFα) were quantified using a detection system (e.g., Beadlyte® Human 22-Plex Multi-Cytokine Detection System; Cat. #48-011; Upstate/ Millipore, Billerica, Mass.). RNA transcripts and translated proteins of IL-1α, IL-1β, IL-2, IL-3, IL-4, IL-5, IL-6, IL-7, IL-8, IL-10, IL-12(p40), IL-12(p70), IL-13, IL-15, IP-10 (CXCL10), Eotaxin (CXCL11), IFN-γ, GM-CSF (CSF2), MCP-1 (CCL2), MIP-1α(CCL3), RANTES (CCL5), and TNFα in patients with traumatic wounds were examined as potential biomarkers of wound healing and indicators of proper time of wound closure or coverage. As illustrated in FIG. 14, the expressions of a total 190 genes are studied. Gene names are provided in FIG. 15A-15J.

RNA was extracted from a biopsy sample of the wound bed and converted to cDNA by standard extraction and reverse transcription techniques with adherence to common quality assurances. Quantitative polymerase chain reaction (qPCR) was performed to calculate the relative expressions of the array of gene targets (see FIG. 14). An embodiment of the invention used a real-time thermocycler, 7900HT Fast Real-Time PCR System (Applied Biosystems, Foster City, Calif.) and a custom designed panel of 190 primer:probe sets for target genes arranged in duplicate in a custom format of a TaqMan Low Density Array (Applied Biosystems, Foster City, Calif.) to assess gene transcript expression. An 18S rRNA-specific primers:probe set was included in quadruplet on this array to serve primarily as an internal calibrator.

Associations between categorical variables were studied with Fisher exact test or χ2test, as appropriate. Continuous variables were assessed with the Mann-Whitney U-test and Kruskal-Wallis test for multiple comparisons. Wounds were considered independently for statistical analysis of analyte expression and healing outcome. An embodiment of the invention performs statistical analysis using SPSS (Version 16.0, SPSS Inc., Chicago, Ill.). A two-tailed p value of less than 0.05 was considered statistically significant. Both systemic and wound-specific extents of injury are clinical determinants of the subsequent wound healing outcome. As illustrated in FIG. 16, significant risk factors for impaired wound healing include elevated Injury Severity Score (ISS) (p=0.001), larger wound size (p=0.03), and associated vascular injury (p=0.016). Age, body mass index, tobacco use, mechanism of injury, wound location, traumatic amputation, and closure method are not associated with wound healing (p>0.05).

As illustrated in FIG. 17, in addition to increased ISS, patients with impaired wound healing also demonstrated sustained physiologic derangement with elevated APACHE II scores at each surgical debridement. Mean APACHE II scores are statistically higher over the first three debridements (p<0.05) and remain elevated at wound closure in patients with impaired wound healing. Thus, the severity of systemic illness following traumatic injury is associated with decreased capacity for wound healing.

Serum cytokine and chemokine expression is associated with impaired wound healing. As illustrated in FIG. 18, the physiologic response to acute traumatic injury is reflected in the serum cytokine and chemokine data. The pro-inflammatory cytokine IL-6 is statistically higher at each surgical debridement in patients with impaired healing compared to patients with normal healing (p<0.05). The anti-inflammatory cytokine IL-10 is statistically higher from the second debridement until wound closure in this comparison (p<0.05). The chemokine MCP-1 is consistently higher while IP-10 is higher at the second debridement (p<0.05). The cytokines IL-5 and IL-7 are significantly increased at the second debridement in the impaired healing patients (p<0.05) (data not shown). All other analytes do not differ between the groups. Thus, a dysregulated inflammatory systemic response is observed in patients with impaired wound healing.

Wound VAC effluent cytokine and chemokine expression is associated with impaired wound healing. As illustrated in FIG. 19, patients with impaired wound healing express statistically higher initial wound effluent IL-6, IL-10, MCP-1, and MIP-1α compared to patients with normal healing (p<0.05). Moreover, patients with impaired wound healing express statistically lower IL-5 at the third and final debridements (p<0.05). Thus, similar to the systemic condition, a wound-specific dysregulated inflammatory response is observed in wounds with impaired wound healing.

Tissue biopsies from healed and dehisced wounds are analyzed over all debridements. Wounds with impaired healing express higher inflammatory cytokines and chemokines compared to healed wounds. As illustrated in FIGS. 20A-B, these findings suggest that acute wound failure represents unresolved inflammation at the molecular level and subsequent failure to progress through the normal phases of wound healing. Receiver operating characteristics for individual serum and effluent biomarkers are analyzed over all wound debridements. Serum IL-6, IL-8, IL-10, MCP-1 and IP-10, and effluent RANTES are statistically predictive of wound healing outcome (p<0.05). Specifically, serum IL-10 has an AUC of 0.902 and a p value of less than 0.001; and, serum MCP-1 has an AUC of 0.889 and a p value of less than 0.001. Serum IL-6 has an AUC of 0.886 and a p value of less than 0.001; and, serum IP-10 has an AUC of 0.865 and a p value of less than 0.001. Serum IL-8 has an AUC of 0.815 and a p value of 0.003; and, effluent RANTES has an AUC of 0.790 and a p value of 0.006.

An embodiment of the invention provides a BBN-ML for estimating wound healing outcomes using cytokine and chemokine biomarker expression levels. As described above, inflammatory wound effluent cytokine and chemokine expression at time of initial wound debridement is correlated with wound outcome. Patients with subsequent wound dehiscence express significantly higher initial effluent inflammatory cytokines and chemokines (IL-1β, IL-6, IL-8, IL-10, and MCP-1) compared to patients with normal healing. Corroboratively, wound biopsy gene expression of inflammatory cytokines and chemokines is elevated in dehisced wounds relative to healed wounds. Furthermore, serum IL-6 and IL-10, and effluent IL-5 and RANTES are individually predictive of wound healing outcome as indicated by their receiver-operating characteristics.

However, in a complex physiologic system, it is unusual that an individual biomarker is robustly predictive of any outcome. In addition, based on the initial observations, cytokine and chemokine profiles that favor wound healing dynamically change throughout the healing (marked by debridements) process (see FIG. 18). To describe these complex, non-obvious relationships over time, the BBN-ML is used to relate serum and effluent cytokine and chemokine concentrations to expected wound healing outcome at each surgical debridement.

Multivariate conditional dependence relationships are identified using Bayesian modeling software (e.g., FasterAnalytics™). Bayesian probability theory relates the conditional probabilities of two or more random events in order to compute posterior probabilities and has been used previously in clinical diagnostics [38, 48-49]. A probabilistic model is generated using the serum and wound effluent cytokine and chemokine protein data at each surgical debridement from healed patient population. A step-wise training process is used to prune included features of the Bayesian network to improve model robustness and elucidate the cytokines/chemokines with the most significant influences on wound outcome. Serum MCP-1, IP-10, and IL-6 and effluent MCP-1, IL-5, and RANTES are highly predictive of outcome. As illustrated in FIG. 18, impaired healing is associated with high serum MCP-1, IP-10, IL-6 and effluent MCP-1 and low effluent IL-5 and RANTES at various wound debridements. As early as the first debridement, wound healing outcome is determined based on serum and effluent MCP-1, serum IL-6 and effluent IL-5 expression (FIG. 18).

FIG. 21A illustrates a BBN-ML 2100 for predicting wound healing 2110 (either impaired or normal), according to an embodiment of the invention. Each node in the BBN-ML 2100 represents a biomarker level 2120A-2120L: IL-6 from serum at day 3; MCP-1 from serum at day 1; IL-6 from serum at day 1; RANTES from wound effluent at day 3; IP-10 from serum at day 3; IP-10 from serum at day 2; MCP-1 from wound effluent at day 1; IL-5 from wound effluent at day 3; MCP-1 from serum at day 2; MCP-1 from serum at day 30; IP-10 from serum at day 1; and, IL-5 from wound effluent at day 30, respectively. Specifically, each node represents the serum or wound effluent concentration (quantitated as mean fluorescence intensity) of the individual cytokine or chemokine biomarker 2120A-2120L at specific time points along the healing trajectory. FIG. 21B illustrates the receiver-operating characteristics for the cross validation of the BBN-ML 2100. The receiver-operating characteristics show that the BBN-ML 2100 is very robust with an AUC of 0.872.

Figure 21C:
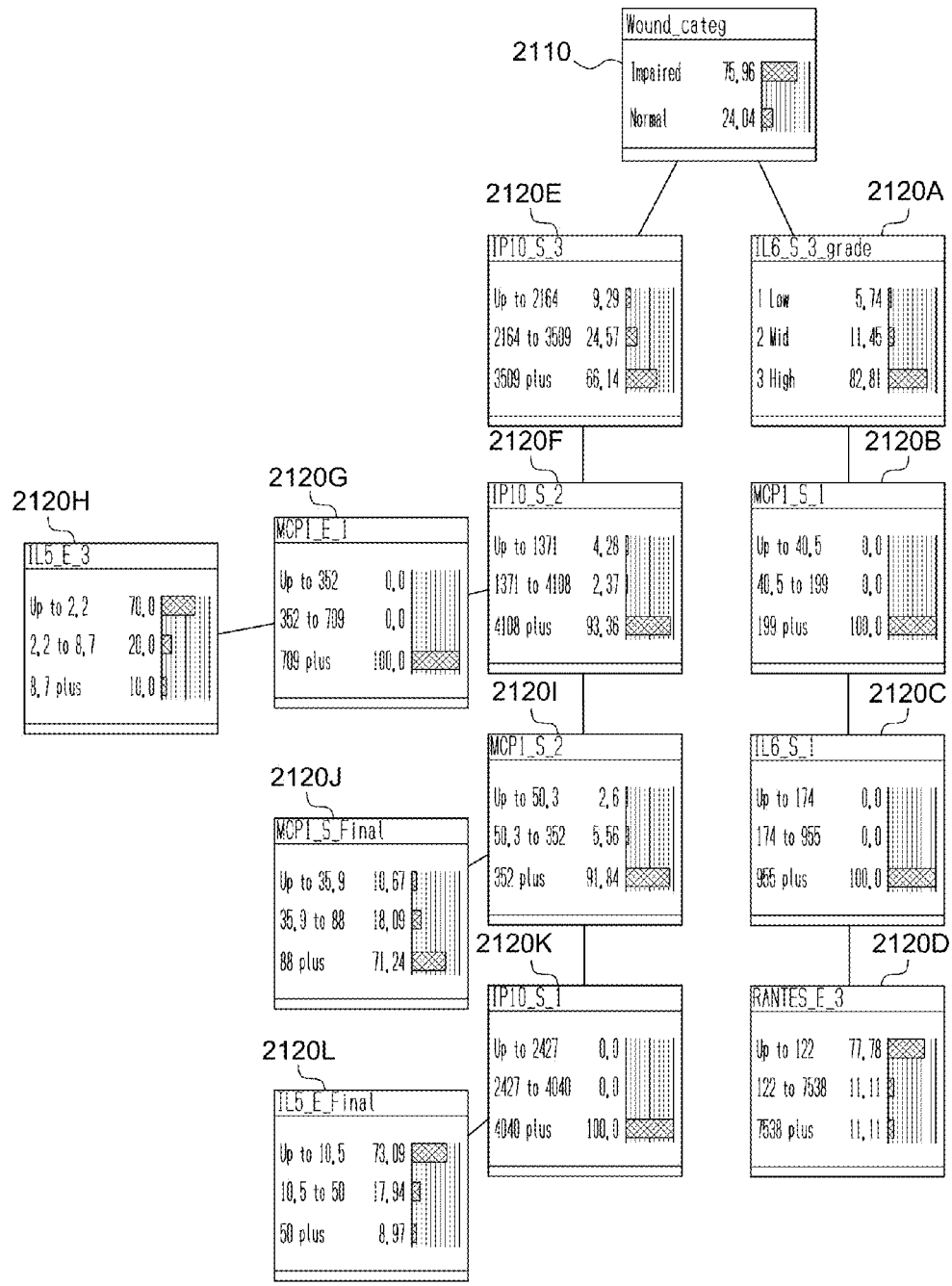
Figure 21D:
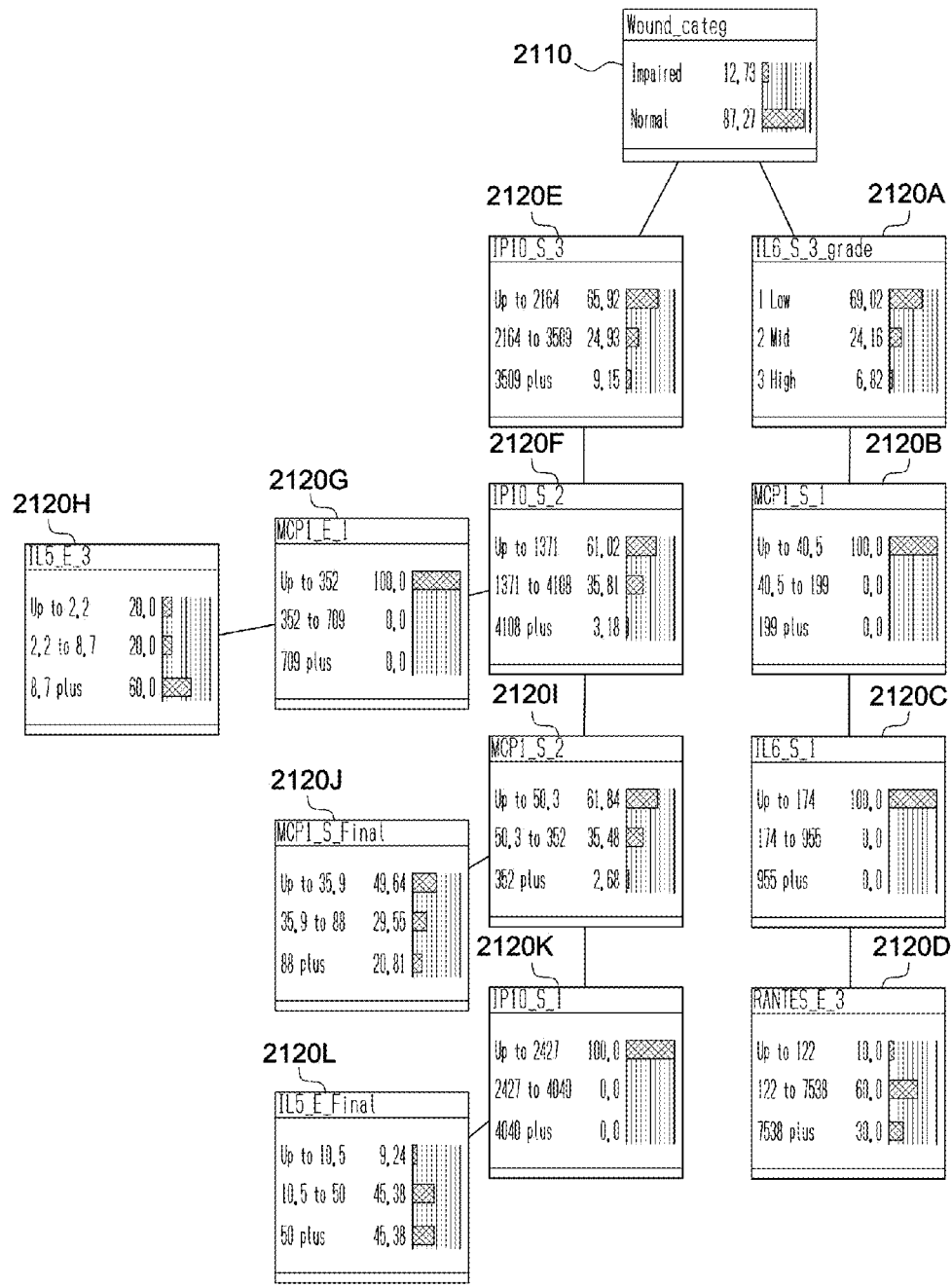

As described above, the predictive models of the embodiments herein are in an interactive format when used in conjunction with a GUI, such that clinicians can enter known values for a current patient (e.g., by clicking on the cross-hatched bars in the model nodes) and receive a estimate of the probability of healing impairment. Thus, as illustrated in FIG. 21C, if on day 1, MCP1 in the wound effluent and MCP-1, IL-6, and IP-10 in the serum are high (nodes 2100B, 2100C, 2100G, and 2100K), then there is a 76% likelihood of wound healing impairment. However, if these same proteins are low, as illustrated in FIG. 21D, then there is an 87% probability of normal wound healing.

In at least one embodiment, a K-fold cross-validation is used to test the BBN-ML. Cross-validation by number of patients (19) is performed to avoid modeling bias by omitting all serum data from the training set that would appear in the testing set. A ROC curve of these predictions is calculated to determine model robustness for predicting wound healing outcome. In a K-fold cross-validation, the original sample is partitioned into K subsamples. Of the K subsamples, a single subsample is retained as the validation data for testing the predictive models, and the remaining K−1 subsamples are used as training data. The cross-validation process is repeated K times (the folds), with each of the K subsamples used exactly once as the validation data. The K results from the folds are averaged (or otherwise combined) to produce a single estimation. Contrary to repeated random sub-sampling, all observations are used for both training and validation, and each observation is used for validation exactly once.

Figure 21E:
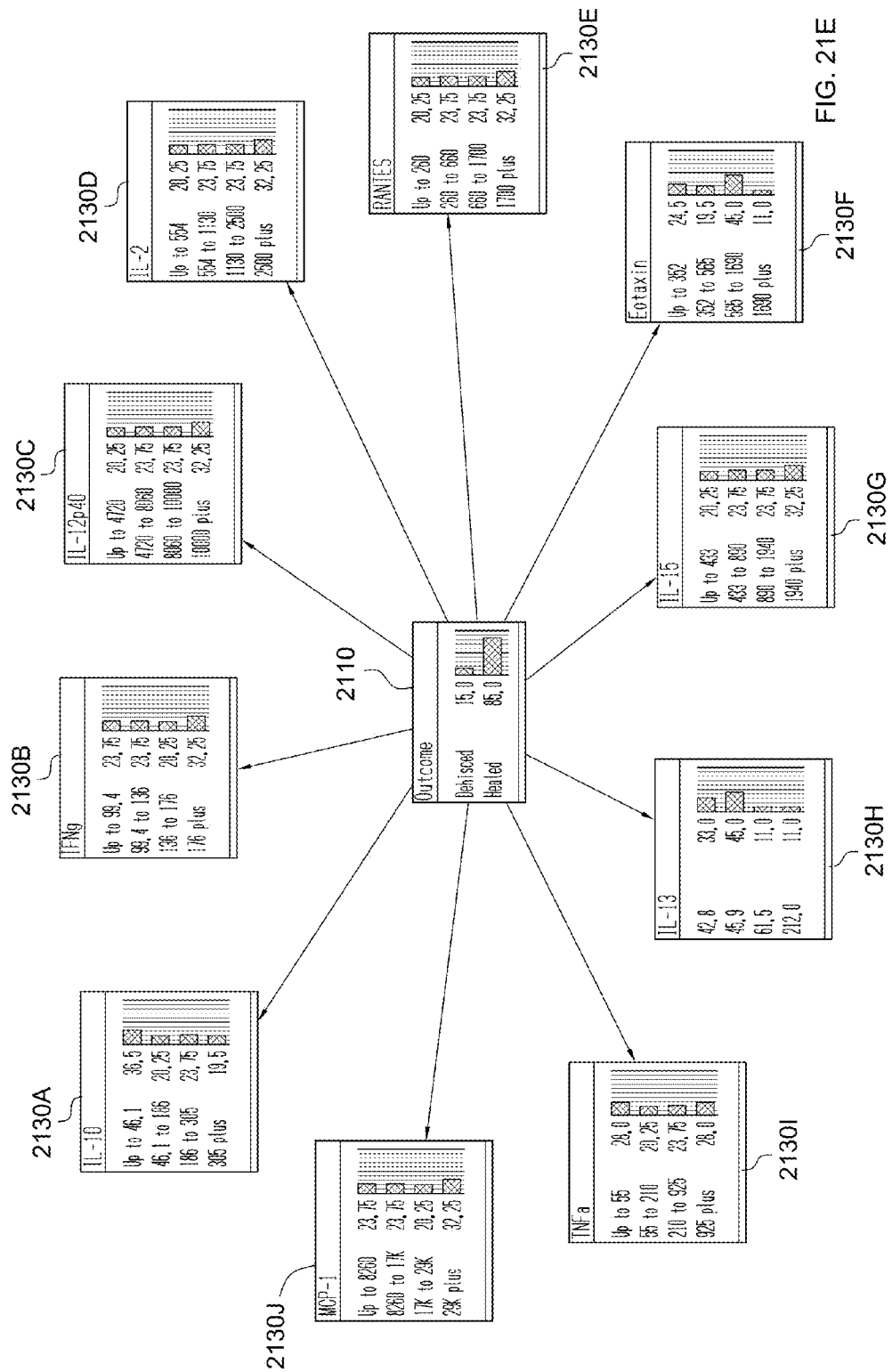
Figure 21F:
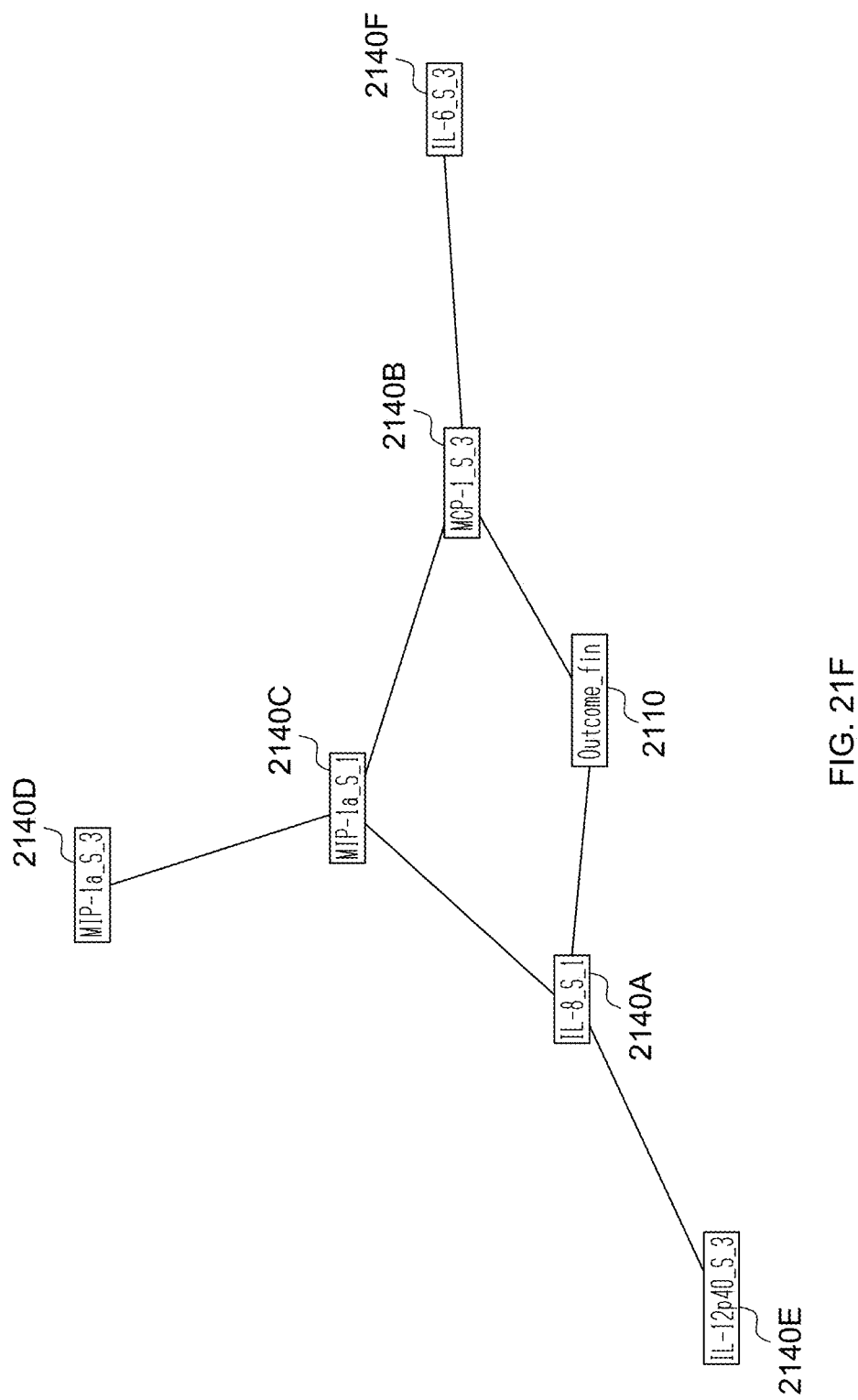
Figure 21G:
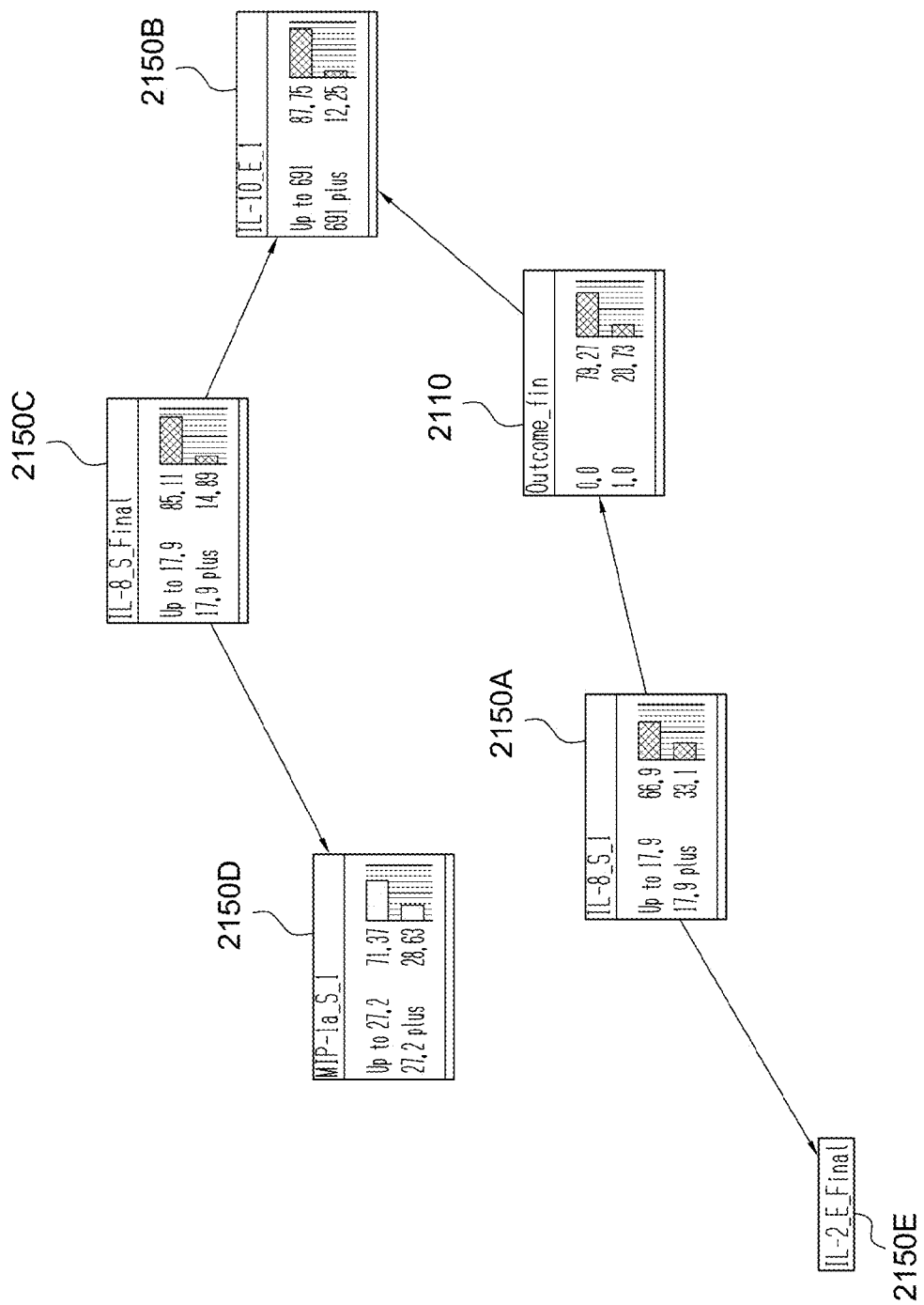

FIG. 21E illustrates a naive BBN for predicting the probability of wound healing (dehisced or healed) according to an embodiment of the invention, wherein relative contribution of the predictors 2130A-2130J include 4 bins (i.e., levels of gene expression). Specifically, wound healing outcome 2110 is dependent upon the gene expression levels of biomarkers IL-10, IFNg, IL-12p40, IL-2, RANTES, Eotaxin, IL-15, IL-13, TNFα, and MCP-1. FIG. 21F illustrates an interim BBN for predicting the probability of wound healing according to an embodiment of the invention. Specifically, wound healing outcome 2110 ("Outcome_fin") is dependent upon the gene expression levels of biomarkers IL-8_S__1, MCP-1_S__3, MIP-1a_S__1, MIP-1a_S__3, IL-12p40_S__3, and IL-6_S__3 (predictors 2140A-2140F, respectively). The final BBN-ML is illustrated in FIG. 21G according to an embodiment of the invention, wherein each of the predictors 2150A-2150E includes two gene expression level bins. The predictors 2150A and 2150C each have a lower bin of less than or equal to 17.9 and an upper bin of greater than 17.9. The predictor 2150B has a lower bin of less than or equal to 691 and an upper bin of greater than 691; and, the predictor 2150D has a lower bin of less than or equal to 27.2 and an upper bin of greater than 27.2.

As illustrated in FIG. 21B, the cross-validation of the BBN-ML showed that the model was robust and effectively estimated wound healing outcome (AUC=0.872, p=0.002). The Bayesian Belief Network (i.e., the BBN-ML) has a sensitivity of 88.9%, a specificity of 90%, an impaired predictive value of 80%, and a normal predictive value of 94.7%. An embodiment of the invention prospectively validates the BBN-ML using de novo biomarker data of patients with unknown wound healing outcome. Eighty (80) patients were recruited from adult male and females with extremity wounds (including the shoulder and buttock), which may be treated by VAC. The patients had an Injury Severity Score of 9, a minimum wound size greater or equal to 75 cm2, and were at least 18 years old. To reduce the risk of clinical trails, patients with Coronary Artery Disease, Diabetes Mellitus (IDDM or T2DM), Peripheral Vascular Disease, connective tissue disorders, immunosuppression, pregnancy, or age greater than 65 years old were excluded from the study.

The patients were separated into two arms. For the control arm (n=40), samples were collected but surgical wound closure was based on the attending surgeon's discretion. For the experimental Arm (n=40), samples were collected, analyzed with the BBN-ML, and surgical wound closure was based upon the BBN-ML's prediction. Wounds with greater than 70% probability to heal were closed. Wound biopsies, effluent and serum collections were obtained at each wound exploration and washout, which were expected to occur within 24 hours of each patient's admission and every 48-72 hours subsequently. Wound biopsies were processed for quantitative real-time PCR using a low-density array; and, effluent/serum proteins were quantitated using a multiplex antibody-based assay. Biomarker expression levels were used as evidence in the BBN-ML of wound healing to obtain the predicted wound outcome if the wound was to be surgically closed during the following operating room visit.

Data analysis was performed using traditional (Frequentist) statistics and Bayesian statistics. Under traditional statistical analysis, associations between categorical variables were evaluated with Fisher exact test or $\chi 2$ test, as appropriate. Continuous variables were assessed with the Mann-Whitney U-test and Kruskal-Wallis test for multiple comparisons. Wounds were considered independently for statistical analysis of analytes (cytokines/chemokines) expression and healing outcome. ROC curves were constructed by plotting sensitivity versus 1—specificity, and the AUC was calculated to ascertain the predictive value of the cytokine and chemokine biomarker profiles. An embodiment of the invention performs statistical analysis using SPSS (Version 16, SPSS Inc., Chicago, Ill.). A two-tailed p value<0.05 is considered statistically significant.

For the training of the BBN-ML model, the data generated from the clinical studies along with clinical parameters were collected in a common database. This data was reviewed for accuracy and usability. The data was analyzed using the BBN-ML to identify conditional dependence between clinical outcomes and specific surrogate biomarker profiles to establish a model of biomarker/outcomes dependency and quantitative, patient-specific risk stratification.

The BBN-ML allows surgeons to use a quantitative, reliable method for wound assessment rather than subjective methods in current practice, which can reduce surgeon-to-surgeon variability involved in determining the proper time for definitive wound closure. Using the patient's biomarker values, the BBN-ML provides the surgical team with an estimate of wound-healing rate and the likelihood of healing success if the wound were to be closed. Providing such a quantitative and objective measure of wound status greatly reduces intra-observer variability and improves personalized, and in some cases wound-specific, treatment of trauma patients. The BBN-ML has machine-learning capabilities in that the accuracy of the BBN-ML improves with each additional patient's biomarker information entered into the database. Thus, data from the clinical study is collected for model refinement.

For the training of the BBN-ML model, the data generated from the clinical studies along with clinical parameters were collected in a common database. This data was reviewed for accuracy and usability. The data was analyzed using the BBN-ML to identify conditional dependence between clinical outcomes and specific surrogate biomarker profiles to establish a model of biomarker/outcomes dependency and quantitative, patient-specific risk stratification.

The BBN-ML allows surgeons to use a quantitative, reliable method for wound assessment rather than subjective methods in current practice; this should reduce surgeon-to-surgeon variability involved in determining the proper time for definitive wound closure. Using the patient's biomarker values, the BBN-ML provides the surgical team with an estimate of wound-healing rate and the likelihood of healing success if the wound were to be closed. Providing such a quantitative and objective measure of wound status greatly reduces intra-observer variability and improves personalized, and in some cases wound-specific, treatment of trauma patients. The BBN-ML has machine-learning capabilities in that the accuracy of the BBN-ML improves with each additional patient's biomarker information entered into the database. Thus, data from the clinical study is collected for model refinement.

The BBN-MLs support several scoring metrics for network optimization: Minimum Description Length (MDL), also known as the Bayesian Information Criterion (BIC), as well as Bayesian Scoring (BDe). Minimum Description Length scoring provides a measure of quality of a model. It trades off between goodness-of-fit and model complexity. Goodness-of-fit is measured as the likelihood of the data given the model. Model complexity equals the amount of information required to store the model, subject to an inflator/deflator set by the user. Bayesian Scoring is asymptotically equivalent to MDL scoring. MDL scoring ensures that the final model represents the most likely model given the data used for learning and the model variations under consideration.

D. Breast Cancer Risk

Another embodiment of the invention inputs data into a BBN-ML to predict breast cancer risk. 591 female military healthcare beneficiaries were enrolled into an IRB-approved, single-arm, prospective pilot screening trial between August 2002 and March 2005. The clinical protocol was reviewed and approved by the Institutional Review Boards of Walter Reed Army Medical Center (WRAMC), Washington, D.C. and Keller Army Hospital (KAH), West Point, N.Y. Subjects were recruited from the gynecology clinic or Comprehensive Breast Center at WRAMC or the gynecology or family practice clinic at KAH. Study inclusion criteria consisted of younger women age 18 to 49 years. Age was stratified for analysis as follows (<30, 30-34, 35-39 and 40-49). Potential study subjects were excluded if: they had breast surgery (including core biopsy) or were lactating within the preceding 3 months, had breast fine needle aspiration within the preceding one-month, were pregnant, had electrically powered implanted devices (e.g. pacemaker) or were undergoing chemotherapy or radiation treatment. Data collected for each study subject included age, race/ethnicity, clinical history (personal and family history of breast cancer, previous breast surgery or biopsy and results of those interventions), hormonal information (age of menarche and first full-term pregnancy, menstrual status, date of last menstrual period and exogenous hormone use), breast density and size (bra cup size), Gail Model risk estimate, results of clinical breast exam (CBE), screening breast electrical impedance scanning (EIS), conventional imaging and biopsy results. The study participants underwent EIS of the breast (e.g., using the T-Scan™ 2000ED (Mirabel Medical, Austin, Tex.)) [69].

In at least one embodiment of the invention, the BBN-ML is trained using a priori variables to estimate the likely diagnostic outcome of breast biopsy. The BBN-ML is developed using machine learning algorithms (e.g., FasterAnalytics™), which automatically learn network structure and joint probabilities from the prior probabilities in the data. BBN models are a type of directed acyclic graph, which means that they represent information in a hierarchical format, which identifies variables which contain the most information and are thus most useful for estimating outcomes. The associations represented by the BBN-ML are associations of conditional dependence.

An embodiment of the invention performs cross-validation on the BBN-ML using a train-and-test cross-validation methodology to produce classification accuracy estimates. Five-fold cross validation is performed by randomizing the data set into 5 separate and unique train-and-test sets. Each set consists of a training set comprised of 80% of patient records and a test set consisting of the remaining 20% of records. Once the BBN-ML is constructed with a training set, the matching test set is entered into the BBN-ML, generating a case-specific prediction for each record for independent variables of interest. A ROC curve is plotted for each test to calculate classification accuracy. The ROC curve is used to calculate the AUC and corresponding predictive values for biopsy outcome.

In at least one embodiment, the study population was comprised of an ethnically diverse group of younger women (41% non-Caucasian). FIG. 22 is a table illustrating characteristics of the study population by age; and, FIG. 23 is a table illustrating characteristics of the study population by biopsy. Of the 591 study participants, 67% were under the age of 40 (mean age: 35±6.9 years), and 90% pre-menopausal. Two percent of the study population was taking exogenous hormones at the time of study enrollment; however, there was no statistically significant association with disease ($x^2=0.95$). Fifty-five percent of participants had no family history of breast cancer, and family history was only marginally associated with biopsy outcome ($x^2=0.10$). The findings of CBE were statistically associated with both age ($x^2=0.01$) and disease ($x^2<0.001$); 31% of subjects had findings that were deemed not suspicious, while 4% of subjects had suspicious CBE findings. Five percent of study subjects had estimated 5-year risk of breast cancer≧1.66% according to the Gail Model and these findings were statistically associated with both disease and age of subject ($x^2<0.001$). Mammography was performed in 281 women and found to be BIRADS III or higher in 75 cases (27%), while mammography was found to be statistically associated with both disease and age of subject ($x^2<0.001$). Breast ultrasound examination was performed in 258 women and found to be BIRADS III or higher in 66 cases (26%); ultrasound was statistically associated with disease ($x^2<0.001$), but not with age ($x^2=0.18$). Three risk factors were not statistically associated with biopsy outcome: mean age at menarche ($p=0.12$), mean age at first pregnancy ($p=0.39$), and nulliparity ($x^2=0.93$). There was no statistically significant difference between the mean age of the study population (35 years) and the mean age at time of cancer diagnosis (38 years, $x^2=0.35$), or diagnosis of pre-malignant histopathology (38 years, $x^2=0.56$). Data is tabulated by age group and biopsy outcome as shown in FIGS. 22-23.

Of the 591 women enrolled in the study, 568 screened EIS negative (low risk) and 23 EIS positive (high risk). In the EIS negative group, 95 underwent biopsy and 87 were benign on final histopathology. The eight remaining women were either pre-malignant (n=4) or malignant (n=4). In the EIS positive group, 10 underwent biopsy and five were benign, while five were either pre-malignant (n=3) or malignant (n=2). Of 13 pre-malignant or malignant lesions, EIS identified five (38.5%). The NPV of the EIS negative group was 92%, while the PPV of the EIS positive group was 50%.

FIG. 24 illustrates a BBN-ML for predicting breast cancer risk according to an embodiment of the invention. The six nearest independent associated features (direct relationship to breast biopsy diagnosis), in the illustrated BBN-ML used to estimate a breast biopsy diagnosis (Biopsy Category 2400) are: screening breast EIS result 2410A, Gail model cutoff 2410B (5-year risk estimate<1.66% vs. ≧1.66%), MMG BIRAD result 2410C (mammogram) and MRI BIRAD result 2410D, breast size 2410E, and personal history of breast disease 2410F. This does not mean, however, that 'Any Palpable Mass' on clinical breast examination 2410G and ultrasound (US) BIRAD result 2410H (indirect relationship to breast biopsy diagnosis 2400) do not influence the estimate of likely biopsy diagnosis, but rather that they are conditionally independent of biopsy outcome given knowledge of screening breast EIS 2410A and MMG BIRAD result 2410C.

The illustrated BBN-ML was validated using train-and-test cross-validation, and produced strongly predictive AUCs (0.75-0.97) for differentiating malignancy and premalignant disease from benign findings (FIG. 25). Specifically, the BBN-ML has ROC curves, when cross validated, with AUCs of 0.88, 0.97 and 0.75 for benign, malignant, and premalignant findings, respectively. Cross-validation also produces a 97% NPV and a 42% PPV for malignancy. With a relatively small set of outcomes, there is a high degree of variance in results between cross-validation exercises (FIG. 25). The BBN-ML is a recursive information structure, and the inclusion of conditional dependence between predictive variables guards against over-interpretation of data (over-fitting). The BBN-ML informs estimates not only through estimation of biopsy outcome, but simultaneously through estimation of as-yet unknown imaging results, wherein estimates of biopsy outcome are derived from available clinical and imaging data, even if some imaging studies are unavailable at time of biopsy outcome estimation.

FIGS. 26A-C illustrate a BBN-ML for predicting breast cancer risk according to an embodiment of the invention, including clinical parameters 2410A-2410H. Knowledge of breast size 2410E (bra cup B) results in slightly lower risk of cancerous biopsy result (−3.6%) for the test subject compared to the study population (FIG. 26A). When the additional knowledge of Gail model cutoff 2410B is added (FIG. 26B) to refine the posterior estimate of biopsy outcome 2400 given previously known breast size 2410E, there is a 12% increased likelihood of cancerous biopsy, and a 17% increase in the likelihood of pre-malignant histology, relative to the overall study cohort. Moreover, adding a positive (high risk) EIS screening result 2410A (FIG. 26C) increases the posterior risk estimate of cancerous biopsy by 21%, and the risk estimate of pre-malignant disease by 35%.

As clinical parameters 2410A-2410H are, at some level, conditionally dependent with biopsy outcome 2400, the clinical parameters 2410A-2410H that are available at the time of initial clinical visit (a priori knowledge) are selected and applied to the BBN-ML to estimate biopsy outcome. Subsets of the clinical parameters 2410A-2410H are also used to generate an inference table (FIG. 27) that can be used by clinicians to quickly estimate biopsy outcome for all known combinations of the identified clinical parameters 2410A-2410H if the GUI interface to the BBN-ML is unavailable. The incremental value of both screening breast EIS 2410A and Gail model cutoff 2410B is shown in the FIG. 27. Under the most favorable circumstances (EIS negative and Gail model 5-year risk<1.66%), the risk of malignancy is 2.6%.

Under the least favorable circumstances (screening EIS positive and Gail model 5-year risk≧1.66%), the risk of malignancy is 45%.

In at least one embodiment of the invention, screening breast EIS result 2410A, Gail model cutoff 2410B, MMG BIRAD result 2410C and MRI BIRAD result 2410D, breast size 2410E, and personal history of breast disease 2410F are each related to biopsy category 2400 when examined using the calculated chi square. CBE 2410G and breast ultrasound results 2410H are also statistically associated with biopsy outcome, and the BBN-ML includes these features as well, but they are associated with biopsy outcome through EIS and mammography results. Other features that have bivariate statistical significance, but are not included in the BBN-ML illustrated in FIGS. 26A-C, include patient ethnicity, menopausal status, and prior breast biopsy. The machine learning process produces a parsimonious BBN-ML; thus, in at least one embodiment, these additional factors are not included in favor of more specific imaging and personal history risk factors. However, as the training population database is enhanced and enlarged, the BBN-ML will be retrained and the structure and priority of the features in the BBN-ML may be revised to more robustly reflect the clinical population.

In an embodiment of the invention, a number of attributes having statistically significant association with patient age, including CBE findings, mammography BIRADS category, nulliparity, and Gail Model 5-year risk score. Conversely, certain factors that are significantly associated with biopsy outcome using both bivariate statistical tests and the machine-learning process, are not associated with patient age: breast (bra cup) size, EIS screening exam, or MRI. There is no statistically significant difference in mean age at diagnosis of pre-malignant or malignant disease compared to the mean age of the study population. When biopsy results are examined by age category, the results do not demonstrate any statistically significant associations. Additionally, features generally considered as well established breast cancer risk factors in the general population are not statistically significant with biopsy outcome in the younger test population, including family history of breast cancer, age at menarche, nulliparity, and age at first pregnancy.

In at least one embodiment, the BBN-ML not only allows the posterior estimation of the likely biopsy outcome, but also identifies a hierarchy of conditional dependence, which identifies which pieces of information are most useful in calculating the estimate. This hierarchy also defines how independent variables influencing biopsy outcome also influence one another, providing a better understanding of how the estimate is derived and providing an opportunity to estimate missing parameters using those currently available for any given patient. Because this hierarchy is trained using fully unsupervised machine learning, the hierarchy will change over time as knowledge is accrued. The combined effect of these independent predictors on likelihood of disease is greater than the sum of the individual effects. By way of example, in one embodiment, mammography finding of BIRAD IV increases the likelihood of a malignant biopsy result in the study population by five percent, while a Gail 5-year risk score>1.66% increases the likelihood of malignancy by 26%, yet together these findings increase the likelihood of disease by 42%—greater than the sum total of their individual effects.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment or an embodiment containing both hardware and software elements. In at least one exemplary embodiment, the invention is implemented in a processor (or other computing device) loaded with software, which includes but is not limited to firmware, resident software, microcode, etc.

A representative hardware environment for practicing at least one embodiment of the invention is depicted in FIG. 28. This schematic drawing illustrates a hardware configuration of an information handling/computer system in accordance with at least one embodiment of the invention. The system includes at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

Computer program code for carrying out operations of the present invention may be written in a variety of computer programming languages. The program code may be executed entirely on at least one computing device (or processor), as a stand-alone software package, or it may be executed partly on one computing device and partly on a remote computer. In the latter scenario, the remote computer may be connected directly to the one computing device via a LAN or a WAN (for example, Intranet), or the connection may be made indirectly through an external computer (for example, through the Internet, a secure network, a sneaker net, or some combination of these).

It will be understood that each block of the flowchart illustrations and block diagrams and combinations of those blocks can be implemented by computer program instructions and/or means. These computer program instructions may be provided to a processor of a general purpose computer, special purpose computer, application specific integrated circuit (ASIC), or other programmable data processing apparatus to produce a machine, such that the instructions, which execute via the processor of the computer or other programmable data processing apparatus, create means for implementing the functions specified in the flowcharts or block diagrams.

REFERENCES

[1] Welker M J, Orlov D., Thyroid nodules, Am Fam Physician 2003; 67:559-66, 573-4. [2] Mazzaferri E L, Thyroid cancer in thyroid nodules: finding a needle in the haystack, Am J Med 1992; 93:359-62. [3] Baloch Z W, Cibas E S, Clark D P, Layfield L J, Ljung B M, Pitman M B, Abati A., The National Cancer Institute Thyroid fine needle aspiration state of the science conference: a summation, Cytojournal 2008 Apr. 7; 5:6. [4] Are C, Hsu J F, Schoder H, Shah J P, Larson S M, Shaha A R: FDG-PET detected thyroid incidentalomas: Need for further investigation? Ann Surg Oncol 2007, 14:239-247. [5] Sathekge M M, Mageza R B, Muthuphei M N, Modiba C M, Clauss R C: Evaluation of thyroid nodules with technetium-909m MIBI and technetium-99m pertechnetate, Head Neck 2001, 23:305-310. [6] Baloch Z W, LiVolsi V A, Fine-needle aspiration of thyroid nodules: past, present, and future, Endocr Pract, 2004 May-June; 10(3):234-41. [7] Deveci M S, Deveci G, LiVolsi V A, Baloch Z W, Fine-needle aspiration of follicular lesions of the thyroid. Diagnosis and follow-Up, Cytojournal, 2006 Apr. 7; 3:9. [8] Nissan A, Peoples G E, Abu-Wasel B, Adair C F, Prus D, Howard R S, Lenington S G, Fields S I, Freund H R, Peretz T, Burch H B, Shriver C D, Stojadinovic A., Prospective trial evaluating electrical impedance scanning of thyroid nodules before thyroidectomy: Final results, Ann Surg. 2008 May; 247(5):843-53. [9] Stojadinovic A, Fields S I, Shriver C D, et al., Electrical Impedance Scanning of Thyroid Nodules Prior to Thyroid Surgery: A Prospective Study, Annals of Surgical Oncology 2005; 12(2): 152-160. [10] Raza S N, Shah M D, Palme C E, et al., Risk factors for well-differentiated thyroid carcinoma in patients with thyroid nodular disease, Otolaryngol Head Neck Surg. 2008 July; 139(1):21-6. [11] Varverakis E, Neonakis E, Tzardi M, Chrysos E., Role of color Doppler ultrasonography in the preoperative management of cold thyroid nodules, Hormones 2007; 6(1):44-51. [12] Lyshchik A, Moses R, Barnes S L, et al., Quantitative analysis of tumor vascularity in benign and malignant solid thyroid nodules, J Ultrasound Med. 2007 June; 26(6):837-46. [13] Varverakis E, Neonakis E., Contribution of high-resolution ultrasonography in the differential diagnosis of benign from malignant thyroid nodules, Hormones (Athens) 2002; 1: 51-56. [14] Spiezia S, Cerbone G, Colao A, et al., Usefulness of power Doppler in the diagnostic management of hypoechoic thyroid nodules, Eur J Ultrasound 1997; 6: 165-170. [15] Rago T, Vitti P, Chiovato L et al., Role of conventional ultrasonography and color flowdoppler sonography in predicting malignancy in 'cold' thyroid nodules, Eur J Endocrinol 1998 January; 138(1):41-6. [16] Bae U, Dighe M, Dubinsky T, et al., Ultrasound thyroid elastography using carotid artery pulsation: preliminary study, J Ultrasound Med. 2007 June; 26(6): 797-805. [17] Rago T, Santini F, Scutari M, Pinchera A, Vitti P., Elastography: new developments in ultrasound for predicting malignancy in thyroid nodules, J Clin Endocrinol Metab. 2007 August; 92(8):2917-22. [18] Sebastianes F M, Cerci J J, Zanoni P H, et al., Role of 18F-FDG PET in Preoperative Assessment of Cytologically Indeterminate Thyroid Nodules, J Clin Endocrinol Metab. 2007 Aug. 7. [19] De Geus-Oei L F, Pieters G F F M, Bonenkamp J J, et al, 18 F-FDG PET reduces unnecessary hemithyroidectomies for thyroid nodules with indeterminate cytologic results, J Nucl Med 2006; 47:770-775. [20] Fricke H, Morse S., The electric capacity of tumors of the breast, J Cancer Res 16:310-376. 1926. [21] Scholz B, Anderson R., On electrical impedance scanning—principles and simulations, Electromedica 2000; 68:35-44. [22] Glickman Y A, Filo O, David M, Yayon A, Topaz M, Zamir B, Ginzburg A, Rozenman D, Kenan G., Electrical impedance scanning: a new approach to skin cancer diagnosis, Skin Res Technol. 2003 August; 9(3):262-8. [23] Malich A, Fritsch T, Mauch C, et al., Electrical impedance scanning: a new technique in the diagnosis of lymph nodes in which malignancy is suspected on ultrasound, Br J. Radiol. 2001; 74(877):42-7. [24] Malich A, Boehm T, Facius M, et al., Use of electrical impedance scanning in the differentiation of sonographically suspicious and highly suspicious lymph nodes of the headneck region, Eur Radiol. 2002; 12(5):1114-20. [25] Mentzel H J, Malich A, Kentouche K, Freesmeyer M, Bottcher J, Schneider G, Gruhn B, Vogt S, Zintl F, Anderson R, Kaiser W A., Electrical impedance scanning-application of this new technique for lymph node evaluation in children, Pediatr Radiol. 2003; 33(7):461-6. [26] Malich A, Fritsch T, Anderson R, et al., Electrical impedance scanning for classifying suspicious breast lesions: first results, Eur Radiol. 2000; 10(10):1555-61. [27] Malich A, Boehm T, Facius M., Differentation of mammographically suspicious lesions: evaluation of breast ultrasound, MRI mammography and electrical impedance scanning as adjunctive technologies in breast cancer detection, Clinical Radiology 2001; 56: 278-83. [28] Fuchsjaeger M H, Flory D, Reiner C S, Rudas M, Riedl C C, Helbich T H, The negative predictive value of electrical impedance scanning in BI-RADS category IV breast lesions, Invest Radiol. 2005; 40(7):478-85. [29] Stojadinovic A, Nissan A, Gallimidi Z, et al., Electrical Impedance Scanning for the Early Detection of Breast Cancer in Young Women: Preliminary Results of a Multi-Center Prospective Clinical Trial, J Clin Oncol 2005; 23(12):2703-2715. [30] Stojadinovic A, Moskovitz O, Gallimidi Z, et al., Prospective Study of Electrical Impedance Scanning for Identifying Young Women at Risk for Breast Cancer, Br Cancer Res Treat 2006; 97(2): 179-89. [31] Tuttle R M, Lemar H, Burch H B, Clinical features associated with an increased risk of thyroid malignancy in patients with follicular neoplasia by fine-needle aspiration, Thyroid 1998 May; 8(5):377-83. [32] Montgomery, S. P., Swiecki, C. W. & Shriver, C. D., The evaluation of casualties from Operation Iraqi Freedom on return to the continental United States from March to June 2003, *J Am Coll Surg* 201:7-12; discussion 12-13 (2005). [33] Peoples, G. E., Jezior, J. R. & Shriver, C. D., Caring for the wounded in Iraq—a photo essay, *N Engl J Med* 351:2476-2480 (2004). [34] Owens, B. D., et al., Combat wounds in operation Iraqi Freedom and operation Enduring Freedom, *J Trauma* 64:295-299 (2008). [35] Marsh, D. J., Abu-Sitta, G. & Patel, H., The role of vacuum-assisted wound closure in blast injury, *Plast Reconstr Surg* 119:1978-1979 (2007). [36] Breugem, C. C. & Strackee, S. D., Is there evidence-based guidance for timing of soft tissue coverage of grade III B tibia fractures? *Int J Low Extrem Wounds* 5:261-270 (2006). [37] Nwomeh, B. C., Yager, D. R. & Cohen, I. K., Physiology of the chronic wound, *Clin Plast Surg* 25:341-356 (1998). [38] DeLong, W. G., Jr. & Born, C. T., Cytokines in patients with polytrauma, *Clin Orthop Relat Res:* 57-65 (2004). [39] Nast-Kolb, D., et al., Indicators of the posttraumatic inflammatory response correlate with organ failure in patients with multiple injuries, *J Trauma* 42, 446-454; discussion 454-445 (1997). [40] Endo, S., et al., Plasma endotoxin and cytokine concentrations in patients with hemorrhagic shock, *Crit Care Med* 22, 949-955 (1994). [41] Martin, C., Boisson, C., Haccoun, M., Thomachot, L. & Mege, J. L., Patterns of cytokine evolution (tumor necrosis factor-alpha and interleukin-6) after septic shock, hemorrhagic shock, and severe trauma, *Crit Care Med* 25, 1813-1819 (1997). [42] Biffl, W. L., Moore, E. E., Moore, F. A. & Peterson, V. M., Interleukin-6 in the injured patient. Marker of injury or mediator of inflammation? *Ann Surg* 224, 647-664 (1996). [43] Neidhardt, R., et al., Relationship of interleukin-10 plasma levels to severity of injury and clinical outcome in injured patients, *J Trauma* 42, 863-870; discussion 870-861 (1997). [44] Lyons, A., Kelly, J. L., Rodrick, M. L., Mannick, J. A. & Lederer, J. A., Major injury induces increased production of interleukin-10 by cells of the immune system with a negative impact on resistance to infection, *Ann Surg* 226, 450-458; discussion 458-460 (1997). [45] Regan, M. C., *Host defense dysfunction in trauma, shock and sepsis: mechanisms and therapeutic approaches*, (Springer, Berlin, 1993). [46] Robson, M. C., Wound infection. A failure of wound healing caused by an imbalance of bacteria, *Surg Clin North Am* 77, 637-650 (1997). [47] Medzhitov, R., Recognition of microorganisms and activation of the immune response, *Nature* 449, 819-826 (2007). [48] Dinarello, C. A., Proinflammatory cytokines, *Chest* 118:503-508 (2000). [49] Foex, B. A., et al., Early cytokine response to multiple injury, *Injury* 24:373-376 (1993). [50] Jemal A, Siegel R, Ward E, et al., Cancer Statistics 2009, CA Cancer J Clin 2009 July-August; 59(4):225-49. [51] Cancer Facts and Figures 2008, Atlanta, Ga.; American Cancer Society: 2009. [52] Saving Women's Lives: Strategies for Improving Breast Cancer Detection and Diagnosis, Joy J E, Penhoet E E, and Petitti D B, eds., Institute of Medicine and National Research Council of the National Academies, National Academy Press, Washington D.C., 2004. [53] Winchester D P, Osteen R T, Menck H R, The National Cancer Data Base report on breast carcinoma characteristics and outcome in relation to age, Cancer 1996; 78:1838-1843. [54] Chung M, Chang H R, Bland K I, Wanebo H J, Younger women with breast carcinoma have a poorer prognosis than older women, Cancer 1996; 77:97-103. [55] Xiong Q, Valero V, Kau V, et al., Female patients with breast carcinoma age 30 years and younger have a poor prognosis: The M.D. Anderson Cancer Center experience, Cancer 2001; 92(10):2523-8. [56] Smith R A, Saslow D, Sawyer Kans., et al., American Cancer Society guidelines for breast cancer screening: update 2003, CA Cancer J Clin 2003; 53(3): 141-69. [57] Kollias J, Sibbering D M, Blamey R W, et al., Screening women aged less than 50 years with a family history of breast cancer, Eur J Cancer 1998; 34:878-83. [58] Tilanus-Lindhorst M M, Bartels C C, Obedijn A L, Oudkerk M., Earlier detection of breast cancer by surveillance of women at familial risk, Eur J Cancer 2000; 36:514-19. [59] Carney P A, Miglioretti D L, Yankaskas B C, et al., Individual and combined effects of age, breast density, and hormone replacement therapy use on the accuracy of screening mammography, Ann. Intern. Med 2003; 138(3): 168-175. [60] Kroenke C H, Rosner B, Chen W Y, Kawachi I, Colditz G A, Holmes M D, Functional impact of breast cancer by age at diagnosis, J Clin Oncol 2004; 22(10): 1849-56. [61] Warner E, Plewes D B, Hill Kans., et al., Surveillance of BRCA1 and BRCA2 mutation carriers with magnetic resonance imaging, ultrasound, mammography, and clinical breast exam, JAMA 2004; 292: 1317-1325. [62] Morris E A, Schwartz L H, Dershaw D D, et al., MR imaging of the breast in patients with occult primary breast carcinoma, Radiology 1997; 205:437-440. [63] Orel S G, Schnall M D, LiVolsi V A, et al., Suspicious breast lesions: MR imaging with radiologic-pathologic correlation, Radiology 1994; 190:485-493. [64] Visvanathan K, Chlebowski R T, Hurley P, et al., American society of clinical oncology clinical practice guideline update on the use of pharmacologic interventions including tamoxifen, raloxifene, and aromatase inhibition for breast cancer risk reduction, J Clin Oncol. 2009 Jul. 1; 27(19):3235-58. Epub 2009 May 26. [65] Fisher B, Costaninno J P, Wickerham D L, et al., Tamoxifen for prevention of breast cancer: Report of the National Surgical Adjuvant Breast and Bowel Project P-1 Study, JNCI 1998; 90 (18): 1371-88. [66] Grann V R, Sundararajan V, Jacobson J S, et al., Decision analysis of tamoxifen for the prevention of invasive breast cancer, Cancer J Sci Am 2000; 6:169-178. [67] Hershman D, Sundararajan V, Jacobson J S, et al., Outcomes of tamoxifen chemoprevention for breast cancer in very high-risk women: A cost-effectiveness analysis, J Clin Oncol 2001; 20:9-16. [68] MacKarem G., The effectiveness of the Gail model in estimating risk for development of breast cancer in women under 40 years of age, Breast Journal 2001; 7(1):34-9. [69] Stojadinovic A, Nissan A, Gallimidi Z, et al., Electrical Impedance Scanning for the Early Detection of Breast Cancer in Young Women Preliminary Results of a Multi-Center Prospective Trial, Journal of Clinical Oncology 2005 Apr. 20; 23(12):2703-15. [70] Livak, K. J., and Schmittgen, T. D., Analysis of relative gene expression data using real-time quantitative PCR and the 2(-Delta Delta C(T)) Method. Methods 25: 402-408, 2001.

We claim:

1. A method for determining a patient-specific probability of transplant glomerulopathy, said method including:
    collecting clinical parameters from a plurality of patients to create a training database, the clinical parameters including biomarker levels from biopsy tissue;
    creating a fully unsupervised Bayesian Belief Network model using data from the training database;
    validating the fully unsupervised Bayesian Belief Network model;
    collecting the clinical parameters for an individual patient;
    receiving the clinical parameters for the individual patient into the fully unsupervised Bayesian Belief Network model;
    outputting the patient-specific probability of transplant glomerulopathy from the fully unsupervised Bayesian Belief Network model to a graphical user interface for use by a clinician; and
    updating the fully unsupervised Bayesian Belief Network model using the clinical parameters for the individual patient and the patient-specific probability of transplant glomerulopathy.

2. The method according to claim 1, wherein the biomarker levels include gene expression levels for an ICAM-1 gene, IL-10 gene, CCL-3 gene, CD-86 gene, CCL-2 gene, CXCL-11 gene, CD-80 gene, GNLY gene, and PRF-1 gene.

3. The method according to claim 2, wherein the biomarker levels further include gene expression levels for a CD40LG gene, IFNG gene, CD-28 gene, CXCL-10 gene, CCR-5 gene, CD-40 gene, CTLA-4 gene, TNF gene, CXCL-9 gene, CX3CR-1 gene, FOXP-3 gene, EDN-1 gene, CD-4 gene, TBX-21 gene, FASLG gene, C-3 gene, CD3E gene, CXCR-3 gene, and CCL-5 gene.

4. The method according to claim 1, wherein the biomarker levels include gene expression levels for the VCAM1 gene, MMP9 gene, Banff C4d gene, MMP7 gene, and LAMC2 gene.

5. The method according to claim 4, wherein the biomarker levels further include gene expression levels for a TNC gene, S100A4 gene, NPHS1 gene, NPHS2 gene, AFAP gene, PDGF8 gene, SERPINH1 gene, TIMP4 gene, TIMP3 gene, VIM gene, SERPINE1 gene, TIMP1 gene, FN1 gene, ANGPT2 gene, TGFB1 gene, ACTA2 gene, TIMP2 gene, COL4A2 gene, MMP2 gene, COL1A1 gene, COL3A1 gene, GREM1_2 gene, SPARC gene, IGF1 gene, SMAD3 gene, HSPG2 gene, FN1 gene, ANGPT2 gene, TGFB1 gene, ACTA2 gene, THBS1 gene, CTNNB1 gene, FGF2 gene, TJP1 gene, FAT gene, CDH1 gene, SMAD7 gene, CD2AP gene, CDH3 gene, CTGF gene, ACTN4 gene, SPP1 gene, AGRN gene, VEGF gene, and BMP7 gene.

6. The method according to claim 1, wherein said creating of the fully unsupervised Bayesian Belief Network model includes creating the fully unsupervised Bayesian Belief Network model without human-developed decision support rules.

7. The method according to claim 1, further including estimating an accuracy of the patient-specific probability of transplant glomerulopathy, the accuracy including at least one of model sensitivity, model specificity, positive and negative predictive values, and overall accuracy.

* * * * *